(12) United States Patent
Williams et al.

(10) Patent No.: US 9,474,848 B2
(45) Date of Patent: Oct. 25, 2016

(54) FLUID MANAGEMENT SYSTEM

(71) Applicant: Thermedx, LLC, Solon, OH (US)

(72) Inventors: Jeffrey B Williams, Hudson, OH (US); Douglas L Carr, Chardon, OH (US)

(73) Assignee: Thermedx, LLC, Solon, OH (US)

( * ) Notice: Subject to any disclaimer, the term of this patent is extended or adjusted under 35 U.S.C. 154(b) by 888 days.

(21) Appl. No.: 13/798,414

(22) Filed: Mar. 13, 2013

(65) Prior Publication Data

US 2013/0197471 A1    Aug. 1, 2013

Related U.S. Application Data

(63) Continuation-in-part of application No. 12/720,475, filed on Mar. 9, 2010, now Pat. No. 8,444,592.

(60) Provisional application No. 61/158,574, filed on Mar. 9, 2009.

(51) Int. Cl.

| | |
|---|---|
| *A61M 5/00* | (2006.01) |
| *A61M 3/02* | (2006.01) |
| *A61M 1/00* | (2006.01) |
| *A61M 5/44* | (2006.01) |
| *A61M 5/36* | (2006.01) |

(52) U.S. Cl.
CPC .......... *A61M 3/0229* (2013.01); *A61M 1/006* (2014.02); *A61M 1/0058* (2013.01); *A61M 5/44* (2013.01); *A61M 5/36* (2013.01); *A61M 2205/123* (2013.01); *A61M 2205/127* (2013.01); *A61M 2205/368* (2013.01); *A61M 2205/505* (2013.01)

(58) Field of Classification Search
CPC .... A61M 5/44; A61M 1/0058; A61M 1/006; A61M 2205/18
See application file for complete search history.

(56) References Cited

U.S. PATENT DOCUMENTS

| | | | |
|---|---|---|---|
| 3,475,590 A | 10/1969 | Pins | 392/470 |
| 3,515,137 A | 6/1970 | Santomieri | 604/165.02 |
| 4,180,074 A | 12/1979 | Murry et al. | 128/276 |
| 4,278,078 A | 7/1981 | Smith | 128/66 |
| 4,388,922 A | 6/1983 | Telang | 4/319 |
| 4,464,563 A | 8/1984 | Jewett | 219/298 |
| 4,574,876 A | 3/1986 | Aid | 165/46 |
| 4,759,749 A | 7/1988 | Verkaart | 604/113 |
| 4,844,074 A | 7/1989 | Kurucz | 128/401 |

(Continued)

FOREIGN PATENT DOCUMENTS

| | | | | |
|---|---|---|---|---|
| EP | 0 776 670 | 6/1997 | | A61M 1/00 |
| EP | 0 575 512 | 5/1998 | | A61M 5/44 |

(Continued)

OTHER PUBLICATIONS

International Search Report and Written Opinion for International Application No. PCT/US2010/026698, dated Jun. 29, 2010.

(Continued)

*Primary Examiner* — Aarti B Berdichevsky
(74) *Attorney, Agent, or Firm* — Kusner & Jaffe

(57) ABSTRACT

Fluid management system and method of operating a fluid management system which may provide one or more functions associated with suction, irrigation, distention, deficit monitoring, infusion, fluid warming, and the like. The fluid management system may be selectable between pressure control and flow control modes.

21 Claims, 55 Drawing Sheets

(56) References Cited

U.S. PATENT DOCUMENTS

| | | | | |
|---|---|---|---|---|
| 4,898,518 | A | 2/1990 | Hubbard et al. | 417/360 |
| 4,911,691 | A | 3/1990 | Aniuk et al. | 604/164 |
| 5,013,303 | A | 5/1991 | Tamari et al. | 604/140 |
| 5,050,266 | A | 9/1991 | Schneider | 15/421 |
| 5,106,373 | A | 4/1992 | Augustine et al. | 604/113 |
| 5,125,069 | A | 6/1992 | O'Boyle | 392/465 |
| 5,137,509 | A | 8/1992 | Freitas | 604/26 |
| 5,178,606 | A | 1/1993 | Ognier et al. | 604/31 |
| 5,195,958 | A | 3/1993 | Phillips | 604/33 |
| 5,224,929 | A | 7/1993 | Remiszewski | 604/30 |
| 5,228,646 | A | 7/1993 | Raines | 251/95 |
| 5,245,693 | A | 9/1993 | Ford et al. | 392/470 |
| 5,250,032 | A | 10/1993 | Carter, Jr. et al. | 604/113 |
| 5,254,094 | A | 10/1993 | Starkey et al. | 604/113 |
| 5,271,086 | A | 12/1993 | Kamiyama et al. | 392/483 |
| 5,303,735 | A | 4/1994 | Cerola et al. | 137/596.2 |
| D350,822 | S | 9/1994 | Lanigan | D24/111 |
| 5,347,992 | A | 9/1994 | Pearlman et al. | 128/4 |
| 5,368,569 | A | 11/1994 | Sanese | 604/113 |
| 5,381,510 | A | 1/1995 | Ford et al. | 392/470 |
| 5,382,805 | A | 1/1995 | Fannon et al. | 250/504 |
| 5,388,612 | A | 2/1995 | Cerola et al. | 137/596.2 |
| 5,391,145 | A | 2/1995 | Dorsey, III | 604/33 |
| D357,312 | S | 4/1995 | Riquier et al. | D24/111 |
| 5,420,962 | A | 5/1995 | Bakke | 392/470 |
| 5,427,144 | A | 6/1995 | Teets et al. | 137/614.2 |
| 5,447,494 | A | 9/1995 | Dorsey, III | 604/43 |
| 5,449,145 | A | 9/1995 | Wortrich | 251/322 |
| 5,460,490 | A | 10/1995 | Carr et al. | 417/44.2 |
| 5,496,314 | A | 3/1996 | Eggers | 606/41 |
| 5,505,710 | A | 4/1996 | Dorsey, III | 604/158 |
| 5,520,638 | A | 5/1996 | O'Quinn et al. | 604/67 |
| 5,522,796 | A | 6/1996 | Dorsey, III | 604/118 |
| 5,522,805 | A | 6/1996 | Vancaillie et al. | 604/246 |
| 5,551,448 | A | 9/1996 | Matula et al. | 128/987 |
| 5,559,924 | A | 9/1996 | Kadotani et al. | 392/483 |
| 5,562,640 | A | 10/1996 | McCabe et al. | 604/280 |
| 5,573,504 | A | 11/1996 | Dorsey, III | 604/35 |
| 5,586,977 | A | 12/1996 | Dorsey, III | 604/264 |
| 5,607,391 | A | 3/1997 | Klinger et al. | 604/33 |
| 5,626,563 | A | 5/1997 | Dodge et al. | 604/153 |
| 5,643,203 | A | 7/1997 | Beiser et al. | 604/66 |
| 5,683,381 | A | 11/1997 | Carr et al. | 606/27 |
| 5,690,614 | A | 11/1997 | Carr et al. | 604/114 |
| 5,729,653 | A | 3/1998 | Magliochetti et al. | 392/485 |
| 5,733,263 | A | 3/1998 | Wheatman | 604/141 |
| D398,051 | S | 9/1998 | Lanigan et al. | D24/108 |
| 5,800,383 | A | 9/1998 | Chandler et al. | 604/35 |
| 5,803,510 | A | 9/1998 | Dorsey, III | 285/148.23 |
| 5,807,313 | A | 9/1998 | Delk et al. | 604/35 |
| 5,807,332 | A | 9/1998 | Augustine et al. | 604/113 |
| 5,810,770 | A | 9/1998 | Chin et al. | 604/65 |
| 5,814,009 | A | 9/1998 | Wheatman | 604/21 |
| 5,830,180 | A | 11/1998 | Chandler et al. | 604/65 |
| 5,836,909 | A | 11/1998 | Cosmescu | 601/35 |
| 5,875,282 | A | 2/1999 | Jordan et al. | 392/470 |
| D409,748 | S | 5/1999 | Lanigan et al. | D24/127 |
| 5,914,047 | A | 6/1999 | Griffiths | 210/739 |
| 5,989,423 | A | 11/1999 | Kamen et al. | 210/258 |
| 5,993,410 | A | 11/1999 | Vincent et al. | 604/27 |
| 6,024,720 | A | 2/2000 | Chandler et al. | 604/35 |
| 6,047,108 | A | 4/2000 | Sword et al. | 392/470 |
| 6,074,363 | A | 6/2000 | Beran et al. | 604/113 |
| 6,106,494 | A | 8/2000 | Saravia et al. | 604/35 |
| 6,139,528 | A | 10/2000 | Kistner et al. | 604/114 |
| 6,139,571 | A | 10/2000 | Fuller et al. | 607/105 |
| 6,142,974 | A | 11/2000 | Kistner et al. | 604/113 |
| 6,146,359 | A | 11/2000 | Carr et al. | 604/114 |
| 6,149,622 | A | 11/2000 | Marie | 604/43 |
| 6,149,674 | A | 11/2000 | Borders | 607/96 |
| 6,175,688 | B1 | 1/2001 | Cassidy et al. | 392/470 |
| 6,176,847 | B1 | 1/2001 | Humphreys, Jr. et al. | 604/246 |
| 6,213,970 | B1 | 4/2001 | Nelson et al. | 604/35 |
| 6,234,205 | B1 | 5/2001 | D'Amelio et al. | 137/625.17 |
| 6,236,809 | B1 | 5/2001 | Cassidy et al. | 392/470 |
| 6,238,366 | B1 | 5/2001 | Savage et al. | 604/28 |
| 6,246,831 | B1 | 6/2001 | Seitz et al. | 392/486 |
| 6,257,265 | B1 | 7/2001 | Brunner et al. | 137/1 |
| 6,259,074 | B1 | 7/2001 | Brunner et al. | 219/497 |
| 6,261,261 | B1 | 7/2001 | Gordon | 604/113 |
| 6,336,003 | B1 | 1/2002 | Mitsunaga et al. | 392/470 |
| 6,358,224 | B1 | 3/2002 | Tims et al. | 604/30 |
| 6,406,470 | B1 | 6/2002 | Kierce | 604/535 |
| 6,413,233 | B1 | 7/2002 | Sites et al. | 604/6.13 |
| 6,464,666 | B1 | 10/2002 | Augustine et al. | 604/113 |
| 6,527,743 | B1 | 3/2003 | Fowler et al. | 604/131 |
| 6,535,689 | B2 | 3/2003 | Augustine et al. | 392/470 |
| 6,572,641 | B2 | 6/2003 | Brugger et al. | 607/106 |
| 6,572,689 | B2 | 6/2003 | Cosby, II et al. | 96/242 |
| 6,585,708 | B1 | 7/2003 | Maaskamp | 604/317 |
| 6,595,957 | B1 | 7/2003 | Griffiths et al. | 604/156 |
| 6,602,221 | B1 | 8/2003 | Saravia et al. | 604/31 |
| 6,620,130 | B1 | 9/2003 | Ginsburg | 604/113 |
| 6,635,031 | B2 | 10/2003 | French et al. | 604/131 |
| 6,635,034 | B1 | 10/2003 | Cosmescu | 604/289 |
| 6,641,556 | B1 | 11/2003 | Shigezawa | 604/113 |
| 6,645,232 | B2 | 11/2003 | Carson | 607/104 |
| 6,648,906 | B2 | 11/2003 | Lasheras et al. | 607/105 |
| 6,652,488 | B1 | 11/2003 | Cover et al. | 604/118 |
| 6,685,667 | B1 | 2/2004 | Delk et al. | 604/30 |
| 6,699,184 | B2 | 3/2004 | Felix et al. | 600/156 |
| 6,699,267 | B2 | 3/2004 | Voorhees et al. | 607/104 |
| 6,722,782 | B2 | 4/2004 | Faries, Jr. et al. | 374/162 |
| 6,743,201 | B1 | 6/2004 | Donig et al. | 604/114 |
| 6,775,473 | B2 | 8/2004 | Augustine et al. | 392/470 |
| 6,788,885 | B2 | 9/2004 | Mitsunaga et al. | 392/470 |
| 6,824,528 | B1 | 11/2004 | Faries, Jr. et al. | 604/113 |
| 6,875,198 | B2 | 4/2005 | Foley | 604/119 |
| 6,882,797 | B2 | 4/2005 | Stewart et al. | 392/470 |
| 6,899,697 | B2 | 5/2005 | Fowler et al. | 604/131 |
| 6,901,216 | B2 | 5/2005 | Jusiak et al. | 392/470 |
| 6,918,902 | B2 | 7/2005 | French et al. | 604/500 |
| 6,958,058 | B1 | 10/2005 | Hunter, Sr. et al. | 604/500 |
| 6,997,942 | B2 | 2/2006 | Machold et al. | 607/96 |
| 7,004,960 | B2 | 2/2006 | Daoud | 607/105 |
| 7,010,221 | B2 | 3/2006 | Augustine et al. | 392/470 |
| 7,031,602 | B2 | 4/2006 | Faries, Jr. et al. | 392/470 |
| 7,083,601 | B1 | 8/2006 | Cosmescu | 604/289 |
| 7,094,219 | B2 | 8/2006 | Noice et al. | 604/113 |
| 7,153,285 | B2 | 12/2006 | Lauman et al. | 604/6.08 |
| 7,158,719 | B2 | 1/2007 | Cassidy | 392/494 |
| 7,164,852 | B2 | 1/2007 | Cazzini et al. | 392/470 |
| 7,207,966 | B2 | 4/2007 | Savare et al. | 604/27 |
| 7,232,457 | B2 | 6/2007 | Schmidt et al. | 607/96 |
| 7,236,694 | B1 | 6/2007 | Chammas | 392/470 |
| 7,238,170 | B2 | 7/2007 | Park | 604/113 |
| 7,258,711 | B2 | 8/2007 | Dunn et al. | 55/385.1 |
| 7,261,557 | B2 | 8/2007 | Gill et al. | 431/328 |
| 7,273,359 | B2 | 9/2007 | Blight et al. | 417/477.13 |
| 7,297,133 | B2 | 11/2007 | Nelson et al. | 604/35 |
| 7,316,666 | B1 | 1/2008 | Entenman et al. | 604/113 |
| 7,394,976 | B2 | 7/2008 | Entenman et al. | 392/470 |
| 7,410,475 | B2 | 8/2008 | Krensky et al. | 604/29 |
| 7,458,951 | B2 | 12/2008 | Lauman et al. | 604/6.08 |
| 7,621,898 | B2 | 11/2009 | Lalomia et al. | 604/319 |
| D615,191 | S | 5/2010 | McGill et al. | D24/111 |
| D616,539 | S | 5/2010 | McGill | D24/111 |
| 7,753,880 | B2 | 7/2010 | Malackowski | 604/131 |
| 7,762,989 | B2 | 7/2010 | Simpson | 604/151 |
| D650,896 | S | 12/2011 | Mcgill et al. | D24/111 |
| 8,123,731 | B2 | 2/2012 | Ryan | 604/317 |
| 8,138,925 | B2 | 3/2012 | Downie et al. | 340/572.8 |
| 8,388,570 | B2 | 3/2013 | Kumar et al. | 604/30 |
| 8,562,577 | B2 | 10/2013 | Michaels et al. | 604/317 |
| 8,652,089 | B2 | 2/2014 | Kumar et al. | 604/30 |
| 2002/0032403 | A1 | 3/2002 | Savagle et al. | 604/28 |
| 2002/0096984 | A1 | 7/2002 | Konishi et al. | 313/25 |
| 2003/0004470 | A1 | 1/2003 | Hickerson et al. | 604/251 |
| 2003/0109826 | A1 | 6/2003 | Fowler et al. | 604/131 |
| 2003/0176833 | A1 | 9/2003 | Libermann | 604/65 |
| 2003/0212363 | A1 | 11/2003 | Shipp | 604/118 |
| 2003/0216689 | A1 | 11/2003 | Bouhuijs et al. | 604/113 |
| 2004/0097872 | A1 | 5/2004 | Delk et al. | 604/67 |
| 2004/0190884 | A1 | 9/2004 | Stewart et al. | 392/470 |

(56) References Cited

U.S. PATENT DOCUMENTS

| | | | |
|---|---|---|---|
| 2004/0204679 A1 | 10/2004 | Visconti et al. | 604/131 |
| 2005/0055074 A1 | 3/2005 | Tak et al. | 607/104 |
| 2005/0095155 A1 | 5/2005 | Blight et al. | 417/477.13 |
| 2005/0142013 A1 | 6/2005 | Faries, Jr. et al. | 414/477.2 |
| 2005/0148934 A1 | 7/2005 | Martens et al. | 604/113 |
| 2006/0122576 A1 | 6/2006 | Raja et al. | 604/890.1 |
| 2006/0148279 A1 | 7/2006 | German et al. | 439/49 |
| 2006/0210255 A1 | 9/2006 | Cassidy | 392/470 |
| 2006/0222350 A1 | 10/2006 | Cassidy | 392/470 |
| 2006/0253075 A1 | 11/2006 | Faries et al. | 604/113 |
| 2007/0045272 A1 | 3/2007 | French et al. | 219/216 |
| 2007/0129707 A1 | 6/2007 | Blott et al. | 604/543 |
| 2007/0142773 A1 | 6/2007 | Rosiello et al. | 604/113 |
| 2007/0142775 A1 | 6/2007 | Visconti et al. | 604/131 |
| 2007/0159337 A1 | 7/2007 | Tethrake et al. | 340/572.8 |
| 2007/0161978 A1 | 7/2007 | Fedenia et al. | 606/34 |
| 2007/0217948 A1 | 9/2007 | Ghelli et al. | 422/45 |
| 2007/0233003 A1 | 10/2007 | Radgowski et al. | 604/151 |
| 2007/0242934 A1 | 10/2007 | Entenman et al. | 392/465 |
| 2007/0265689 A1 | 11/2007 | Frey | 607/105 |
| 2008/0031773 A1 | 2/2008 | Eccleston | 422/44 |
| 2008/0039815 A1 | 2/2008 | Ogawa | 604/408 |
| 2008/0077087 A1 | 3/2008 | Martens | 604/113 |
| 2008/0093276 A1 | 4/2008 | Roger et al. | 210/104 |
| 2008/0145249 A1 | 6/2008 | Smisson et al. | 417/474 |
| 2008/0154095 A1 | 6/2008 | Stubkjaer et al. | 600/156 |
| 2009/0009290 A1 | 1/2009 | Kneip et al. | 340/10 |
| 2010/0151785 A1 | 6/2010 | Steeger et al. | 455/41.1 |
| 2010/0228222 A1 | 9/2010 | Williams et al. | 604/500 |
| 2010/0228224 A1 | 9/2010 | Pyles et al. | 604/500 |
| 2011/0144812 A1 | 6/2011 | Davis et al. | 700/281 |
| 2011/0162333 A1 | 7/2011 | Cook et al. | 53/507 |
| 2013/0079702 A1 | 3/2013 | Klein et al. | 604/22 |
| 2016/0151557 A1 | 6/2016 | Woolford et al. | 606/86 R |

FOREIGN PATENT DOCUMENTS

| | | | | |
|---|---|---|---|---|
| GB | 2 242 367 | 10/1991 | | A61M 1/32 |
| WO | WO 87/00759 | 2/1987 | | A61M 7/00 |
| WO | WO 92/17040 | 10/1992 | | H05B 1/02 |
| WO | WO 96/13216 | 5/1996 | | A61B 17/36 |
| WO | WO 00/47283 | 8/2000 | | A61N 5/04 |
| WO | WO 2010/104878 | 9/2010 | | A61M 1/00 |

OTHER PUBLICATIONS

The Surgical Company, Fluido® Product Information obtained from website www.fluido.nl, Jan. 18, 2008.
Smiths-Medical.com, Blood & Fluid Warming Systems (Level 1®) H-1200 Fast Flow Fluid Warmer with Integrated Air Detector/Clamp, 2008.
Ranger Blood/Fluid Warming, Ranger® Blood and Fluid Warming Systems Product Specifications, 2008.
Paladin Biomedical Corporation, In-Line Microwave Fluid Warming Technology[1,2], T900™ system, 2004.
Smiths-Medical.com, Blood & Fluid Warming Systems (Level 1®), NormoFlo® Irrigating System, Level 1, 2008.
Ranger Irrigation Fluid Warming, Ranger® Blood and Fluid Warming Systems, Ranger Irrigation Fluid Warming System, 2008.
Socomed, Endoflow® by SOCOMED, slide presentation, prior to Sep. 2008.
Stryker® UK, Strykflow 2 Suction & Irrigation System, 2008.
Stryker, Stryket AHTO™ Irrigation System, Dec. 2004.
Olympus, Surgiflow, Irrigation Pump, Feb. 2006.
Olympus, Surgipump, Suction/Irrigation Pump, Feb. 2006.
Olympus, Eco-Pump, Irrigation Pump, Feb. 2006.
CardinalHealth, Hydroline® and PulseWave® Laparoscopic Suction/Irrigation Systems, 2003.
Gaymar®, Medi-Temp III™, Blood/Fluid Warming, prior to Sep. 2008.
Belmont Instrument Corporation, FMS 2000 Rapid Infuser, 2003.
Belmont Instrument Corporation, buddy™, Fluid Warmer, 2003.
Astotherm®, Astotherm® plus 220, Blood and Infusion Warmer, prior to Sep. 2008.
Futuremed®, Animec™ AM-2S, Fluid Warmer, 2000-2007.
Vital Signs Inc., Medical Products, enFlow®, IV Fluid/Blood Warming System, prior to Sep. 2008.
Smiths-Medical.com, Blood & Fluid Warming Systems (Level 1®) HOTLINE® Blood and Fluid Warmer, 2008.
Stryker®, Pulsed Lavage, Interpulse—Pulsed Lavage, Wound Care, 2008.
Simpulse* VariCare* System, Wound Management, 2007.
Zimmer, Pulsavac®, Wound Debridement System, 1998.
Zimmer, Pulsavac Plus System, Wound Debridement System, Nov. 2, 2005.
Zimmer, Pulsavac Plus AC, Wound Debridement System, Jun. 8, 2008.
Richard Wolf Medical Instruments Corporation, The Richard Wolf Fluid Manager, Hysteroscopic Fluid Monitoring, prior to Sep. 2008.
Olympus, Fluid Management Products, Dolphin® II and Disten-U-Flo Fluid Management Systems for Hysteroscopy, 2008.
Olympus, HysteroFlow/HysteroBalance, Fluid Management, prior to Sep. 2008.
Stryker, Stryker Fluid Management, FluidSafe Fluid Management System, prior to Sep. 2008.
Young, RN. et al., Perioperative Fluid Management, AORN Journal, vol. 89, No. 1, Jan. 2009, pp. 167-183.
Smith et al., Principles of Fluid and Blood Warming in Trauma, International TraumaCare (ITACCS), vol. 18, No. 1, 2008, pp. 71-79.
Bard, Medical Division, Company Information obtained from website www.bardmedical.com, Jan. 29, 2008.
C Change Surgical, Press Release obtained from website www.cchangesurgical.com, Jul. 24, 2007.
C Change Surgical, IntraTemp™, Product Information obtained from website www.cchangesurgical.com, Jan. 18, 2008.
C Change Surgical, Press Releases, Jul. 2004-Feb. 2008.
CardinalHealth, Medi-Vac® Suction and Wound and Drainage Product Information obtained from website www.cardinal.com, Jan. 18, 2008.
Davol Inc., Laparoscopy Surgical Product Information obtained from website www.davol.com, Jan. 18, 2008.
Ethicon, Inc., Product Catalog obtained from website ecatalog.ethicon.com, Jan. 18, 2008.
Johnson & Johnson Gateway®, Product Information, Fluid Management System, obtained from website www.jnjgateway.com, Jan. 18, 2008.
Gyrus ACMI, Gyrus Medical, Niagara TRS® Thermal Retention System Product Information obtained from website www.acmicorp.com, Jan. 18, 2008.
Innercool Therapies, Inc., Celsius Control System™, Product Information obtained from website www.innercool.com, Jan. 28, 2008.
Medical Solutions, Inc., Fluid Warming System, Product Information obtained from website www.warmiv.com, Jan. 25, 2008.
Nellcor Press Release, Nellcor Expands Warmflo Fluid and Blood Warming Solutions with New Warming Cassette, obtained from website www.cyperus.com, Jan. 18, 2008.
Nellcor, Products Listing obtained from website www.nellcor.com, Jan. 18, 2008.
Nellcor, Warmflo® Pressure Infusor Product Information obtained from website www.nellcor.com, Oct. 2, 2007.
Nellcor, Warmflo® Fluid Warming System Brochure, 2002.
Olympus, High Definition Video Laparoscopes, HD Endoeye™, Product Information obtained from website www.olympussurgical.com, Jan. 24, 2008.
Olympus, UHI-3 High Flow Insufflation Unit Product Information obtained from website www.olympusmedical.co.kr, Jan. 18, 2008.

(56) References Cited

OTHER PUBLICATIONS

Olympus, UHI-3 High Flow Insufflation Unit Product Information obtained from website www.olympusaustralia.com.au, Jan. 18, 2008.
Paladin Biomedical Corporation, ThermoStat™ 900 Blood and Fluid Warmer Product Information obtained from paladinbiomedical.com, Jan. 22, 2008.
Radiant Medical, Inc. Company Profile obtained from Silicon Valley/San Jose Business Journal website www.bizjournals.com, Jan. 25, 2008.
Radiant Medical, Inc. Press Release, Oct. 12, 2005.
Sanese Medical Corp., Thermo-Flo System 3, Product Information, search results for "new products" search of website speechtherapist.com, pp. 4-5, Jan. 18, 2008.
Karl Storz, Suction and Irrigation Systems Product Information obtained from website www.websurg.com, Jan. 28, 2009.
Stryker, Endoscopy, Stryket AHTO™ Irrigation System Product Catalog, Dec. 2004.
Stryker® Instruments, Orthopedics, InterPulse Battery Powered Irrigation Product Catalog, prior to Sep. 2008.
Stryker, Stryker StrykeFlow 2 Product Information obtained from website www.stryker.com, Jan. 18, 2008.
Stryker, Stryker AHTO Irrigation System Product Information obtained from website www.stryker.com, Jan. 18, 2008.
TSCI Company Profile obtained from website www.fluido.nl, Jan. 18, 2008.
TSCI Press Release obtained from website www.fluido.nl, Jan. 18, 2008.
CystoMedix, Company/Product Information obtained from website www.cystomedix.com, Jan. 28, 2010.

FLUID MANAGEMENT SYSTEM

RELATED APPLICATIONS

This application is a continuation-in-part (CIP) of U.S. application Ser. No. 12/720,475, filed Mar. 9, 2010, which claims the benefit of U.S. Provisional Application No. 61/158,574, filed Mar. 9, 2009, said patent applications herein fully incorporated by reference.

This application is related to co-pending U.S. application Ser. Nos. 12/720,488, filed Mar. 9, 2010, and 12/720,496, filed Mar. 9, 2010, and U.S. Design patent application No. 29/357,184, filed Mar. 8, 2010 (now U.S. Design Pat. No. D657,865).

BACKGROUND OF THE INVENTION

The present invention is directed to fluid management systems and, more particularly, to fluid management systems providing one or more functions associated with suction, irrigation, distention, deficit monitoring, infusion, fluid warming, and the like.

SUMMARY OF THE INVENTION

Exemplary embodiments may include surgical fluid management systems and methods of operating surgical fluid management systems, which may provide one or more functions associated with suction, irrigation, distention, deficit monitoring, infusion, fluid warming, and the like. Some example embodiments may include infrared lamps arranged to warm fluid flowing through a disposable cartridge. Some example embodiments may provide a three-dimensional fluid path through the cartridge and/or multi-stage heating capabilities. Some example fluid management systems may be selectable between pressure control and flow control modes.

In an aspect, a surgical fluid management system may include a pump configured to deliver a fluid to a surgical site; and a control system, the control system being user-selectable between a pressure control mode and a flow control mode. The pressure control mode may include controlling the pump to deliver the fluid to the surgical site at approximately a target pressure, and the flow control mode may include controlling the pump to deliver the fluid to the surgical site at approximately a target flow rate.

In a detailed embodiment, a surgical fluid management system may include at least one pressure sensor configured to generate a pressure signal associated with a pressure of the fluid and/or the control system may be configured to control the pump in the pressure control mode based at least in part upon the pressure signal. In a detailed embodiment, the at least one pressure sensor may include at least a first pressure sensor and a second pressure sensor, the first pressure sensor and the second pressure being configured to generate respective pressure signals associated with the pressure of the fluid. In a detailed embodiment, the control system may be configured to compare the first pressure signal and the second pressure signal and/or may be configured such that if the first pressure signal and the second pressure signal differ by an amount in excess of an acceptable tolerance band, the control system may automatically stop the pump.

In a detailed embodiment, the pump may include a positive displacement pump, a fluid flow rate through the pump may be substantially directly related to a speed of operation of the pump, and/or the control system may be configured to control the pump in the flow control mode based at least in part upon a flow rate calculated based upon the speed of the pump.

In a detailed embodiment, a surgical fluid management system may include a heater assembly configured to heat the fluid between a fluid supply container and the surgical site. In a detailed embodiment, a surgical fluid management system may include a touch screen interface configured to display at least one operating parameter and to receive at least one command, and the control system may be selectable between the pressure control mode and the flow control mode using the touch screen. In a detailed embodiment, the touch screen may be configurable with respect to at least one of content and layout.

In an aspect, a surgical fluid management device may include a pump configured to propel fluid from a fluid supply container to a surgical site; a heater assembly configured to heat the fluid as it is propelled from the fluid source to the surgical site; and a control system operatively connected to the pump and the heater assembly. The control system may be configured to control the pump and the heater assembly in at least a distention mode and an irrigation mode, the distention mode may include operation of the pump to maintain a fluid pressure within a predetermined pressure band, the irrigation mode may include operation of the pump to provide a fluid flow rate within a predetermined flow rate band, and/or the control system may be configured to control the heater to maintain a temperature of the fluid delivered to the surgical site within a predetermined temperature band in at least the distention mode and/or the irrigation mode.

In a detailed embodiment, the distention mode may include calculation of a fluid deficit associated with a difference between a volume of fluid delivered to the surgical site and a volume of fluid returned from the surgical site. In a detailed embodiment, a surgical fluid management device may include at least one load cell configured to generate an electrical signal associated with a weight of a fluid supply container and/or at least one load cell configured to generate an electrical signal associated with a weight of a fluid collection container. The control system may be operative to calculate a difference between an initial total system weight including an initial weight of the fluid supply container and an initial weight of the fluid collection container and current total system weight including the current weight of the fluid supply container and the current weight of the fluid collection container.

In a detailed embodiment, the control system may be operative to control the pump and the heater in an infusion mode. The infusion mode may include operating the pump to infuse the fluid at a desired flow rate while monitoring at least one bubble detector, the bubble detector being operatively connected to the control system such that detection of a bubble results in stopping the pump.

In a detailed embodiment, a surgical fluid management device may include a tubing and cartridge set including a cartridge configured to be received within the heater assembly, the cartridge including an internal fluid path, a first section of tubing extending at least partway from the source of fluid to the cartridge, and a second section of tubing extending from the cartridge at least partway to the surgical site.

In a detailed embodiment, the pump may include a positive displacement pump. In a detailed embodiment, the positive displacement pump may include a peristaltic pump configured to receive at least a portion of the first section of tubing.

In an aspect, a surgical fluid management system may include a pump configured to deliver fluid to a surgical site; a heater configured to heat the fluid prior to delivery to the surgical site; and a control system operatively connected to the pump and the heater, the control system being configurable to control the pump to deliver the fluid to the surgical site at at least one of a desired flow rate and a desired pressure, and to control the heater to warm the fluid to a desired temperature.

In a detailed embodiment, the control system may be configured to control the pump by adjusting a speed of the pump to maintain the desired flow rate. In a detailed embodiment, the control system is configured to control the heater by adjusting the heater to maintain the desired fluid temperature based on an inlet fluid temperature, an outlet fluid temperature, and the flow rate.

In an aspect, a disposable tubing and cartridge set for a surgical fluid management may include a connector adapted to couple with a fluid supply container; a heating cartridge configured to be received within a heater assembly of a surgical fluid management system; a trumpet valve; an upstream irrigation tubing section fluidicly coupling the connector and the heating cartridge; a downstream irrigation tubing section fluidicly coupling the heating cartridge and the trumpet valve; and a suction tubing section fluidicly coupled to the trumpet valve and including an end configured for coupling to a fluid collection container.

In a detailed embodiment, the trumpet valve may include a tip configured for suction and irrigation. In a detailed embodiment, the probe may include an electrosurgical tip.

In an aspect, a surgical fluid management system may include a pump configured to deliver fluid to a body cavity for distention of the body cavity; a remote pressure sensor configured for placement in the body cavity; and a control system operatively connected to the pump and the remote pressure sensor, the control system being configured to receive, from the remote pressure sensor, a signal associated with a pressure of the fluid within the body. The control system may be configured to adjust a speed of the pump to maintain a desired fluid pressure based at least in part upon the signal from the remote pressure sensor.

In a detailed embodiment, the control system may be configured to receive at least one of a pneumatic signal or an electrical signal from the remote pressure sensor.

In an aspect, a method for operating surgical fluid management system may include delivering fluid from a fluid supply container to a surgical site via a tubing set; sensing a system fluid pressure in the tubing set between the fluid supply container and the surgical site; sensing a surgical site fluid pressure using a remote pressure sensor disposed approximate the surgical site; and controlling a pressure of the fluid delivered to the surgical site based at least in part upon at least one of the sensed system fluid pressure and the sensed surgical site fluid pressure.

In a detailed embodiment, controlling the pressure of the fluid delivered to the surgical site may be based at least in part upon both the sensed system fluid pressure and the sensed surgical site fluid pressure. In a detailed embodiment, the tubing set may include a disposable tubing set including a pressure relief valve.

In an aspect, a suction container support assembly may include a suction container support including a plurality of openings, each of the plurality of openings being configured to receive an individual suction container therein; and a base comprising at least three spaced-apart load cells, the suction container support being substantially supported by the at least three spaced-apart load cells. The plurality of openings may be arranged such that individual centers of mass of the suction containers received within the openings may be disposed inwardly with respect to the spaced-apart load cells.

In a detailed embodiment, the base may include four substantially symmetrically spaced-apart load cells and/or the suction container support may include four substantially symmetrically arranged openings.

In a detailed embodiment, individual ones of the plurality of openings may be independently adjustable to receive suction containers of a plurality of sizes. In a detailed embodiment, a suction container support assembly may include, for each of the plurality of openings, a generally radially slidable adjuster, the adjusting being selectively securable in a desired position by a respective knob.

In an aspect, a method of operating a surgical fluid management system may include delivering fluid to a surgical site using a pump; and controlling operation of the pump based at least in part upon a pressure trend, the pressure trend including a current measured pressure as compared to a set point pressure and a previous measured pressure as compared to the set point pressure.

In a detailed embodiment, controlling operation of the pump may include classifying the previous measured pressure as compared to the set point pressure as corresponding to one of a plurality of zones and/or classifying the current measured pressure as compared to the set point pressure as corresponding to one of the plurality of zones.

In a detailed embodiment, the plurality of zones may include a first zone less than a lowest value of a set point tolerance band, a second zone between the lowest value of the set point tolerance band and the set point, a third zone between the set point and the highest value of the set point tolerance band, a fourth zone between the highest value of the set point tolerance band and a high pressure alarm level, and/or a fifth zone above the high pressure alarm level. In a detailed embodiment, controlling operation of the pump may include selecting one of a plurality of control modes based at least in part upon the zone corresponding to the current measured pressure and the zone corresponding to the previous measured pressure.

In a detailed embodiment, the plurality of control modes may include at least one of a slope mode, the slope mode including calculating a desired rate of pressure change, and adjusting operation of the pump to achieve the desired rate of pressure change; an integral control mode, the integral control mode including calculating an integral of a pressure error over time, the pressure error being determined by subtracting a respective measured pressure from the set point pressure, and adjusting operation of the pump to incrementally adjust a fluid flow rate based at least in part upon the integral of the pressure error; a coast mode, the coast mode including substantially maintaining a speed of the pump; a reduction mode, the reduction mode including, if the current measured pressure is less than the previous measure pressure, substantially maintaining the speed of the pump, and, if the current measured pressure is not less than the previous measured pressure, reducing the speed of the pump; and/or a reverse mode, the reverse mode including reversing operation of the pump until a subsequent measured pressure is below a desired pressure level.

In a detailed embodiment, in the integral control mode, adjusting operation of the pump to incrementally adjust the fluid flow rate may include adjusting operation of the pump to change the fluid flow rate in increments of about ±1 ml/min. In a detailed embodiment, in the reduction mode, if the current measured pressure is not less than the previous measured pressure, reducing the speed of the pump based at least in part upon a difference between the current measured pressure and the set point pressure.

In a detailed embodiment, selecting one of the plurality of control modes based at least in part upon the zone corresponding to the current measured pressure and the zone corresponding to the previous measured pressure may include, if the current measured pressure corresponds to the second zone and the previous measured pressure corresponds to the first zone, selecting the slope control mode; if the current measured pressure corresponds to the third zone and the previous measured pressure corresponds to the second zone, selecting the integral control mode; if the current measured pressure corresponds to the fourth zone and the previous measured pressure corresponds to the third zone and if the fluid flow rate is greater than 0, selecting the reduction mode; if the current measured pressure corresponds to the fourth zone and the previous measured pressure corresponds to the third zone and if the fluid flow rate is not greater than 0, selecting the reverse mode; if the current measured pressure corresponds to the fifth zone and the previous measured pressure corresponds to the fourth zone and if the fluid flow rate is not greater than 0, selecting the reduction mode; if the current measured pressure corresponds to the fifth zone and the previous measured pressure corresponds to the fourth zone and if the fluid flow rate is not greater than 0, selecting the reverse mode; if the current measured pressure corresponds to the fourth zone and the previous measured pressure corresponds to the fifth zone and if the fluid flow rate is not greater than 0, selecting the reduction mode; if the current measured pressure corresponds to the fourth zone and the previous measured pressure corresponds to the fifth zone and if the fluid flow rate is not greater than 0, selecting the reverse mode; if the current measured pressure corresponds to the third zone and the previous measured pressure corresponds to the fourth zone or the fifth zone, selecting the coast mode; if the current measured pressure corresponds to the second zone and the previous measured pressure corresponds to the third zone, selecting the integral control mode; and/or if the current measured pressure corresponds to the second zone and the previous measured pressure corresponds to the fourth zone or the fifth zone, selecting the slope mode.

In an aspect, a method of operating a surgical fluid management system may include delivering fluid to a surgical site using a pump; and controlling operation of the pump including selecting one of a plurality of pressure control modes based at least in part upon measured conditions, and adjusting operation of the pump using the selected control mode.

In a detailed embodiment, the plurality of pressure control modes may include at least one of a slope mode, the slope mode including calculating a desired rate of pressure change, and adjusting operation of the pump to achieve the desired rate of pressure change; an integral control mode, the integral control mode including calculating an integral of a pressure error over time, the pressure error being determined by subtracting a respective measured pressure from the set point pressure, and adjusting operation of the pump to incrementally adjust a fluid flow rate based at least in part upon the integral of the pressure error; a coast mode, the coast mode including substantially maintaining a speed of the pump; a reduction mode, the reduction mode including, if the current measured pressure is less than the previous measure pressure, substantially maintaining the speed of the pump, and, if the current measured pressure is not less than the previous measured pressure, reducing the speed of the pump; and/or a reverse mode, the reverse mode including reversing operation of the pump until a subsequent measured pressure is below a desired pressure level.

In a detailed embodiment, in the integral control mode, adjusting operation of the pump to incrementally adjust the fluid flow rate may include adjusting operation of the pump to change the fluid flow rate in increments of about ±1 ml/min. In a detailed embodiment, in the reduction mode, if the current measured pressure is not less than the previous measured pressure, reducing the speed of the pump based at least in part upon a difference between the current measured pressure and the set point pressure.

In a detailed embodiment, selecting the one of the plurality of pressure control modes based at least in part upon measured conditions may include classifying a previous measured pressure as compared to a set point pressure as corresponding to one of a plurality of zones; classifying a current measured pressure as compared to the set point pressure as corresponding to one of the plurality of zones; and/or selecting the one of the plurality of pressure control modes based at least in part upon the zone corresponding to the current measured pressure and the zone corresponding to the previous measured pressure.

In a detailed embodiment, the plurality of zones may include a first zone less than a lowest value of a set point tolerance band, a second zone between the lowest value of the set point tolerance band and the set point, a third zone between the set point and the highest value of the set point tolerance band, a fourth zone between the highest value of the set point tolerance band and a high pressure alarm level, and a fifth zone above the high pressure alarm level.

In a detailed embodiment, selecting the one of the plurality of pressure control modes may include, if the current measured pressure corresponds to the second zone and the previous measured pressure corresponds to the first zone, selecting the slope control mode; if the current measured pressure corresponds to the third zone and the previous measured pressure corresponds to the second zone, selecting the integral control mode; if the current measured pressure corresponds to the fourth zone and the previous measured pressure corresponds to the third zone and if the fluid flow rate is greater than 0, selecting the reduction mode; if the current measured pressure corresponds to the fourth zone and the previous measured pressure corresponds to the third zone and if the fluid flow rate is not greater than 0, selecting the reverse mode; if the current measured pressure corresponds to the fifth zone and the previous measured pressure corresponds to the fourth zone and if the fluid flow rate is not greater than 0, selecting the reduction mode; if the current measured pressure corresponds to the fifth zone and the previous measured pressure corresponds to the fourth zone and if the fluid flow rate is not greater than 0, selecting the reverse mode; if the current measured pressure corresponds to the fourth zone and the previous measured pressure corresponds to the fifth zone and if the fluid flow rate is not greater than 0, selecting the reduction mode; if the current measured pressure corresponds to the fourth zone and the previous measured pressure corresponds to the fifth zone and if the fluid flow rate is not greater than 0, selecting the reverse mode; if the current measured pressure corresponds to the third zone and the previous measured pressure corresponds to the fourth zone or the fifth zone, selecting the coast mode; if the current measured pressure corresponds to the second zone and the previous measured pressure corresponds to the third zone, selecting the integral control mode; and/or if the current measured pressure corresponds to the second zone and the previous measured pressure corresponds to the fourth zone or the fifth zone, selecting the slope mode.

In an aspect, a tubing and cartridge set for a surgical fluid management system configured to receive fluid from a fluid supply container and to deliver the fluid to a surgical instrument may include a heating cartridge configured to be releasably received in a heater assembly, the heating cartridge including a three-dimensional fluid path therethrough; an upstream tubing section fluidicly interposing a fluid supply container and the heating cartridge; and a downstream tubing section fluidicly interposing the heating cartridge and a surgical instrument.

In a detailed embodiment, the three-dimensional fluid path may include a first fluid channel oriented in a first direction, a second fluid channel oriented in a second direction, the second direction being substantially opposite the first direction, and a port fluidicly connecting the first fluid channel to the second fluid channel. The first fluid channel may be disposed on a first side of a main body of the heating cartridge, the second fluid channel may be disposed on a second side of the main body of the heating cartridge, the first fluid channel may face outwardly from the first side of the heating cartridge, and/or the second fluid channel may face outwardly from the second side of the heating cartridge.

In a detailed embodiment, the three-dimensional fluid path may include a third fluid channel on the second side of the main body and generally adjacent to the second fluid channel, the third fluid channel being oriented generally in the first direction. The three-dimensional fluid path may include a fourth fluid channel on the first side of the main body and generally adjacent to the first fluid channel, the fourth fluid channel being oriented generally in the second direction. The third fluid channel may face outwardly from the second side of the heating cartridge and/or the fourth fluid channel may face outwardly from the first side of the heating cartridge.

In a detailed embodiment, the heating cartridge may include a first side sheet affixed to the first side of the main body and a second side sheet affixed to the second side of the main body. The first side sheet may at least partially define outwardly facing aspects of the first fluid channel and the fourth fluid channel and/or the first fluid channel and the fourth fluid channel may be disposed substantially against the first side sheet. The second side sheet may at least partially define outwardly facing aspects of the second fluid channel and the third fluid channel and/or the second fluid channel and the third fluid channel may be disposed substantially against the second side sheet.

In a detailed embodiment, a tubing and cartridge set may include a fitting configured to releasably couple with a corresponding fitting associated with the heater assembly upon insertion of the heating cartridge into the heater assembly and/or the fitting may be fluidicly connected to the fluid path. In a detailed embodiment, a tubing and cartridge set may include a hydrophobic filter fluidicly interposing the fitting and the fluid path, the hydrophobic filter being operative to prevent fluid from flowing from the fluid path through the fitting.

In a detailed embodiment, the heating cartridge may include at least one bubble trap configured to vent gas from the fluid path. In a detailed embodiment, the bubble trap may include an umbrella valve arranged to allow the gas to escape the fluid path without allowing air to enter the fluid path.

In an aspect, a cartridge for a surgical fluid management system may include an internal fluid path including a first channel extending along a first side of the cartridge, a first through-port to a second side of the cartridge, a second channel extending along the second side of the cartridge, a turn section, a third channel extending along the second side of the cartridge, a second through-port to the first side of the cartridge, and a fourth channel extending along the first side of the cartridge.

In a detailed embodiment, the first channel, the second channel, the third channel, and the fourth channel have generally flattened shapes. In a detailed embodiment, the first channel, the second channel, the third channel, and the fourth channel have lengths and heights which are substantially greater than their thicknesses.

In a detailed embodiment, a cartridge may include an inlet fitting fluidicly connected to the first channel, and an outlet fitting fluidicly connected to the fourth channel. In a detailed embodiment, a cartridge may include a first bubble trap between the inlet fitting and the first channel. In a detailed embodiment, a cartridge may include a second bubble trap between the fourth channel and the outlet fitting. In a detailed embodiment, at least one of the first bubble trap and the second bubble trap may include a hydrophobic membrane. The hydrophobic membrane may be disposed within the cartridge such that the hydrophobic membrane is canted with respect to vertical when the cartridge is in use, the hydrophobic membrane being canted towards a fluid-contacting side.

In a detailed embodiment, a cartridge may include a substantially rigid main body and two relatively flexible side sheets, the main body and the side sheets defining the first channel, the second channel, the third channel, and the fourth channel. In a detailed embodiment, the main body may include molded polycarbonate; the side sheets may be constructed from polycarbonate and welded to the main body.

In a detailed embodiment, a cartridge may include a pressure sensor fitting configured to couple with a corresponding fitting in a heater assembly upon insertion of the cartridge into the heater assembly. The pressure sensor fitting may be fluidicly connected to the internal fluid path. In a detailed embodiment, a cartridge may include a hydrophobic filter fluidicly interposing the pressure sensor fitting and the internal fluid path, the hydrophobic filter being operative to prevent fluid from flowing through the pressure sensor fitting. In a detailed embodiment, a cartridge may include a pressure sensor fluid path fluidicly connecting the internal fluid path and the hydrophobic filter. The pressure sensor fluid path may be configured to retain a volume of gas adjacent to the hydrophobic filter.

In an aspect, a heater assembly for a surgical fluid management device may include a slot configured to receive a cartridge slidably therein; a first infrared lamp mounted adjacent a first side of the slot; a second infrared lamp mounted adjacent the first side of the slot; a third infrared lamp mounted adjacent a second side of the slot; and a fourth infrared lamp mounted adjacent the second side of the slot. The first infrared lamp may be substantially elongated and/or may be configured to heat fluid within a first flow channel of the cartridge, the second infrared lamp may be substantially elongated and/or may be configured to heat fluid within a second flow channel of the cartridge, the third infrared lamp may be substantially elongated and/or may be configured to heat fluid within a third flow channel of the cartridge, and/or the fourth infrared lamp may be substantially elongated and/or may be configured to heat fluid within a fourth flow channel of the cartridge. At least one of the first infrared lamp, the second infrared lamp, the third infrared lamp, and/or the fourth infrared lamp may be mounted generally parallel with a respective one of the first flow channel, the second flow channel, the third flow channel, and/or the fourth flow channel.

In a detailed embodiment, the first infrared lamp and the second infrared lamp may be operatively connected to be controlled as a pair; the third infrared lamp and the fourth infrared lamp may be operatively connected to be controlled as a pair; and fluid may flow through the cartridge from the first flow channel to the second flow channel, from the second flow channel to the third flow channel, and from the third flow channel to the fourth flow channel.

In a detailed embodiment, a heater assembly may include an inlet temperature sensor, an intermediate temperature sensor, and/or a outlet temperature sensor. The first flow channel and the second flow channel may be fluidicly between the inlet temperature sensor and the intermediate temperature sensor, and the third flow channel and the fourth flow channel may be fluidicly between the intermediate temperature sensor and the outlet temperature sensor. A level of power applied to the first infrared lamp and the second infrared lamp may be determined at least in part by a signal from the inlet temperature sensor and/or a level of power applied to the third infrared lamp and the fourth infrared lamp may be determined at least in part by a signal from the outlet temperature sensor.

In a detailed embodiment, a heater assembly may include a first reflector associated with the first infrared lamp and arranged to direct infrared energy emitted by the first infrared lamp onto the first flow channel, a second reflector associated with the second infrared lamp and arranged to direct infrared energy emitted by the second infrared lamp onto the second flow channel, a third reflector associated with the third infrared lamp and arranged to direct infrared energy emitted by the third infrared lamp onto the third flow channel, and/or a fourth reflector associated with the fourth infrared lamp and arranged to direct infrared energy emitted by the fourth infrared lamp onto the fourth flow channel. In a detailed embodiment, at least a portion of at least one of the first reflector, the second reflector, the third reflector, and/or the fourth reflector may be shaped, in cross-section, generally as at least a portion of an ellipse. In a detailed embodiment, one of the first infrared lamp, second infrared lamp, third infrared lamp, and/or fourth infrared lamp may be located proximate a first foci of the ellipse and/or at least a portion of at least one of the first flow channel, the second flow channel, the third flow channel, and/or the fourth flow channel may be located proximate a second foci of the ellipse.

In an aspect, a surgical fluid management system may include a heater assembly including elongated infrared lamps located adjacent to a slot; a heating cartridge incorporating a three-dimensional fluid path including a plurality of fluid channels, the heating cartridge being receivable within the slot such that the elongated infrared lamps are disposed generally adjacent to the fluid channels; and a control system operatively connected to the elongated infrared lamps, the control system being configured to adjust power to the elongated infrared lamps based on fluid temperature and flow rate to heat the fluid to a desired temperature.

In a detailed embodiment, the control system may be operative to adjust power to the elongated infrared lamps using pulse width modulation. In a detailed embodiment, the heater assembly may include an individual elongated infrared lamp located generally adjacent to each of the fluid channels. In a detailed embodiment, each individual elongated infrared lamp may be mounted generally parallel to its respective fluid channel. In a detailed embodiment, the control system may be configured to supply different levels of power to different lamps, thereby applying different levels of power to different fluid channels in response to fluid temperature and flow rate conditions.

In a detailed embodiment, a surgical fluid management system may include at least one reflector arranged to direct infrared energy emitted by at least one of the elongated infrared lamps towards at least one of the fluid channels. In a detailed embodiment, the at least one reflector may be arranged to minimize exposure of portions of the heating cartridge other than the fluid channels. In a detailed embodiment, the at least one reflector may be integrated with the elongated lamp. In a detailed embodiment, the at least one reflector may include a reflector shroud mounted generally adjacent to the elongated infrared lamp.

In an aspect, a surgical fluid management system may include a heater assembly including a slot including a first side and a second side, a first elongated infrared lamp mounted generally adjacent to the first side of the slot, a second elongated infrared lamp mounted generally adjacent to the second side of the slot, a third elongated infrared lamp mounted generally adjacent to the second side of the slot, a fourth elongated infrared lamp mounted generally adjacent to the first side of the slot; a heating cartridge receivable within the slot and including a first fluid channel and a second fluid channel arranged such that when the heating cartridge is received within the slot, the first fluid channel may be disposed between the first elongated infrared lamp and the second elongated infrared lamp and/or the second fluid channel may be disposed between the third elongated infrared lamp and the fourth elongated infrared lamp; and a control system configured to independently control at least a first group including the first elongated infrared lamp and the second elongated infrared lamp and a second group including the third infrared lamp and the fourth infrared lamp, so as to selectively apply different levels of power to the first fluid channel and the second fluid channel.

In a detailed embodiment, the control system may be operative to selectively apply different levels of power to the first fluid channel and the second fluid channel based at least in part upon fluid temperature and/or flow rate.

In an aspect, a heating cartridge for a surgical fluid management system may include a three-dimensional fluid path including a plurality of fluid channels, each of the plurality of fluid channels being exposed to an exterior of the heating cartridge to receive infrared energy therein. A first one of the fluid channels may be disposed adjacent to a second one of the fluid channels to permit heat transfer from the first fluid channel to the second channel through an interposing wall.

In an aspect, a heating cartridge for a surgical fluid management system may include a substantially rigid main body at least partially defining at least one fluid channel; and a substantially flexible side sheet affixed to the main body, the side sheet at least partially defining the at least one fluid channel, such that the main body and side sheet together define the at least one fluid channel.

In a detailed embodiment, the side sheet may be sufficiently flexible to substantially dampen pulsatile fluid flow through the fluid channel. In a detailed embodiment, the side sheet may be sufficiently flexible to substantially dampen pulsatile fluid flow produced by at least one of a peristaltic pump or a piston pump.

In an aspect, a surgical fluid management system may include a heater assembly including a slot and a heater assembly pressure sensor fitting; a heater cartridge receivable within the slot, the heater cartridge including a heater cartridge pressure sensor fitting configured to couple with the heater assembly pressure sensor fitting upon insertion of the heater cartridge into the heater assembly, the heater cartridge pressure sensor fitting being fluidicly connected to at least one fluid channel within the heater cartridge; and at least one fluid pressure sensor fluidicly connected to the heater assembly pressure sensor fitting, the pressure sensor being operative to measure a pressure of a column of air trapped between fluid in the at least one fluid channel and the pressure sensor.

In an aspect, a method of operating a surgical fluid management system may include delivering fluid to a surgical site via a heater assembly, the heater assembly including at least a first heater and a second heater, the fluid flowing past the first heater and then flowing past the second heater; supplying power to the first heater based at least in part upon an estimated power requirement, the estimated power requirement being substantially proportional to a flow rate of the fluid and a total desired temperature change of the fluid; and supplying power to the second heater, including, if a current outlet temperature is less than a set point outlet temperature by greater than a predetermined threshold, supplying power to the second heater based upon a first heater control algorithm, and, if the current outlet temperature is less than the set point outlet temperature by less than a predetermined threshold, supplying power to the second heater based upon a second heater control algorithm.

In a detailed embodiment, supplying power to the first heater may include supplying power to the first heater based at least in part upon a load factor multiplied by the estimated power requirement. In a detailed embodiment, supplying power to the second heater may include cutting off power to the second heater if a predetermined threshold rate of pressure increase is reached.

In a detailed embodiment, the first heater control algorithm may include a proportional control algorithm, the proportional control algorithm including multiplying the estimated power requirement by a proportional control factor, the proportional control factor varying with the temperature error, the temperature error being a difference between a set point outlet temperature and a current outlet temperature. In a detailed embodiment, the proportional control factor may be given by $$k_1 + \frac{\text{temperature\_error}^2}{k_2},$$

where $k_1$ and $k_2$ are constants.

In a detailed embodiment, the second heater control algorithm may include an integral control algorithm, the integral control algorithm including calculating an integral of the temperature error over time, the temperature error being a difference between a set point outlet temperature and a current outlet temperature; if the integral of the temperature error over time is less than a predetermined negative value, incrementally reducing the power supplied to the second heater; if the integral of the temperature error over time is greater than a predetermined positive value, incrementally increasing the power supplied to the second heater; and if the integral of the temperature error over time is between the predetermined negative value and the predetermined positive value, maintaining the power supplied to the second heater.

In a detailed embodiment, incrementally reducing the power supplied to the second heater and incrementally increasing the power supplied to the second heater may include adjusting the power supplied to the second heater in increments of about 1% of a maximum power of the second heater. In a detailed embodiment, supplying power to the second heater based upon the integral control algorithm may include applying a reduction factor to the power supplied to the second heater, the reduction factor decreasing from about 1.0 to about 0 as the current outlet temperature increases to reach and exceed the set point outlet temperature.

In an aspect, a method of monitoring a fluid deficit in a surgical fluid management system may include measuring an initial weight held by a fluid supply container support, the fluid supply container support supporting a first fluid supply container; measuring an initial weight held by a fluid collection container support, the fluid collection container support supporting a first fluid collection container; calculating an initial reference total weight, the initial reference total weight including a sum of the initial fluid supply container support weight and the initial fluid collection container support weight; supplying fluid from the first fluid supply container to a surgical site; collecting at least some of the fluid from the surgical site into the first fluid collection container; measuring a first current weight held by the fluid supply container support; measuring a first current weight held by the fluid collection container support; calculating a first current total weight, the first current total weight including a sum of the first current weight held by the fluid supply container support and the first current weight held by the fluid collection container support; and calculating a first fluid deficit by subtracting the first current total weight from the initial reference total weight.

In a detailed embodiment, a method may include, prior to measuring the initial weight held by the fluid supply container support and prior to measuring the initial weight held by the fluid collection container support, priming a tubing set.

In a detailed embodiment, a method may include, after calculating the first fluid deficit, supplying fluid from the first fluid supply container to the surgical site and collecting at least some of the fluid from the surgical site into the first collection container; measuring a second current weight held by the fluid supply container support; measuring a second current weight held by the fluid collection container support; calculating a second current total weight, the second current total weight including a sum of the second current weight held by the fluid supply container support and the second current weight held by the fluid collection container support; and calculating a second fluid deficit by subtracting the second current total weight from the initial reference total weight.

In a detailed embodiment, a method may include, after calculating the second fluid deficit, accounting for replacement of the first fluid supply container with a second fluid supply container by prior to replacement of the first fluid supply container with the second fluid supply container, measuring a pre-replacement weight held by the fluid supply container support; after replacement of the first fluid supply container by the second fluid supply container, measuring a post-replacement weight held by the fluid supply container support; calculating a fluid supply container weight difference by subtracting the pre-replacement weight from the post-replacement weight; and calculating an updated reference total weight, the updated reference total weight including the sum of the initial reference total weight and the fluid supply container weight difference.

In a detailed embodiment, a method may include, after calculating the updated total reference weight, supplying fluid from the second fluid supply container to the surgical site and collecting at least some of the fluid from the surgical site into the first collection container; measuring a third current weight held by the fluid supply container support; measuring a third current weight held by the fluid collection container support; calculating a third current total weight, the third current total weight including a sum of the third current weight held by the fluid supply container support and the third current weight held by the fluid collection container support; and calculating a third fluid deficit by subtracting the third current total weight from the updated reference total weight.

In a detailed embodiment, a method may include detecting replacement of the first fluid supply container by the second fluid supply container by ascertaining a substantial weight difference between the pre-replacement weight and the post-replacement weight. In a detailed embodiment, the substantial weight difference may correspond approximately to a predetermined expected fluid supply container replacement weight difference. In a detailed embodiment, ascertaining the substantial difference may include waiting for a period of time to allow dissipation of transient weight signals present due to inadvertent motion of the surgical fluid management system. In a detailed embodiment, detecting replacement of the first fluid supply container by the second fluid supply container may include detecting replacement of a partially depleted first fluid supply container by a substantially full second fluid supply container.

In a detailed embodiment, a method a method may include, after calculating the second fluid deficit, accounting for replacement of the first fluid collection container with a second fluid collection container by prior to replacement of the first fluid collection container with the second fluid collection container, measuring a pre-replacement weight held by the fluid collection container support; after replacement of the first fluid collection container by the second fluid collection container, measuring a post-replacement weight held by the fluid collection container support; calculating a fluid collection container weight difference by subtracting the pre-replacement weight from the post-replacement weight; and calculating an updated reference total weight, the updated reference total weight including the sum of the initial reference total weight and the fluid collection container weight difference.

In a detailed embodiment, a method may include, after calculating the updated total reference weight, supplying fluid from the first fluid supply container to the surgical site and collecting at least some of the fluid from the surgical site into the second collection container; measuring a third current weight held by the fluid supply container support; measuring a third current weight held by the fluid collection container support; calculating a third current total weight, the third current total weight including a sum of the third current weight held by the fluid supply container support and the third current weight held by the fluid collection container support; and calculating a third fluid deficit by subtracting the third current total weight from the updated reference total weight.

In a detailed embodiment, a method may include detecting replacement of the first fluid collection container by the second fluid collection container by ascertaining a substantial weight difference between the pre-replacement weight and the post-replacement weight. In a detailed embodiment, the substantial weight difference may correspond approximately to a predetermined expected fluid collection container replacement weight difference.

In an aspect, a method of monitoring a fluid deficit in a surgical fluid management system may include measuring an initial weight held by a fluid supply container support, the fluid supply container support supporting at least one fluid supply container; measuring an initial weight held by a fluid collection container support, the fluid collection container support supporting at least one fluid collection container; calculating an initial reference total weight, the initial reference total weight including a sum of the initial fluid supply container support weight and the initial fluid collection container support weight; supplying fluid from the at least one fluid supply container to a surgical site; collecting at least some of the fluid from the surgical site into the at least one fluid collection container; monitoring a current weight held by the fluid supply container support; monitoring a current weight held by the fluid collection container support; calculating a current total weight, the current total weight including a sum of the current weight held by the fluid supply container support and the current weight held by the fluid collection container support; and calculating a current fluid deficit by subtracting the current total weight from the initial reference total weight.

In a detailed embodiment, a method may include accounting for replacement of the at least one fluid supply container with a new fluid supply container including sensing a significant difference between a pre-replacement fluid supply container support weight and a post-replacement fluid supply container support weight; calculating a fluid supply container weight difference by subtracting the pre-replacement fluid supply container support weight from the post-replacement fluid supply container support weight; calculating an updated reference total weight, the updated reference total weight including the sum of the initial reference total weight and the fluid supply container weight difference; and using the updated reference total weight in subsequent deficit calculations.

In a detailed embodiment, a method may include accounting for replacement of the at least one fluid collection container with a new fluid collection container including sensing a significant difference between a pre-replacement fluid collection container support weight and a post-replacement fluid collection container support weight; calculating a fluid collection container weight difference by subtracting the pre-replacement fluid collection container support weight from the post-replacement fluid collection container support weight; calculating an updated reference total weight, the updated reference total weight including the sum of the initial reference total weight and the fluid collection container weight difference; and using the updated reference total weight in subsequent deficit calculations.

In a detailed embodiment, a method may include repeating the monitoring the current weight held by the fluid supply container support, monitoring the current weight held by the fluid collection container support, calculating the current total weight, and calculating the current fluid deficit operations to provide a substantially continuously updated fluid deficit calculation.

In an aspect, a method of operating a surgical fluid management device may include calculating an initial reference total weight, the initial reference total weight including a sum of an initial weight of a fluid supply container and an initial weight of a fluid collection container; supplying fluid from the fluid supply container to a surgical site; collecting at least some of the fluid from the surgical site into the fluid collection container; calculating a current total weight, the current total weight including a sum of a current weight of the fluid supply container and a current weight of the fluid collection container; and calculating a deficit by subtracting the current total weight from the initial reference total weight.

In a detailed embodiment, a method may include detecting replacement of the fluid supply container by a replacement fluid supply container by ascertaining a substantial weight difference between a pre-replacement weight of the fluid supply container and a post-replacement weight of the replacement fluid supply container; calculating an updated reference total weight, the updated reference total weight including the sum of the initial reference total weight and a difference between the post-replacement weight of the replacement fluid supply container and the pre-replacement weight of the fluid supply container.

In a detailed embodiment, a method may include supplying fluid from the replacement fluid supply container to the surgical site; collecting at least some of the fluid from the surgical site into the fluid collection container; calculating an updated current total weight, the updated current total weight including a sum of an updated current weight of the replacement fluid supply container and an updated current weight of the fluid collection container; and calculating an updated deficit by subtracting the updated current total weight from the updated reference total weight.

In a detailed embodiment, a method may include detecting replacement of the fluid collection container by a replacement fluid collection container by ascertaining a substantial weight difference between a pre-replacement weight of the fluid collection container and a post-replacement weight of the replacement fluid collection container; and calculating an updated reference total weight, the updated reference total weight including the sum of the initial reference total weight and a difference between the post-replacement weight of the replacement fluid collection container and the pre-replacement weight of the fluid collection container.

In a detailed embodiment, a method may include supplying fluid from the fluid supply container to the surgical site; collecting at least some of the fluid from the surgical site into the replacement fluid collection container; calculating an updated current total weight, the updated current total weight including a sum of an updated current weight of the fluid supply container and an updated current weight of the replacement fluid collection container; and calculating an updated deficit by subtracting the updated current total weight from the updated reference total weight.

In an aspect, a method of operating a multi-functional fluid management system may include receiving, via a user interface, at least one of a surgical discipline selection and a surgical procedure selection; and setting at least one default operating limit based at least in part upon the at least one of the surgical discipline selection and the surgical procedure selection.

In a detailed embodiment, a method may include allowing user-directed operation below the default operating limit; requiring additional affirmative action via the user interface for operation above the default operating limit at less than a maximum limit; and precluding operation above the maximum limit.

In an aspect, a method of operating a surgical fluid management system may include receiving, via a user interface, identification of information to be gathered by a surgical fluid management system during a surgical procedure; electronically storing the information during the surgical procedure; and receiving, via the user interface, an instruction pertaining to at least one of printing, storing, and/or electronically transmitting the information.

In an aspect, a method of operating a multi-functional surgical fluid management system may include receiving, via a user interface, identification of at least one of a surgical discipline and a surgical procedure; setting default operating parameters based upon the at least one of the surgical discipline and the surgical procedure and receiving, via a user interface, input to adjust the operating parameters.

In a detailed embodiment, a method may include receiving, via the user interface, input pertaining to desired alarm levels and alarm types; and overriding an alarm received during the surgical procedure based on input received via the user interface, if conditions have not exceeded pre-established maximum levels.

In a detailed embodiment, the alarm types may include at least one of visible and audible.

In an aspect, a method of operating a surgical fluid management system may include receiving, via a user interface, preferred operating settings associated with at least one of a surgical discipline and a surgical procedure, the preferred operating settings also being associated with an identity of at least one of a surgeon and an operator; and setting operating parameters at the preferred operating settings upon receiving an input, via a user interface, associated with at least one of the surgeon and the operator and at least one of the surgical discipline and the surgical procedure.

In an aspect, a surgical fluid management system may include a touch screen interface, the touch screen interface being configured to receive user input pertaining to operating parameters and to display information.

In an aspect, a method of controlling a surgical fluid management device may include receiving, via a user input, identification of information which must be entered prior to operation of a surgical fluid management device; requesting entry of the information; if the information has not been entered, precluding operation of the of the surgical fluid management device; and if the information has been entered, allowing operation of the surgical fluid management device.

In accordance with another aspect of the present invention, there is provided a fluid management system for supplying fluids of at least two types, said system comprising: at least one fluid supply container; at least one fluid collection container; a pump configured to deliver a fluid from the at least one fluid supply container to a site, said site being a surgical site or a patient; a control system for operating the fluid management system in at least one of (1) a pressure control mode, wherein said control system controls the pump to deliver fluid to the site at approximately a target pressure or (2) a flow control mode, wherein the control system controls the pump to deliver fluid to the site at approximately a target flow rate. The control system includes a user interface for communication between the control system and a user, including inputting data to the control system and outputting data from the control system; a fluid deficit monitoring function for determining a fluid deficit that is a difference between (i) a volume of fluid delivered to the site from the at least one fluid supply container and (ii) a volume of fluid returned from the site to the at least one fluid collection container; and a fluid deficit alarm function for activating a fluid deficit alarm when a fluid deficit exceeds a fluid deficit alarm limit indicative of a maximum fluid deficit associated with a type of fluid communicated to the control system.

In accordance with still another aspect of the present invention, there is provided a method of operating a fluid management system for supplying fluids of at least two types, wherein said system includes at least one fluid supply container, at least one fluid collection container, a pump configured to deliver a fluid from the at least one fluid supply container to a site, said site being a surgical site or a patient; and a control system for controlling operation of the fluid management system. The method includes the steps of: inputting data to the control system and outputting data from the control system via a user interface; selecting a medical procedure that requires (1) a pressure control mode, wherein said control system controls the pump to deliver fluid to the site at approximately a target pressure or (2) a flow control mode, wherein said control system controls the pump to deliver fluid to the site at approximately a target flow rate; determining a fluid deficit that is a difference between (i) a volume of fluid delivered to the site from the at least one fluid supply container and (ii) a volume of fluid returned from the site to the at least one fluid collection container; associating a fluid deficit alarm limit with a type of fluid being supplied by the at least one fluid supply container; and activating a fluid deficit alarm when the fluid deficit exceeds the fluid deficit alarm limit associated with the type of fluid being supplied by the at least one fluid supply container.

BRIEF DESCRIPTION OF THE DRAWINGS

The detailed description refers to the following figures in which.

DETAIL DESCRIPTION OF THE INVENTION

Figure 1:
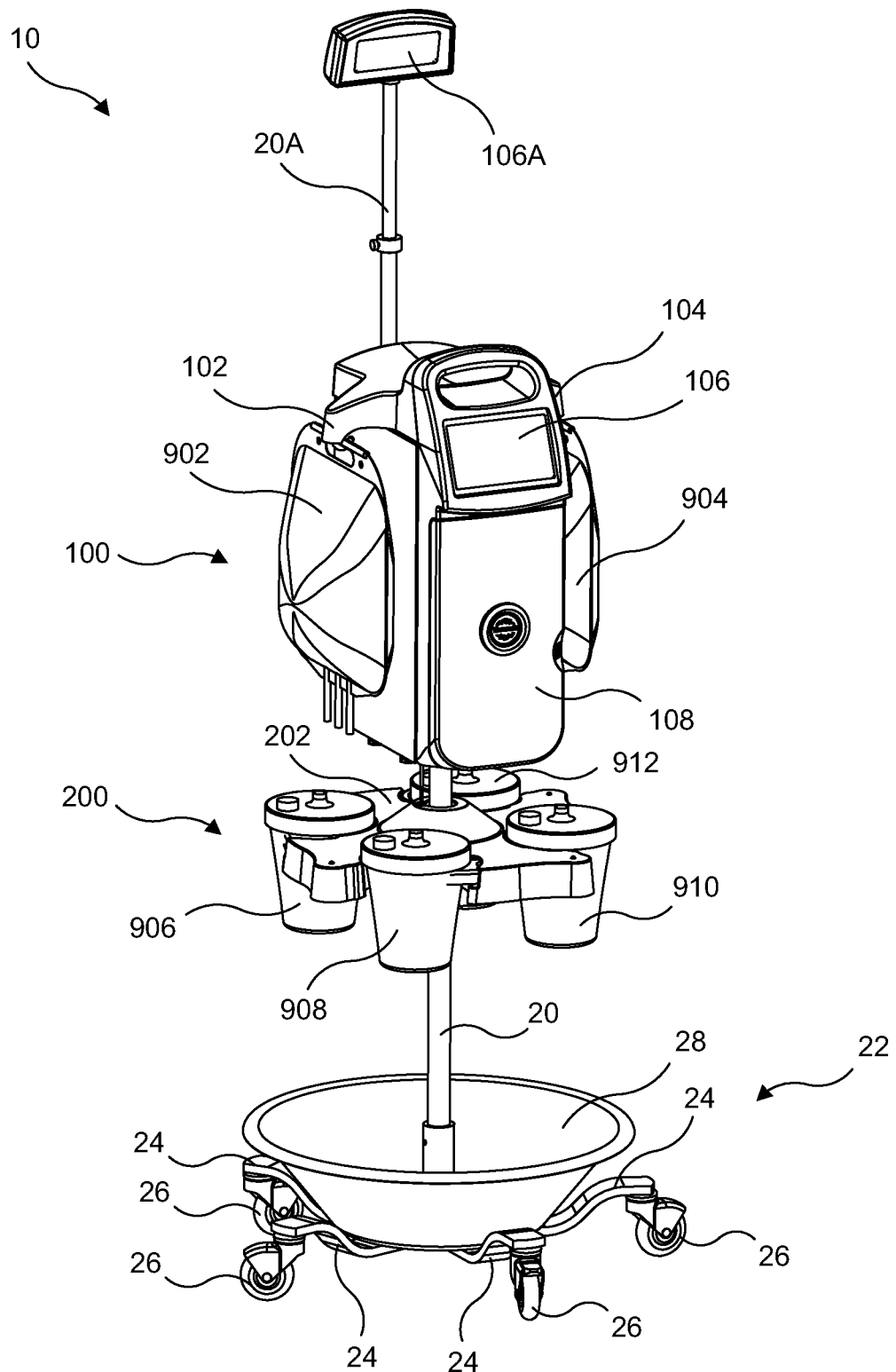
FIG. 1 is a perspective view of an exemplary surgical fluid management system.

The present disclosure includes, inter alia, surgical fluid management systems and methods for using surgical fluid management systems.

The present disclosure contemplates that various fluids (such as irrigation fluids) may be employed during surgical procedures for many purposes, such as (and without limitation) to wash away blood and/or debris from a surgical site to provide the surgeon with an improved view and/or to distend a surgical site (such as during some gynecological, urological, and orthopedic procedures, for example). In addition, the present disclosure contemplates that fluids may be infused into a patient. For example, various fluids (including fluids comprising pharmaceuticals and/or blood components) may be intravenously infused into a patient.

Further, the present disclosure contemplates that a patient's core body temperature may be reduced if a low-temperature irrigation and/or infusion fluid is employed. Thus, the use of low-temperature fluids (which may refer to fluids at temperatures less than a patient's body temperature) may contribute to hypothermia, which may be a reduction in a patient's body temperature of about 2° C. or more. For example, the use of low-temperature irrigation fluid during a surgical procedure may contribute to intraoperative hypothermia. Similarly, the present disclosure contemplates that infusion of low temperature fluids may contribute to patient hypothermia. The present disclosure contemplates that hypothermia may result in adverse patient outcomes and/or increased medical costs. Similarly, the present disclosure contemplates that some procedures may include intentionally lowering a patient's body temperature, and, in such circumstances, further lowering of the patient's body temperature below the desired temperature may result in adverse patient outcomes and/or increased medical costs.

An exemplary fluid management system according to the present disclosure may provide one or more functions, including irrigation, distention, deficit monitoring, and/or infusion functions, and/or may warm the fluid. An exemplary embodiment may allow a user to select between fluid pressure or flow rate control, to enable or disable fluid warming, to control various operating parameters (such as desired fluid pressure or fluid flow rate, fluid temperature (if the fluid warming feature is enabled), and the like), may display information (such as desired and/or actual fluid pressure, fluid flow rate, and fluid temperature, as well as fluid volume, volumetric deficit, and the like), and/or may provide one or more alarms (such as an over pressure alarm, over temperature alarm, low fluid supply alarm, fluid deficit alarm, perforation alarm, and the like). Some exemplary devices may provide data logging and/or printing capabilities and/or the ability to electronically transmit data to a central data collection or information system. An exemplary embodiment may warm a fluid to a temperature selected by a user (such as a temperature approximate a patient's body temperature) and/or may deliver the fluid to the surgical site at a pressure and/or flow rate selected by a user.

FIG. 1 is a perspective view of an exemplary fluid management system 10 including a fluid management unit 100. An exemplary fluid management unit 100 may include one or more fluid container supports, such as fluid bag hangers 102, 104, each of which may support one or more fluid bags 902, 904 (and/or other fluid supply containers). Fluid bag hangers 102, 104 may receive a variety of sizes of fluid bags 902, 904, such as 1 L to 5 L bags. An exemplary embodiment may include fluid bag hangers 102, 104 at approximately shoulder height, which may minimize the difficulty of hanging fluid bags 902, 904, particularly when large volume fluid bags 902, 904 are employed.

An exemplary fluid management unit 100 may include one or more user interface components, such as a touch screen display 106. As will be described in detail below, the user interface provides communication between a control system and a user, including inputting data to the control system and outputting data from the control system. The user interface may provide information to the user in visual and/or audible forms. Some exemplary embodiments may employ switches, knobs, dials, and the like as user interface components in addition to or instead of one or more touch screen displays 106. User interface components, such as touch screen display 106, may enable the user to select fluid pressure or flow rate control, to enable or disable fluid warming functions, to configure operating parameters and alarms, to configure information to be displayed, and/or to configure information to be stored, printed, or transmitted after the procedure for record keeping purposes.

An exemplary fluid management system 10 may include a secondary display 106A, which may be mounted to a display pole 20A. Display pole 20A may be configured to be extendable (e.g., telescopically) to allow adjustment of the height of secondary display 106A. Such an embodiment may be useful during procedures in which the surgeon is sitting and/or must look over an obstruction to view the fluid management system 10. Similarly, some exemplary embodiments may include one or more remote displays which may be located away from the fluid management unit 100 for the convenience of a user.

Some exemplary fluid management units 100 may include a door 108 or other closure which may at least partially cover various components. In some exemplary embodiments including a door 108 or other closure, the position (e.g., shut and/or open) of the door 108 or other closure may be utilized as an interlock to prevent and/or allow certain operations of the device.

An exemplary fluid management system 10 may include a suction container hanger assembly 200. An exemplary suction container hanger assembly 200 may support one or more suction canisters 906, 908, 910, 912 (and/or other fluid collection containers) from a suction canister hanger 202. Other exemplary embodiments may employ suction container support assemblies other than suspension-type assembles. For example, an assembly supporting a suction container from below may be utilized instead of or in addition to a suspension-type assembly. In an exemplary embodiment, one or more suction canisters 906, 908, 910, 912 may be coupled to a suction or vacuum source, such as any of those commonly found in a surgical suite. An exemplary suction container hanger assembly 200 may be adapted to accommodate different sizes of suction containers and may be adjustable to accommodate such containers.

An exemplary surgical fluid management unit 100 may be mounted on a rolling stand, which may include a pole 20 and/or a base 22, which may include a plurality of castered wheels 26 mounted to a respective plurality of legs 24. The base 22 may also include a storage basket 28 other similar storage component. Some exemplary embodiments may be mounted to other mobile devices, such as a cart. Some exemplary embodiments may be mounted in a fixed location, such as an operating room, by being affixed to a wall, mounted to other fixed equipment, mounted on a boom, etc.

An exemplary fluid management unit 100 may be utilized with tubing sets that fluidicly connect various components. Tubing sets may be disposable (to comply with health standards associated with items contacting bodily fluids, for example), and may be provided sterile and ready for use. Different tubing sets may be utilized for performing different surgical functions. For example, an exemplary irrigation tubing set for laparoscopic procedures may include generally parallel suction and irrigation tubing, and/or may include a valve device (such as a trumpet valve) for controlling flow of irrigation fluid and/or suction. An exemplary tubing set for distention procedures may include generally parallel delivery and return tubing, which may couple to a surgical instrument, such as via standard Luer-lock fittings. Such tubing sets for distention procedures may incorporate a pressure relief valve to guard against over-pressurization of the body cavity being distended.

Figure 2:
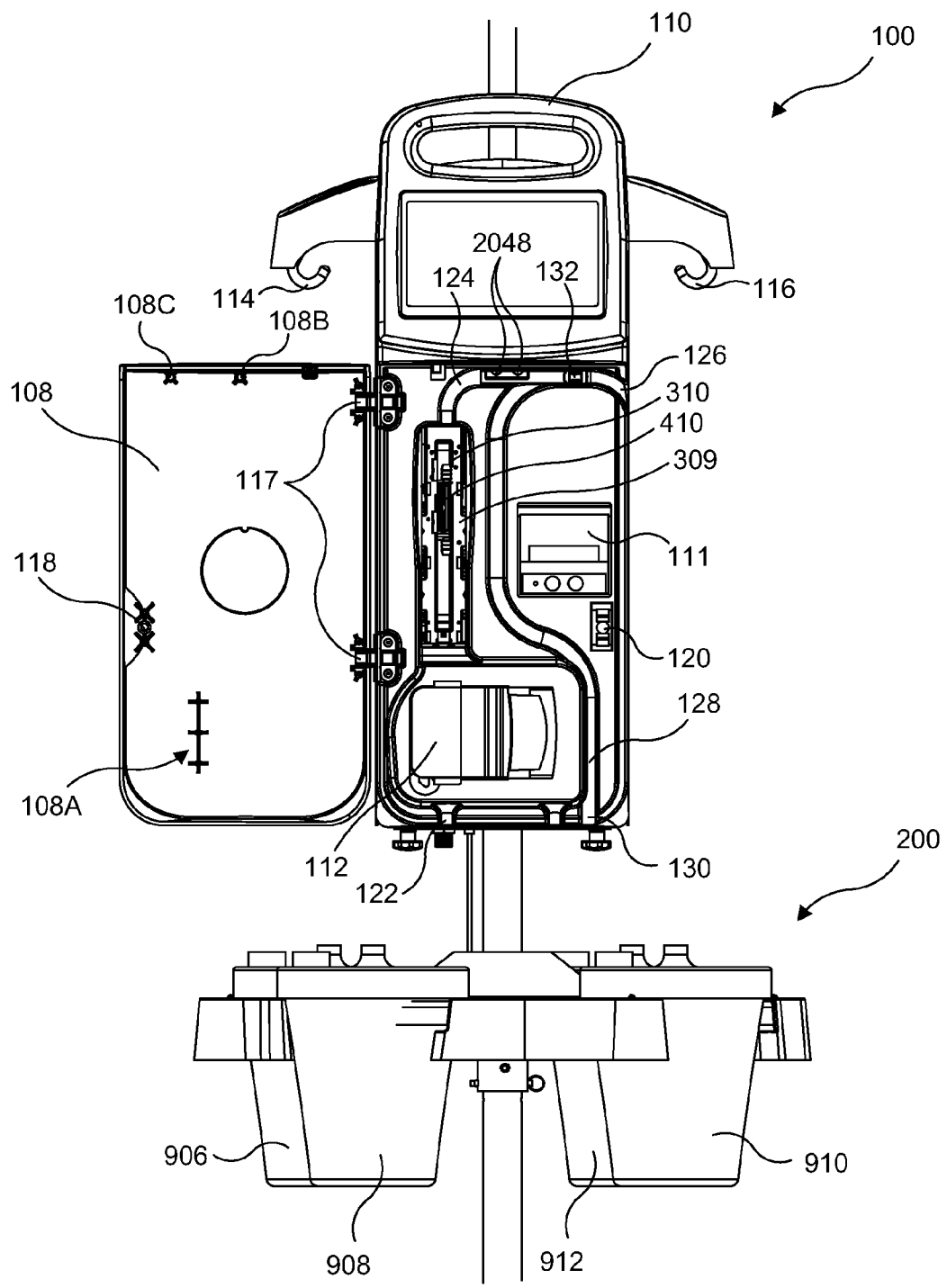
FIG. 2 is a front elevation view of an exemplary surgical fluid management system with the door open.

FIG. 2 is a detailed front elevation view of an exemplary fluid management unit 100. In FIG. 2, door 108 is open and slot 310 for fluid heating cartridge 410 is visible. An exemplary cartridge 410, described in further detail below, may be utilized with one or more heat transfer devices (e.g., heaters) to change the temperature of a fluid prior to delivery to a surgical site and/or prior to infusion into a patient. In an exemplary embodiment, cartridge 410 may be fully enclosed (except for the connections described below) and/or may be provided as part of a disposable tubing set. By providing a disposable cartridge 410 (and/or other patient or fluid-contacting components) as part of a disposable tubing set, an exemplary fluid management system 10 may provide components requiring sterilization prior to use and/or which may contact bodily fluids as disposable components, and/or other components may be durable. Thus, only minimal cleaning of the non-disposable components of fluid management system 10 may be required between patients.

An exemplary embodiment may include a data recording device, such as a printer 111. An exemplary data recording device may create a permanent and/or temporary record of important information regarding the use of the fluid management system 10 during a surgical procedure, such as the identity of the surgeon, identity of the operator, identity of the patient (usually by patient number), procedure performed, and procedure duration, as well as various operating conditions such as total fluid volume utilized, average fluid temperature, minimum and/or maximum fluid temperatures, alarm conditions, and the like. Those of ordinary skill will recognize that alternate and/or additional data recording and/or storage mechanisms may be utilized, such as electronic storage components.

An exemplary fluid management unit 100 may include a handle 110.

An exemplary fluid management unit 100 may include one or more fluid pressurization or transfer devices, such as a pump 112. An exemplary pump 112 may include an electrically driven peristaltic pump. Some exemplary peristaltic pumps may operate at speeds between about 4 and 400 revolutions per minute and/or may deliver fluid up to approximately 1.4 L/min, for example. Some exemplary embodiments may include other types of positive displacement and/or non-positive displacement pumps known in the art. Further, some exemplary embodiments may utilize alternative power sources, such as compressed air, vacuum, etc. to drive a pump. Exemplary electrically driven pumps may receive power from a line source (such as a wall outlet) and/or one or more external and/or internal electrical storage devices (such as a disposable or rechargeable battery). Some exemplary electrically driven pumps may include stepper motors, DC brush motors, AC or DC brushless motors, and/or other similar devices known in the art.

In an exemplary embodiment, fluid bag hangers 102, 104 may include one or more hooks 114, 116 from which one or more fluid bags 902, 904 may be suspended. In an exemplary embodiment, door 108 may include one or more hinges 117 and/or a latch component 118, which may have a corresponding latch component 120 on the fluid management unit 100.

Various fluid paths are visible in FIG. 2. For example, a tubing set may include irrigation tubing, which may include tubing extending from one or more fluid containers (such as fluid bags 902, 904 shown in FIG. 1), through opening 122, through pump 112, into cartridge 410 (which may be provided as part of the tubing set), out of the cartridge into path 124, and to a hand piece via opening 126. A tubing set may include suction tubing, which may include tubing extending from a hand piece into opening 126, through path 128, out of opening 130, and to one or more suction sources and/or containers, such as suction canisters 906, 908, 910, 912.

Some exemplary embodiments may include one or more bubble detectors, such as ultrasonic bubble detector 132, which may be provided along a fluid path. Exemplary embodiments may include other types of bubble detectors and/or liquid detectors (such as optical bubble detectors, infrared bubble detectors, and the like) in place of or in addition to ultrasonic bubble detector 132. One or more bubble detectors 132 may be utilized for various purposes as discussed below, such as to detect liquid during priming and/or to detect a bubble in tubing leading to a surgical and/or infusion site. In some exemplary embodiments, one or more bubble detectors 132 may be used to detect fluid within the tubing, thus indicating that cartridge 410 may be substantially filled with fluid and, therefore, heater assembly 309 may be safely activated, In some exemplary embodiments, two or more bubble detectors 132 may be utilized to detect bubbles (e.g., in distention and/or infusion applications), which may provide redundant bubble detection capability. For example, in some distention and/or infusion applications, if any bubble detector 132 detects a bubble, pump 112 may be stopped to reduce the risk of introducing air into the body cavity being distended (which could obstruct viewing) or infusing air into a patient.

Some exemplary embodiments may include one or more temperature sensors, such as thermal cut off sensor(s) 2048, which may include one or more bimetal switches, infrared temperature sensors, and/or other temperature sensors known in the art. Bubble detector(s) 132 and thermal cut off sensor(s) 2048 may be mounted such that they may be in contact with tubing extending through path 124, for example.

In some exemplary embodiments, door 108 may be arranged such that it may not be fully shut unless the tubing of the tubing set is properly inserted into the appropriate flow paths. For example, door 108 may be arranged such that it will not fully shut unless cartridge 410 is fully inserted into slot 310 and/or tubing associated with a tubing set is properly installed in fluid management unit 100. Fingers 108A on the inside of door 108 may be configured to prevent door 108 from fully shutting if pump 112 is not in its operational configuration (e.g., door 108 may be prevented from closing if the pump head is not closed). Similarly, finger 108C may be configured to press tubing into path 124 to promote contact between the tubing and bubble detector 132. Likewise, finger 108B may be configured to press tubing into path 124 to promote contact between the tubing and thermal cut off sensor(s) 2048.

Figure 3:
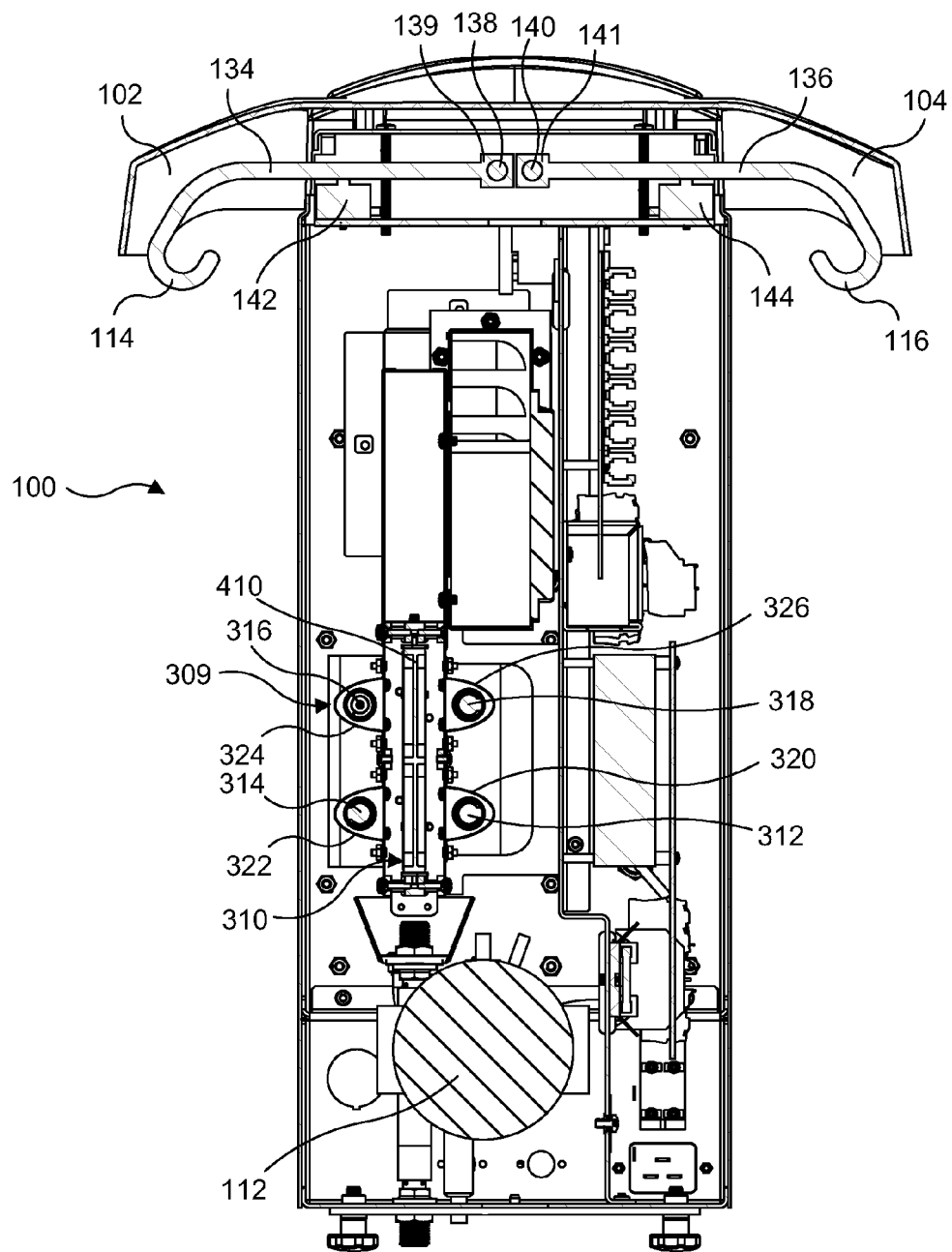
FIG. 3 is a front elevation cross-section view of an exemplary surgical fluid management system.

FIG. 3 is a cross-sectional view of an exemplary fluid management unit 100. Some exemplary fluid bag hangers 102, 104 may include rods 134, 136 which may be pivotably joined at pivots 138, 140, respectively. In an exemplary embodiment, rods 134, 136 may include a journal 139, 141 through which the respective pivot 138, 140 extends. Rods 134, 136 may be supported by one or more load cells 142, 144, which may output electrical signals associated with the weight of the fluid containers suspended from the fluid bag hangers. In an exemplary embodiment, load cells 142, 144 may include button-type compression cells. Other exemplary embodiments may utilize load cells of other types, such as beam-type load cells and/or strain gauges. An exemplary embodiment may utilize a signal provided by one or more load cells 142, 144 to determine a volume of one or more bags of fluid 902, 904 attached to the unit 100 (e.g., whether a given bag of fluid 902 is a 1 L bag, or a 5 L bag), to determine an amount of fluid remaining in one or more bags of fluid 902, 904, and/or to sense when a bag of fluid 902, 904 has been replaced, for example. In an exemplary embodiment in which a fluid bag hanger 102, 104 is utilized to hang a single fluid bag 902, 904, each load cell 142, 144 may provide a signal associated with the weight of a single fluid bag 902, 904.

In some exemplary embodiments, providing one or more integral fluid bag hangers 102, 104 may reduce the complexity and/or cost of the fluid management system 10 because wiring associated with the load cells 142, 144 may be located within the housing of fluid management unit 100, as compared to embodiments including fluid bag hangers mounted to a supporting structure (such a pole and cross bar assembly) extending upwardly from the fluid management unit 100. Specifically, integral fluid bag hangers 102, 104 may obviate the need to run wiring associated with one or more load cells along or within an upwardly extending supporting structure.

In an exemplary embodiment, a heater assembly 309 may include one or more heat sources, such as infrared (IR) lamps 312, 314, 316, 318, which may be mounted near slot 310. In other exemplary embodiments, other sources of IR energy may be utilized, such as halogen lamps, light emitting diodes (LEDs), quartz lamps, carbon lamps, and the like. In an exemplary embodiment, IR lamps 312, 314, 316, 318 may draw up to about 500 W each, for a total of up to approximately 2 kW, which may provide approximately a 25° C. temperature rise (or greater) at a flow rate of approximately 500 mL/min or greater. Reflector shrouds 320, 322, 324, 326 may be mounted to direct IR energy emitted by lamps 312, 314, 316, 318 towards cartridge 410, which may be received in slot 310.

Figure 4:
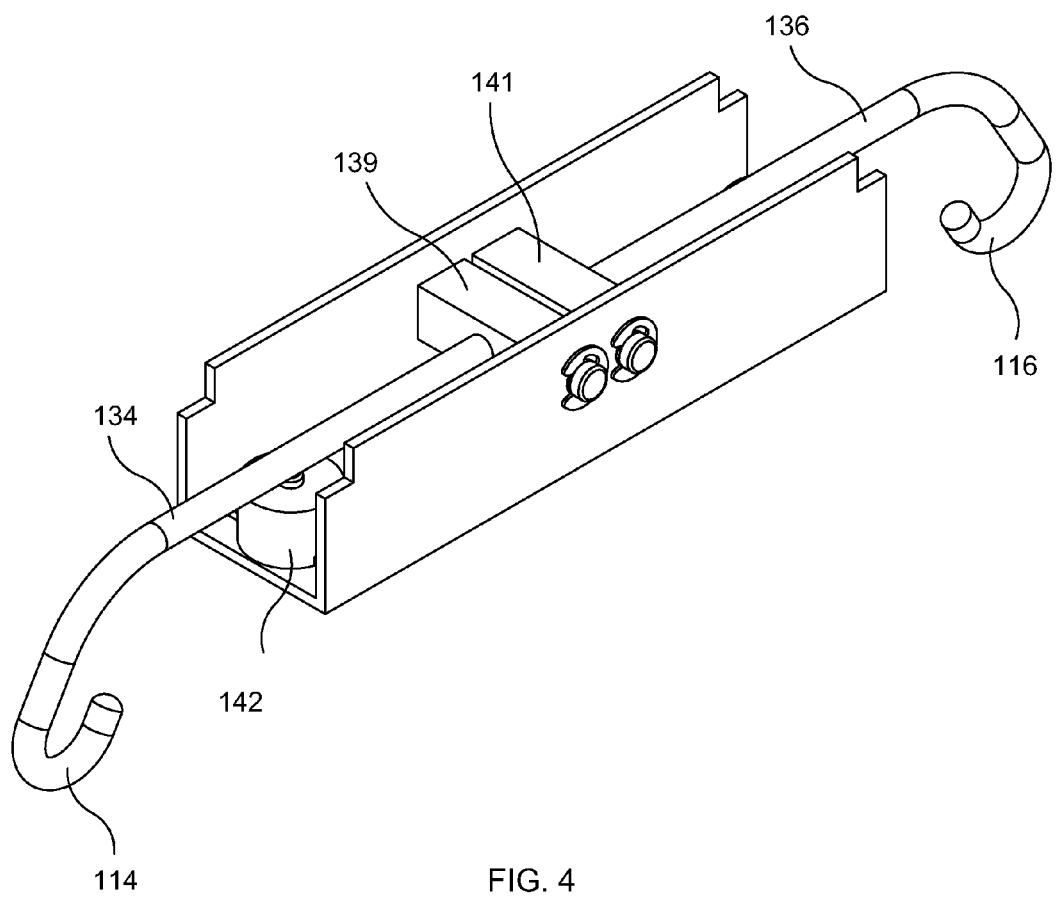
FIG. 4 is a perspective view of an exemplary fluid bag hanger assembly.
Figure 5:
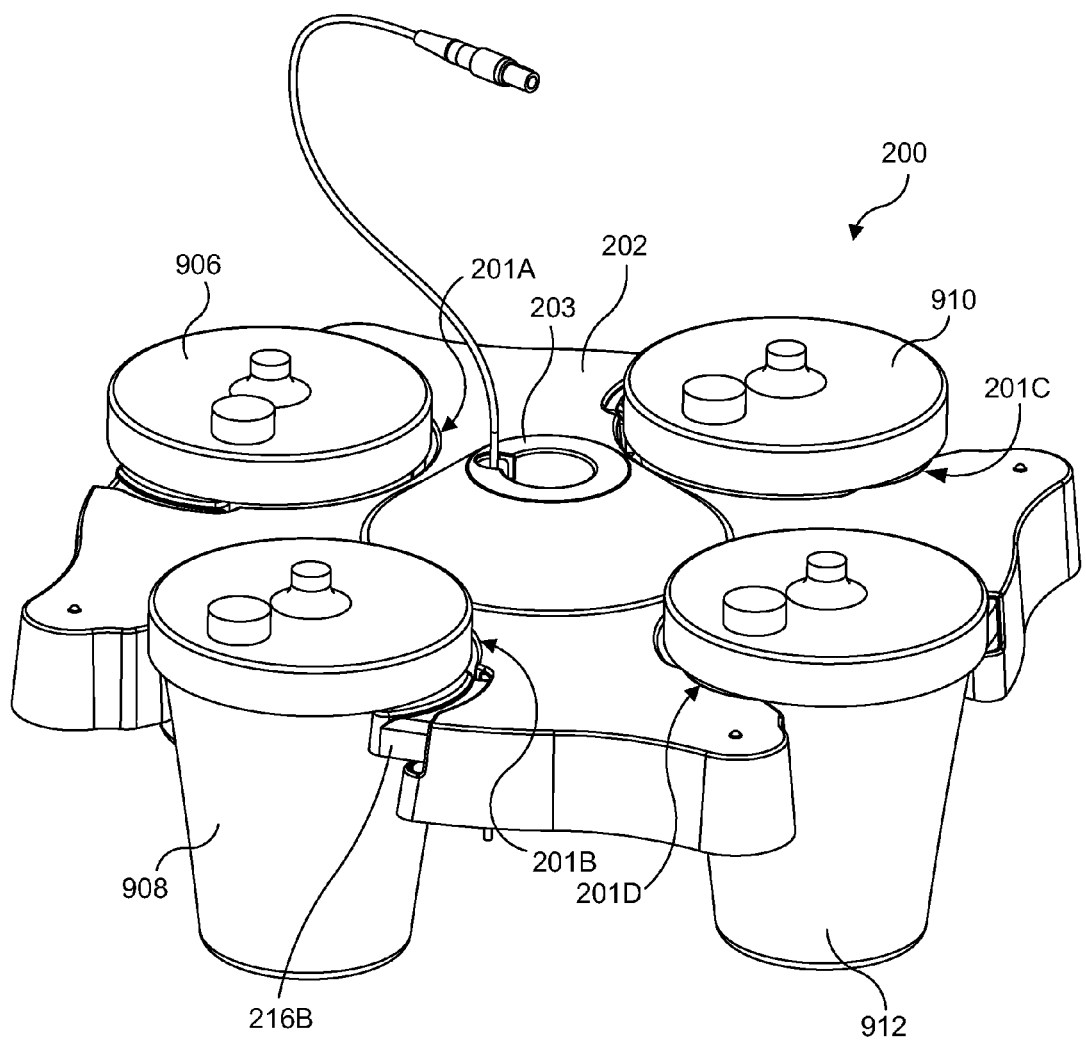
FIG. 5 is a perspective view of an exemplary suction container hanger assembly.
Figure 6:
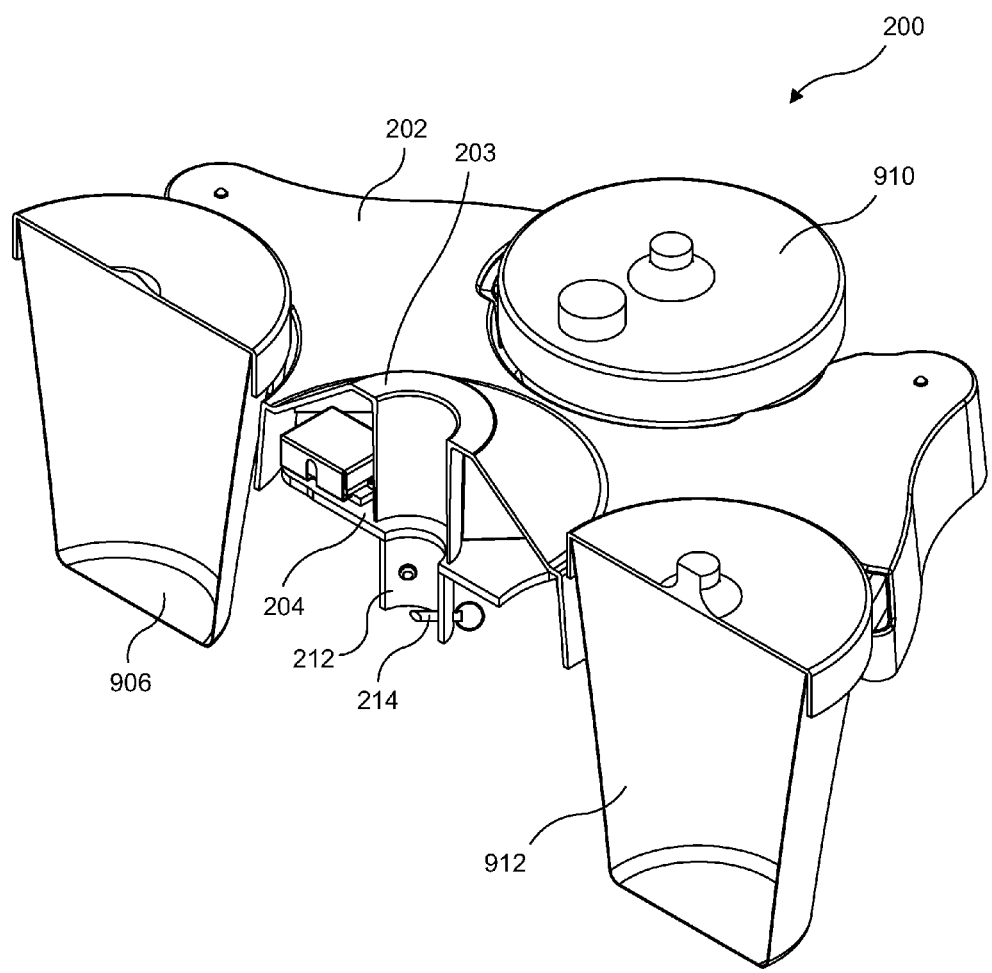
FIG. 6 is a cross-sectional view of an exemplary suction container hanger assembly.

FIG. 4 is a detailed perspective view of an exemplary fluid bag hanger assembly.

FIGS. 5-8 illustrate an exemplary suction container hanger assembly 200. Suction canister hanger 202 may include one or more receiving openings 201A, 201B, 201C, 201D into which one or more suction canisters 906, 908, 910, 912 may be placed. Openings 201A, 201B, 201C, 201D may be adapted to receive suction canisters of various sizes.

Figure 7:
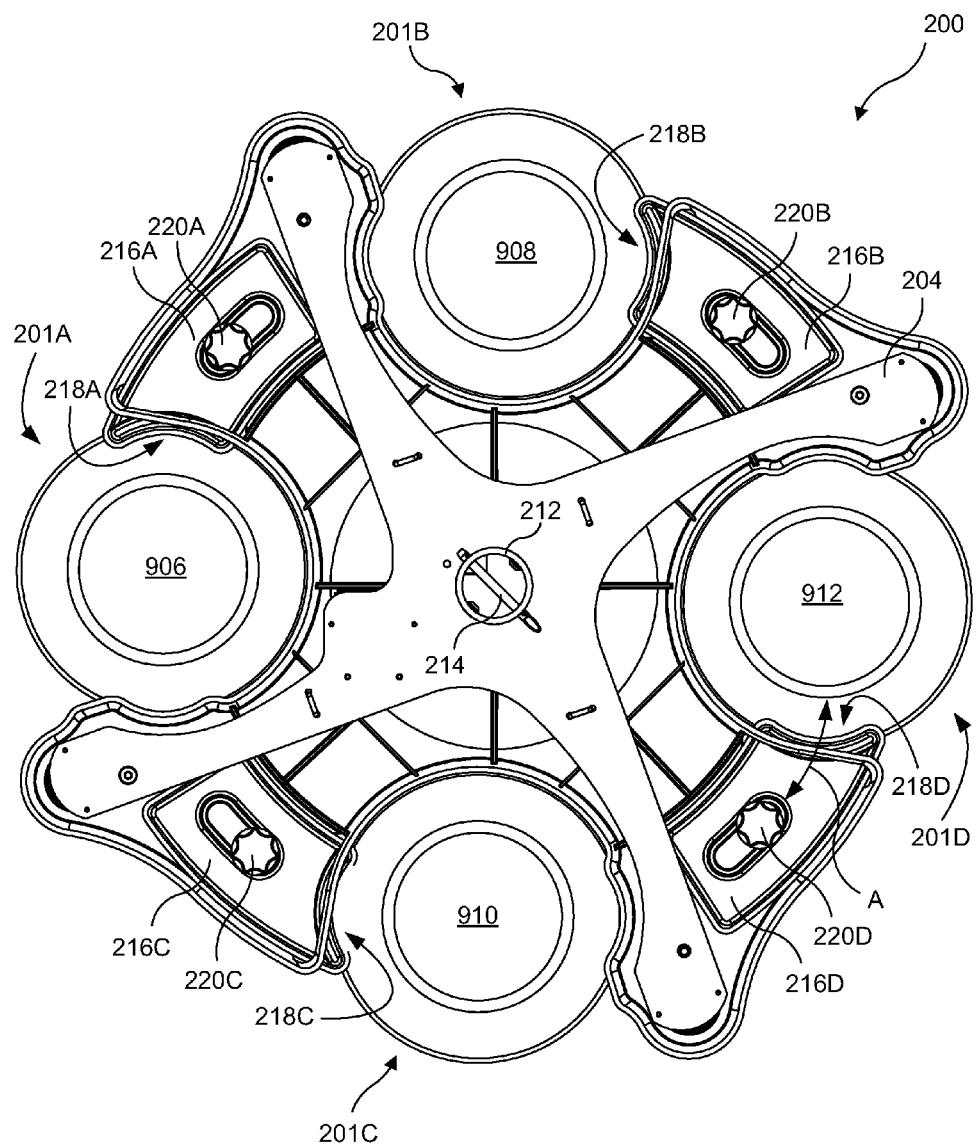
FIG. 7 is a bottom view of an exemplary suction container hanger assembly.
Figure 8:
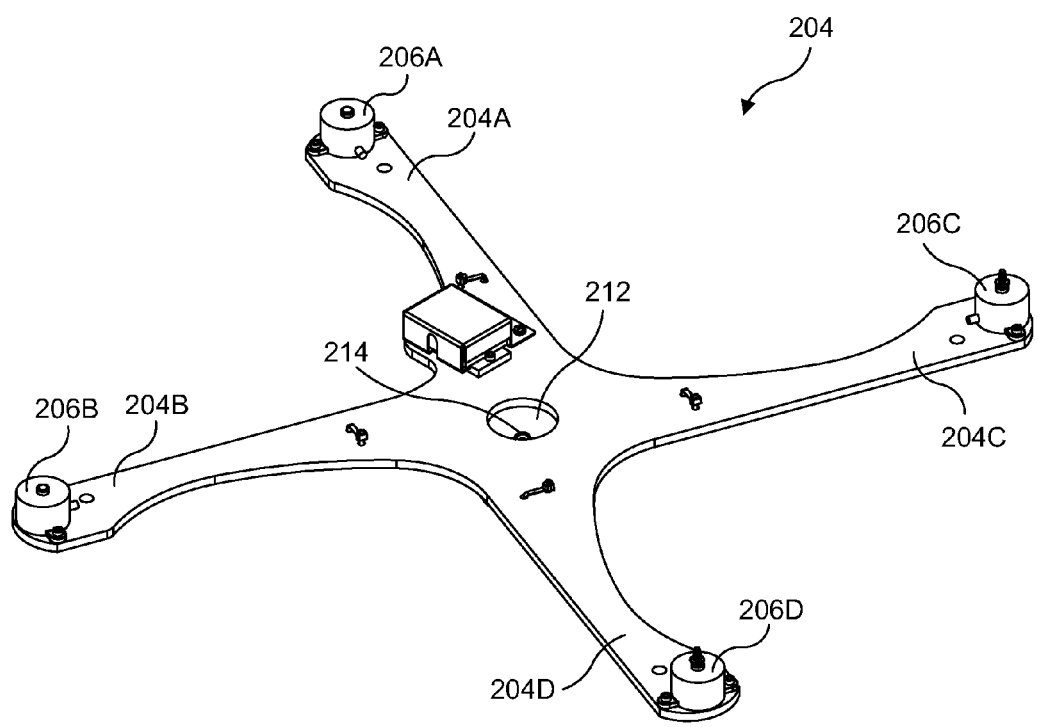
FIG. 8 is a perspective view of an exemplary load cell base.

In some exemplary embodiments, receiving openings 201A, 201B, 201C, 201D may be arranged generally symmetrically. In some exemplary embodiments, receiving openings 201A, 201B, 201C, 201D of different sizes may be provided and/or adjusters 216A, 216B, 216C, 216D may be adjusted to accommodate canisters 906, 908, 910, 912 of one or more sizes and/or shapes, as best seen in FIG. 7. In an exemplary embodiment, each adjuster 216A, 216B, 216C, 216D may be individually adjustable. In an exemplary embodiment, receiving openings 201A, 201B, 201C, 201D and their associated adjusters 216A, 216B, 216C, 216D may be capable of receiving suction canisters 906, 908, 910, 912 with diameters up to about 6.6 inches.

Adjusters 216A, 216B, 216C, 216D may be slidable generally radially inward and/or outward with respect to the opening 201 (e.g., as shown by arrow A). In an exemplary embodiment, adjusters 216A, 216B, 216C, 216D may include a shaped end, such as curved end 218A, 218B, 218C, 218D, which may be adapted to interface with a suction canister 906, 908, 910, 912. Knobs 220A, 220B, 220C, 220D may be threadedly engaged with suction canister hanger 202 and/or adjusters 216A, 216B, 216C, 216D to allow adjusters 216A, 216B, 216C, 216D to be secured in position relative to suction canister hanger 202. For example knobs 220A, 220B, 220C, 220D may include threaded rods which may be received in corresponding threaded openings on suction canister hanger 202. In such an exemplary embodiment, rotation of knobs 220A, 220B, 220C, 220D may tighten knobs 220A, 220B, 220C, 220D against adjusters 216A, 216B, 216C, 216D and/or may loosen knobs 220A, 220B, 220C, 220D away from adjusters 216A, 216B, 216C, 216D, thereby allowing a user to selectively secure and release an adjuster 216A, 216B, 216C, 216D for adjustment. In other exemplary embodiments, various types of retainers known in the art may be substituted for knobs 220A, 220B, 220C, 220D, such as other arrangements of threaded retainers, cam-type retainers, clips, etc.

In an exemplary embodiment, adjusters 216A, 216B, 216C, 216D may be initially positioned and secured using knobs 220A, 220B, 220C, 220D. Subsequent installation and removal of canisters 906, 908, 910, 912 may be accomplished by lowering canisters 906, 908, 910, 912 into pre-adjusted receiving openings 201A, 201B, 201C, 201D and raising canisters 906, 908, 910, 912 out of pre-adjusted receiving openings 201A, 201B, 201C, 201D. Adjustment of knobs 220A, 220B, 220C, 220D may only be necessary when a canister 906, 908, 910, 912 of a different size is utilized. In other exemplary embodiments, one or more adjusters 216A, 216B, 216C, 216D may be adjusted more frequently during use, such as with each canister replacement.

An exemplary suction canister hanger 202 may include a collar 203, which may receive pole 20 (which is shown in FIG. 2) therethrough. Suction canister hanger 202 may be supported by a load cell base 204, which may include a housing 212 for receiving pole 20 therethrough and/or a pin 214 which may extend through pole 20. Some exemplary load cell bases 204 may be constructed of metal, such as steel.

In some exemplary embodiments, suction canister hanger 202 may be supported on load cell base 204 substantially by load cells 206A, 206B, 206C, 206D, which may be mounted on arms 204A, 204B, 204C, 204D. Load cells 206A, 206B, 206C, 206D may be adapted to provide electrical outputs associated with the weight carried by the suction canister hanger 202. In an exemplary embodiment, load cells 206A, 206B, 206C, 206D may include button-type compression cells. Other exemplary embodiments may utilize load cells of other types, such as beam-type load cells and/or strain gauges.

In some exemplary embodiments, the total weight supported by load cells 206A, 206B, 206C, 206D may be about equal to sum of the weight of suction canister hanger 202, the empty weights of canisters 906, 908, 910, 912, and the weight of any contents of canisters 906, 908, 910, 912. An exemplary embodiment may utilize signals provided by one or more load cells 206A, 206B, 206C, 206D to determine a volume of liquid collected in one or more suction canisters 906, 908, 910, 912 and/or to determine when one or more suction canisters 906, 908, 910, 912 has been replaced.

In some exemplary embodiments, load cells 206A, 206B, 206C, 206D may be positioned on load cell base 204 such that suction canisters 906, 908, 910, 912 are located generally towards collar 203 with respect to load cells 206A, 206B, 206C, 206D. In other words, load cells 206A, 206B, 206C, 206D may be positioned radially farther from collar 203 than the centers of mass of suction canisters 906, 908, 910, 912. Put another way, the centers of mass of suction canisters 906, 908, 910, 912 may be disposed inwardly with respect to spaced-apart load cells 206A, 206B, 206C, 206D. In some exemplary embodiments, load cell base 204 may include three or more load cells 206A, 206B, 206C, 206D. Such an arrangement may be useful when it is desired for the sum of the load cell readings to be representative of the total weight of the canisters 906, 908, 910, 912. Further, such an arrangement may be useful when uneven canister 906, 908, 910, 912 loading may occur.

Figure 9:
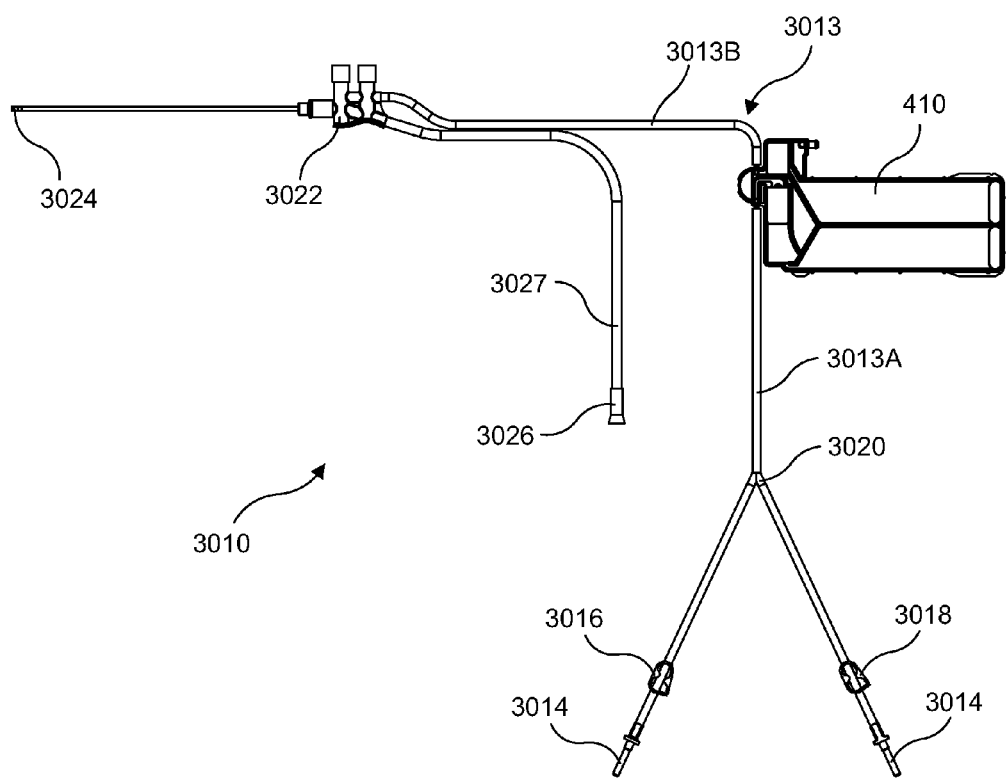
FIG. 9 is a schematic illustration of an exemplary trumpet valve tubing set.
Figure 10:
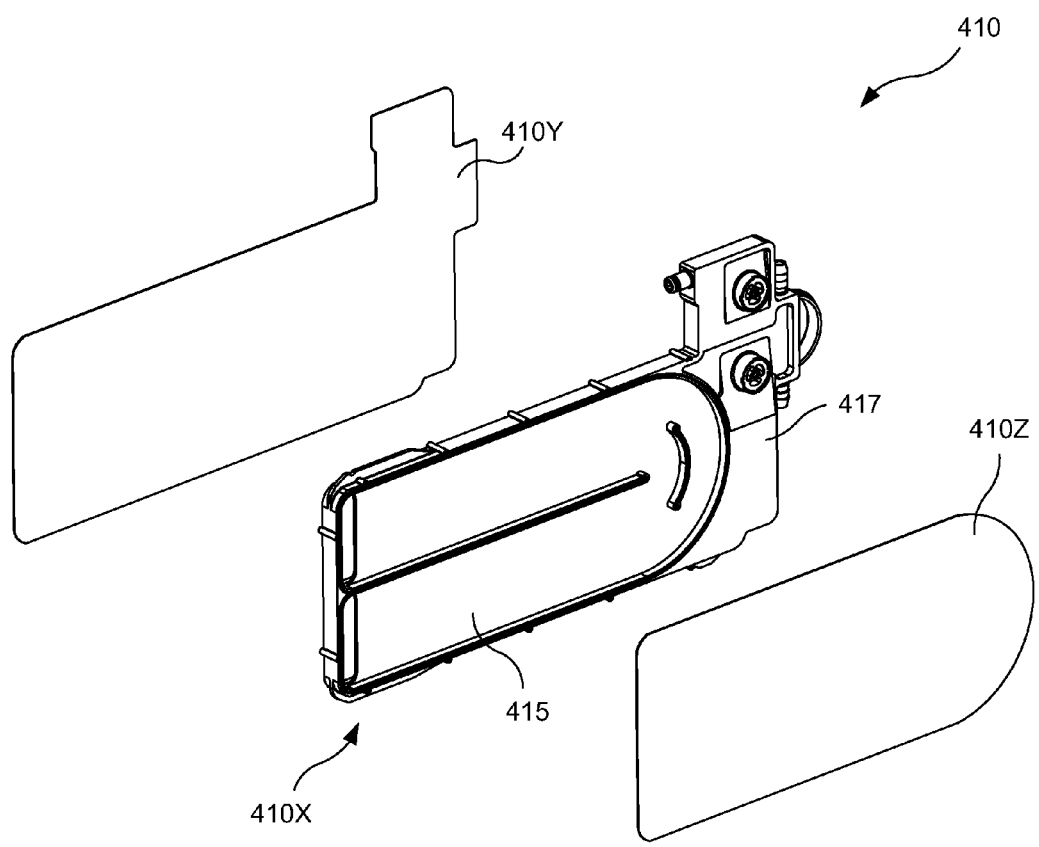
FIG. 10 is an exploded perspective view of an exemplary heating cartridge.
Figure 11:
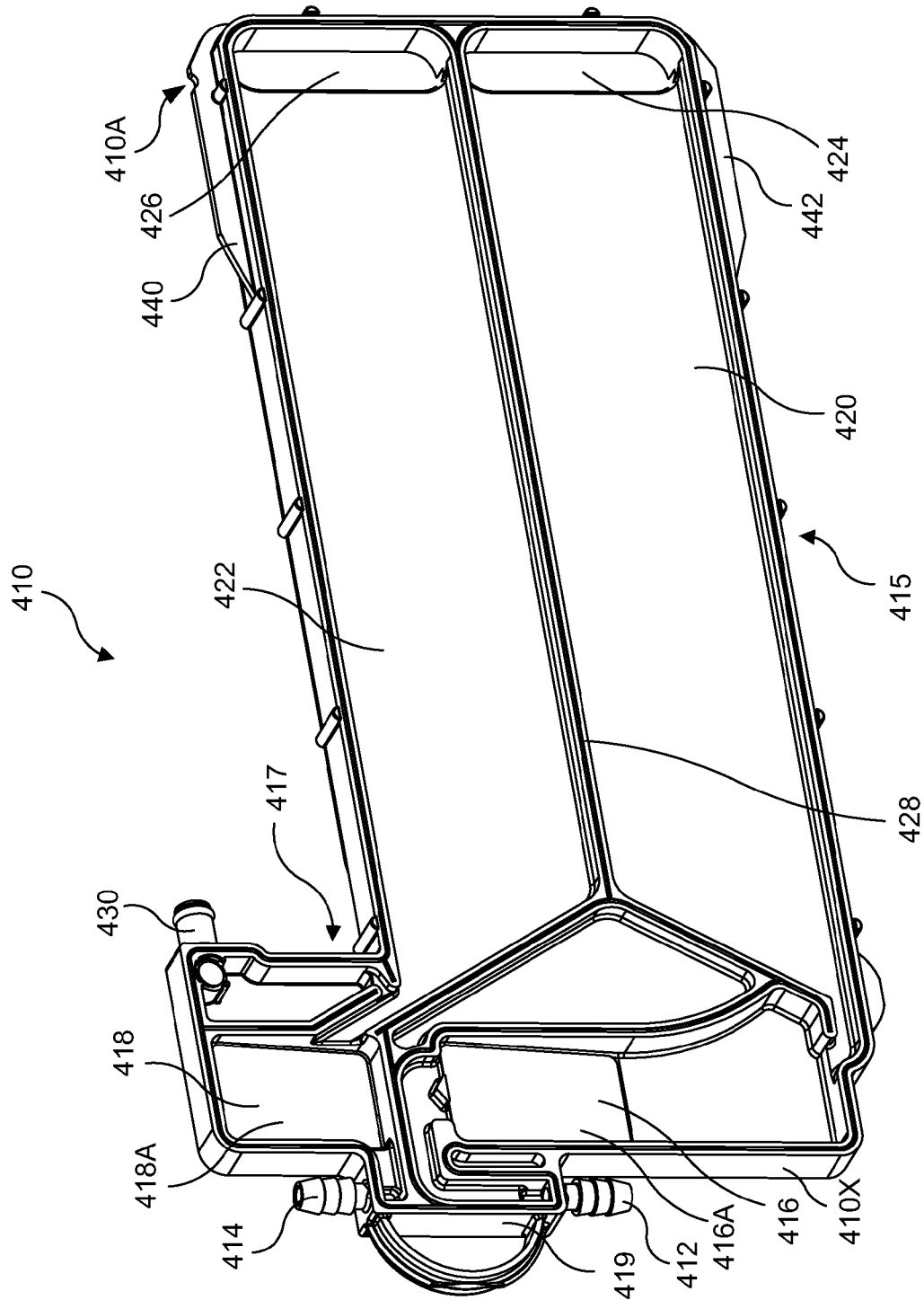
FIG. 11 is a perspective view of an exemplary heating cartridge.
Figure 12:
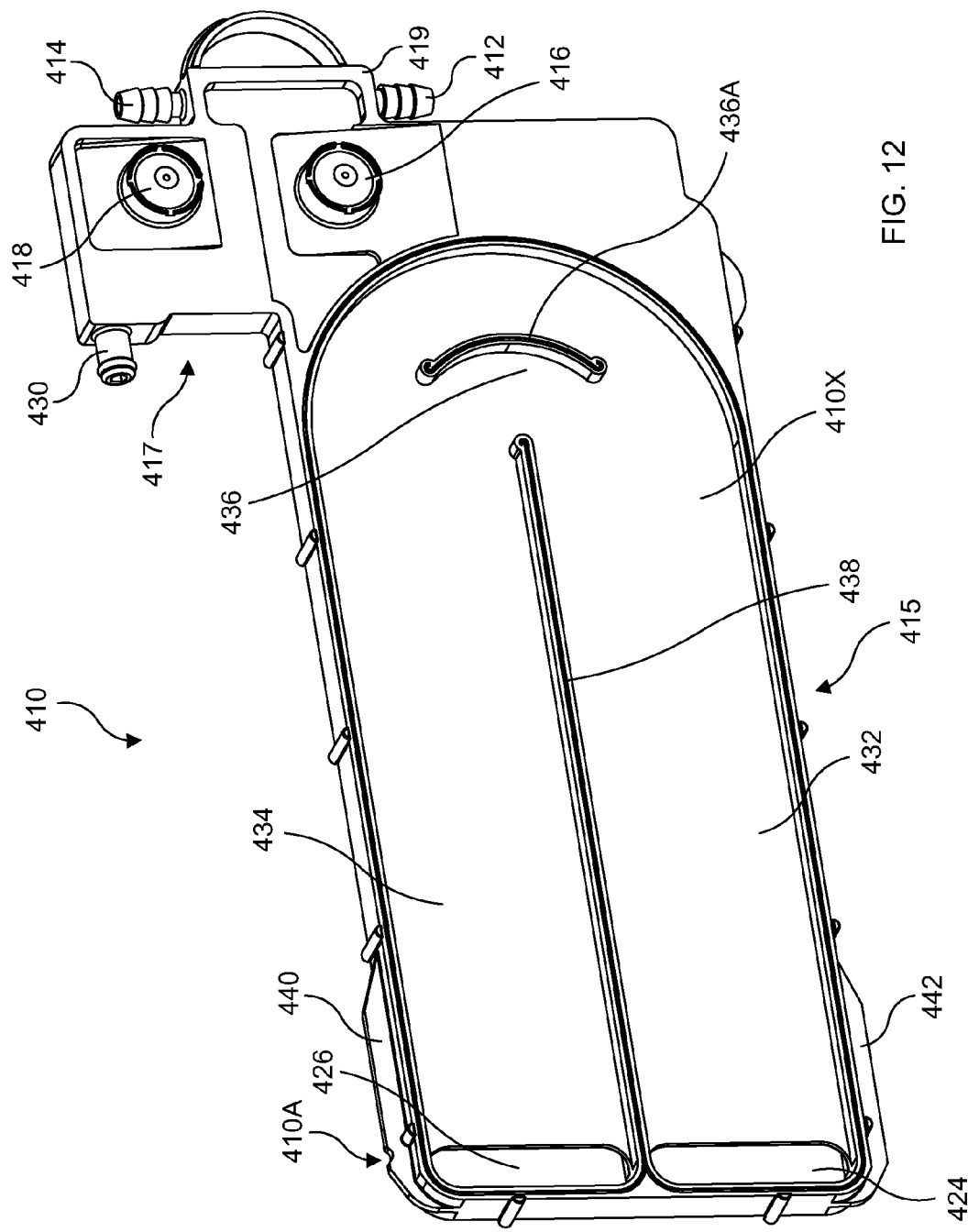
FIG. 12 is a perspective view of an exemplary heating cartridge.

FIG. 9 is a schematic diagram of an exemplary trumpet valve tubing set 3010, which may include cartridge 410. In an exemplary embodiment, trumpet valve tubing set 3010 may include irrigation tubing 3013 and suction tubing 3027. Irrigation tubing 3013 may include one or more connectors, such as spikes 3014, which may be adapted to couple with one or more fluid containers (such as fluid bags 902, 904). Exemplary tubing sets may be provided with single or multiple spikes 3014 in various exemplary embodiments. Irrigation tubing 3013 may include an upstream section 3013A, which may be fluidicly upstream of cartridge 410, and/or a downstream section 3013B, which may be fluidicly downstream of cartridge 410.

In an exemplary embodiment, one or more clamps 3016, 3018 may be provided downstream of the spikes 3014. Some exemplary embodiments may include a Y-connector 3020 and/or other similar device joining a plurality of sections of tubing. In an exemplary embodiment, cartridge 410 may be provided as part of tubing set 3010. Trumpet valve 3022 may be fluidicly connected to cartridge 410 (e.g., via tubing 3013B) and may include one or more valves for controlling flow of irrigation fluid and/or suction. Trumpet valve 3022 may include a tip 3024, which may be utilized for suction and/or irrigation. In some exemplary embodiments, tip 3024 may include electrosurgical components, such as an electrocautery tip. An exemplary suction tubing 3027 may include a suction connection 3026, which may be coupled to a source of suction via one or more suction containers (such as suction canisters 906, 908, 910, 912), for example. In such an exemplary embodiment, the one or more suction containers may be connected to a hospital's central suction and/or a standalone suction device, for example.

An example trumpet valve 3022 may comprise a single-use suction and irrigation device intended for use in surgical procedures, such as laparoscopic surgical procedures. An example trumpet valve 3022 may include two push-button operated valves, one for irrigation fluid and one for suction, that may be connected to a probe attachment port. The body of the suction valve may include a manually adjustable false air regulator. Various probes may be attached to the probe attachment port, such as 5 mm single-lumen probes and probes including monopolar or bipolar electrosurgical tips. Some example electrosurgical probes may include electrical cables that are coupleable to external electrosurgical generators. U.S. Pat. No. 6,234,205 describes an example trumpet valve and is incorporated by reference.

FIGS. 10-14 illustrate an exemplary cartridge 410 according to the present disclosure. Some exemplary cartridges may include a main or center body 410X (which may be substantially rigid) and/or one or more side sheets 410Y, 410Z (which may be relatively flexible). An exemplary cartridge may be generally L-shaped and substantially flattened, having a generally horizontally extending fluid IR exposure section 415 and a generally vertically extending elevated section 417, extending vertically up from the fluid heat transfer section 415. An exemplary cartridge 410 may include inlet and/or outlet connections, such as inlet fitting 412 and outlet fitting 414 positioned at the side of the cartridge with the vertically extending elevated section 417, where the inlet fitting 412 extends generally downward and the outlet fitting 414 extends generally upward from a tab section 419 extending from a side of the generally vertically extending elevated section 417. In an exemplary embodiment, inlet fitting 412 and/or outlet fitting 414 may include barb fittings; however, other exemplary embodiments may utilize other connection devices such as compression fittings, Luer-lock fittings, glue joints, and other connection devices known in the art. In an exemplary embodiment, cartridge 410 may include additional connections, such as fitting 430, which may connect to a pressure sensor (and/or a pressure transducer).

In an exemplary embodiment, cartridge 410 may include an internal flow path through which fluid may flow from inlet fitting 412 to outlet fitting 414. A front portion of an exemplary flow path is visible in FIGS. 11 and 14: lower, front fluid channel 420, port 424, port 426, and upper front fluid channel 422. In an exemplary embodiment, one or more walls (such as wall 428) may separate various fluid channels 420, 422. A back portion of the exemplary flow path is visible in FIG. 12: lower, back fluid channel 432, upper, back fluid channel 434 and turn section 436. In an exemplary embodiment, the internal flow path may direct fluid through and/or past one or more bubble traps 416, 418 (which may also be referred to as air venting chambers). In an exemplary embodiment, the bubble trap 416 nearer the inlet fitting 412 may be larger than the bubble trap 418 nearer the outlet fitting 414. In some exemplary embodiments, a larger bubble trap 416 near the inlet fitting 412 may remove bubbles delivered to cartridge 410 resulting from a replacement of a fluid bag 902, 904. In some circumstances, such bubbles may be relatively large. In some exemplary embodiments, a smaller bubble trap 418 near the outlet fitting 414 may remove bubbles not removed by bubble trap 416 and/or bubbles created during fluid warming within cartridge 410. In some exemplary embodiments, bubble traps 416, 418 may include hydrophobic membranes 416A, 418A as described in detail below.

Fluid channels 420, 422, 432 and 434 may include generally horizontally extending fluid channels having the following dimensions in an example embodiment: about 9.5" long by about 2" high by about 0.25" thick. In some example embodiments, the dimensions of fluid channels 420, 422, 432, 434 may be configured to provide a substantial amount of outwardly facing surface area relative to the internal volume to promote efficient warming of the fluid using IR lamps 312, 314, 316, 318.

In an exemplary embodiment, fluid may enter cartridge 410 at inlet fitting 412, may flow past bubble trap 416, and into lower, front fluid channel 420. Then, the fluid may flow through port 424 and into lower, back fluid channel 432. The fluid may generally reverse direction in turn section 436 and may flow into upper, back fluid channel 434. Turn section 436 may include one or more ribs 436A. Fluid may then flow through port 426, through upper, front fluid channel 422, past bubble trap 418, and out of cartridge 410 via outlet fitting 414. Fluid channels 432, 434 may be separated by a horizontal wall 438. Thus, such an exemplary embodiment may provide a three-dimensional fluid flow path P (e.g., the fluid flow path causes the fluid to flow in the X, Y, and Z directions), as best seen in FIG. 13.

Figure 13:
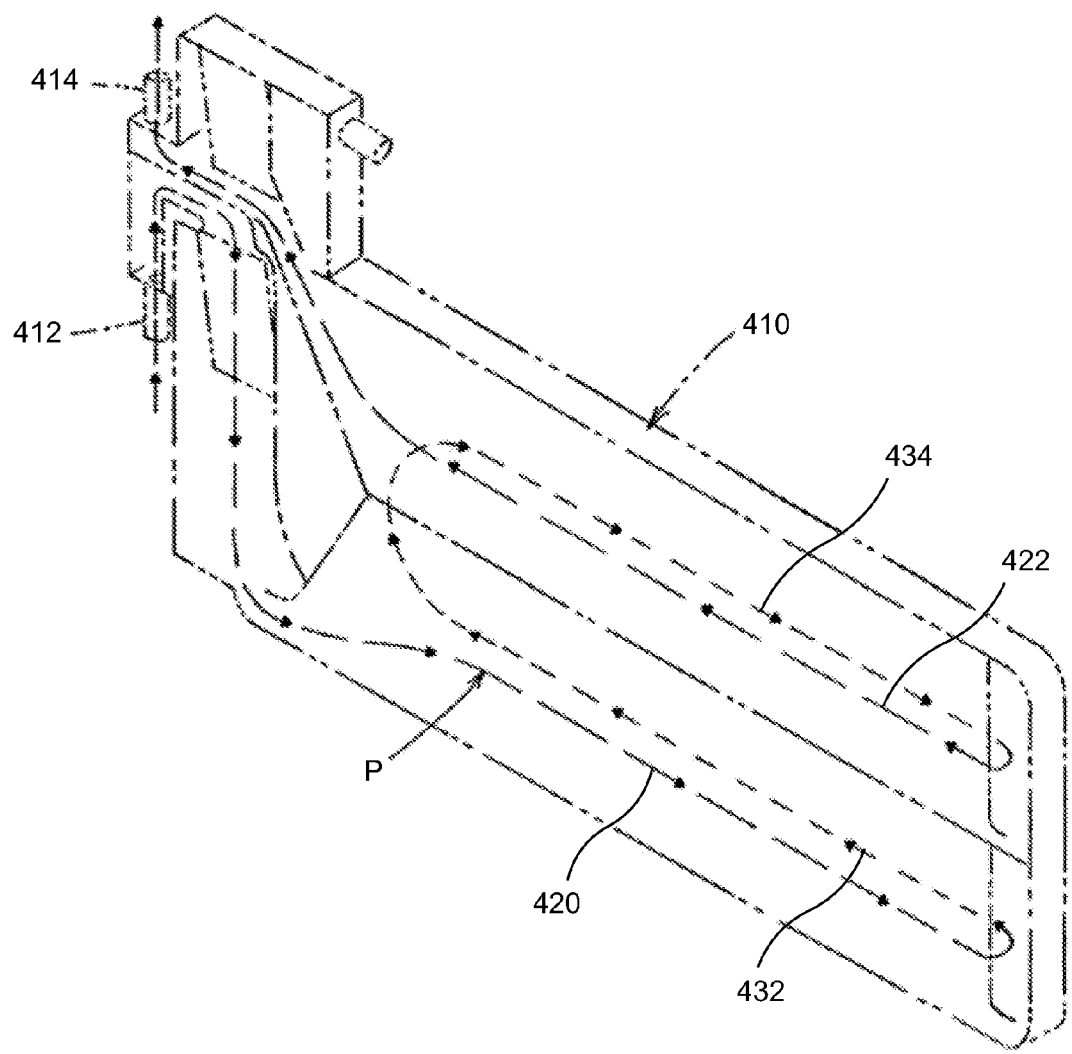
FIG. 13 is a perspective view of a heating cartridge illustrating an exemplary three-dimensional fluid flow path.

As illustrated in FIG. 13, an elongated, three-dimensional, convoluted path P may be defined in cartridge 410 between inlet fitting 412 and outlet fitting 414.

Figure 19:
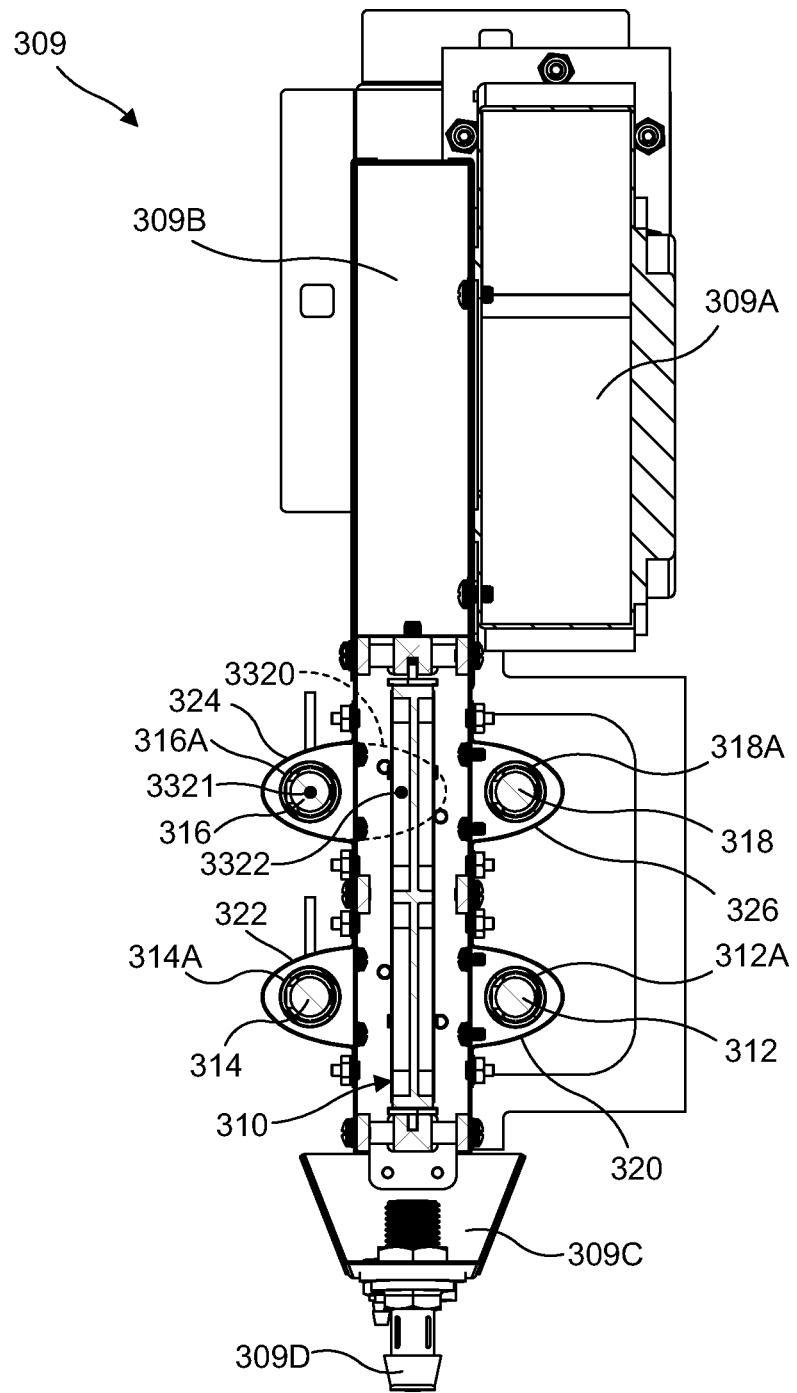
FIG. 19 is a cross-sectional view of an exemplary heater assembly.

Cartridge 410 may be designed such that path sections, defined by fluid channels 420, 432, 434, and 422 are substantially aligned and/or substantially in registry with IR lamps 312, 318, 316, 314, respectively, when cartridge 410 is inserted into slot 310 of heater assembly 309, as illustrated in FIG. 19.

In some exemplary embodiments, increasing the length of the fluid flow path within the cartridge may increase the time the fluid is subjected to heating by the IR lamps and, thereby, enable increased fluid warming at increased fluid flow rates. A cartridge including a three-dimensional flow path with multiple fluid channels exposed to IR lamps may enable efficient fluid warming and cost effective designs of both the cartridge and heater assembly. A two-dimensional flow path wherein the fluid is subjected to heating by the IR lamps for the same amount of time may result in a larger, less cost effective cartridge and a larger, less cost effective heater assembly and/or less efficient fluid warming.

In some exemplary embodiments, one or more fluid channels may be arranged such that they are capable of transferring heat to one or more other fluid channels. For example, heat transfer from fluid channel 432 to fluid channel 420 may occur. Similarly, heat transfer from fluid channel 422 to fluid channel 434 may occur. Heat transfer between channels may aid in dissipating heat from warmer sections, particularly during stagnant or low flow conditions (such as when pump 112 is not running). Such heat transfer may not be possible with a two-dimensional fluid path.

A main body 410X of an exemplary cartridge 410 may be constructed of polycarbonate, which may be substantially rigid. In some exemplary embodiments, the main portion of cartridge 410 may be molded as a single piece. In some exemplary embodiments, various fittings, such as inlet fitting 412, outlet fitting 414, and fitting 430 may be integrally molded with the main portion of the cartridge 410, while such fittings may be separately installed pieces in other exemplary embodiments. In some exemplary embodiments, utilizing a single-piece molded cartridge main body may reduce the potential for fluid leakage because of a reduced number of joints. Similarly, employing integrally molded components, such as fittings 412, 414, 430 may reduce the potential for fluid leakage. In addition, integrally molded fittings (and other components) may be less expensive to manufacture and may require less labor (e.g., they do not need to be separately installed); thus, integrally molded construction may reduce the cost of cartridge 410.

Front and/or back sides of an exemplary cartridge may be covered by one or more sheets 410Y, 410Z of polycarbonate (such as LEXAN® polycarbonate), which may have a thickness in the range of approximately 0.010-0.030 inches, for example. In an exemplary embodiment, both the front and back sides are covered with polycarbonate sheets 410Y, 410Z having a thickness of approximately 0.020 inches. In an exemplary embodiment, one or more polycarbonate sheets 410Y, 410Z may be attached and/or sealed to the cartridge 410 using ultrasonic welding, for example. In some exemplary embodiments, rib 436A may simplify ultrasonic welding of polycarbonate sheets 410Y, 410Z to cartridge 410 by diffusing some energy which may be directed generally at the projecting portion of wall 438. The present disclosure contemplates that such polycarbonate materials may be highly transparent to IR energy (e.g., approximately 85% transmissive). Utilizing highly IR transparent materials may allow a relatively high percentage of the energy emitted by the IR lamps to directly warm fluid within the cartridge.

In an exemplary embodiment, materials from which various components are constructed (such as polycarbonate) may be substantially free of polyvinyl chloride (PVC) and/or bis(2-ethylhexyl)phthalate (DEHP). Such materials may be advantageous for environmental and/or patient safety reasons.

The present disclosure contemplates that positive displacement pumps of various types may provide advantages, such as an easily calculated flow rate. The present disclosure also contemplates that, due to their nature, certain types of positive displacement pumps may provide a pulsed flow. In some exemplary embodiments, it may be desirable to provide a non-pulsatile flow. An exemplary embodiment may include sheets 410Y, 410Z, which may be somewhat flexible and/or elastic. When utilized in connection with a pulsed fluid flow, such as that produced by some peristaltic and piston-type pumps, a cartridge 410 including one or more flexible sheets 410Y, 410Z may operate to at least partially dampen the pulses and/or to provide more continuous fluid flow and/or pressure.

Figure 15:
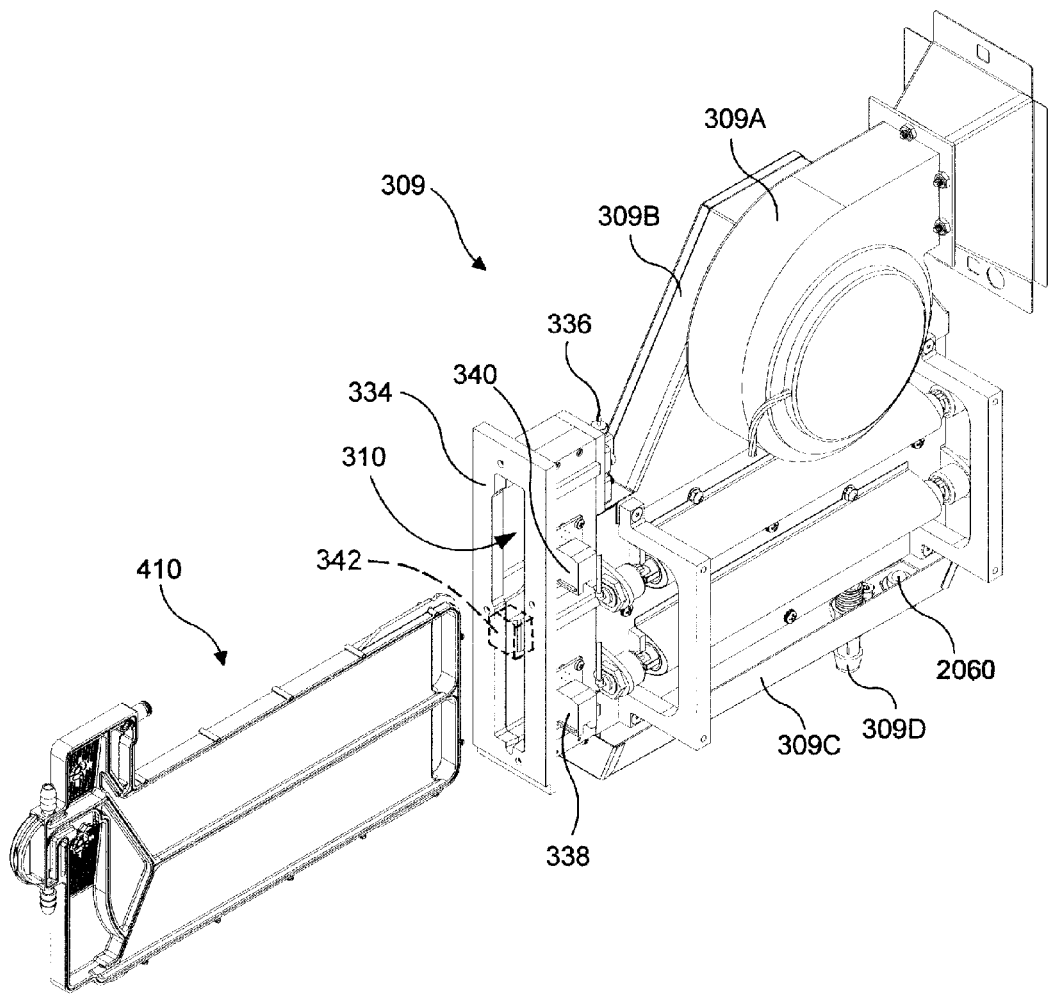
FIG. 15 is a perspective view of an exemplary heater assembly.
Figure 16:
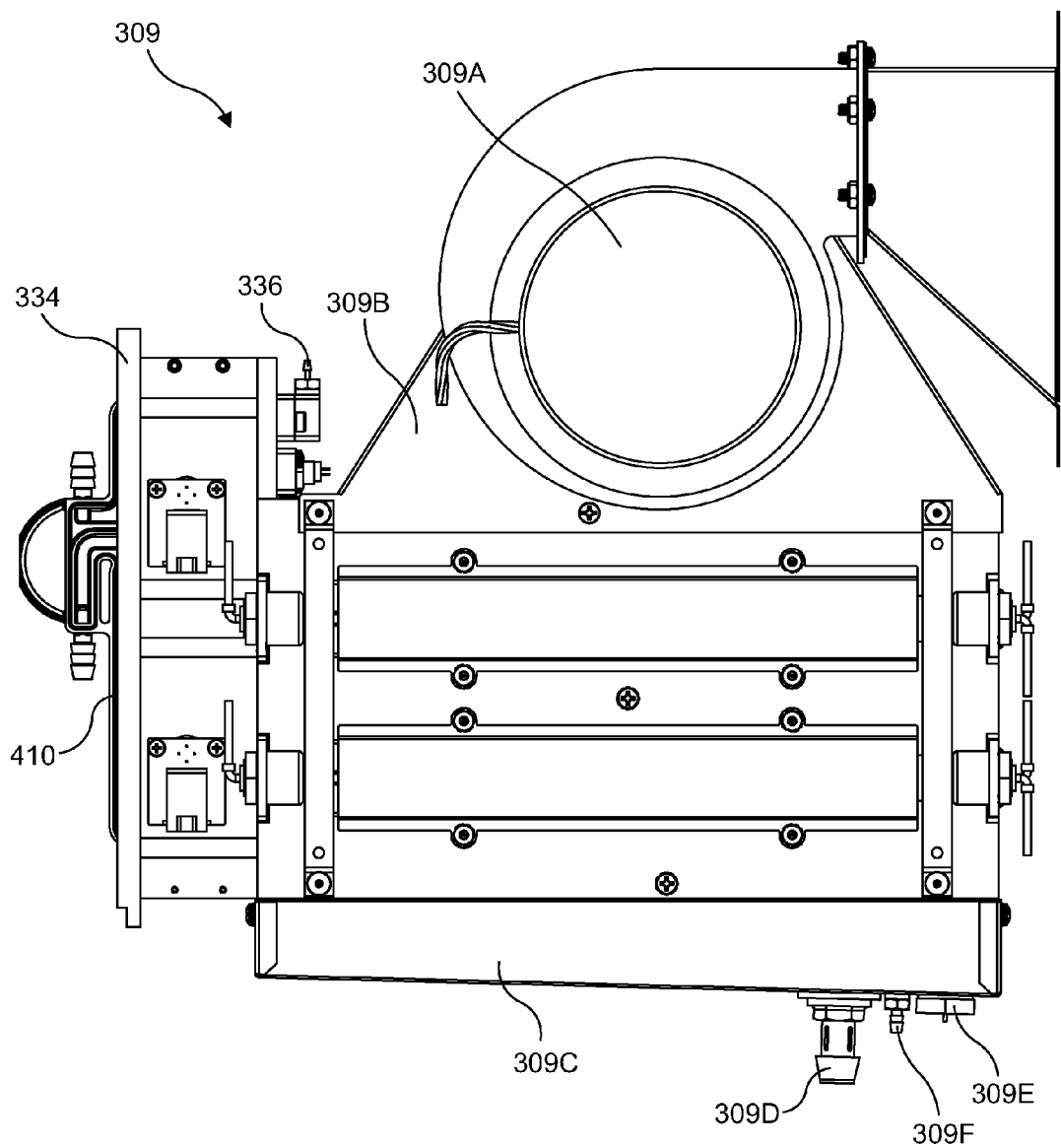
FIG. 16 is a side view of an exemplary heater assembly.
Figure 17:
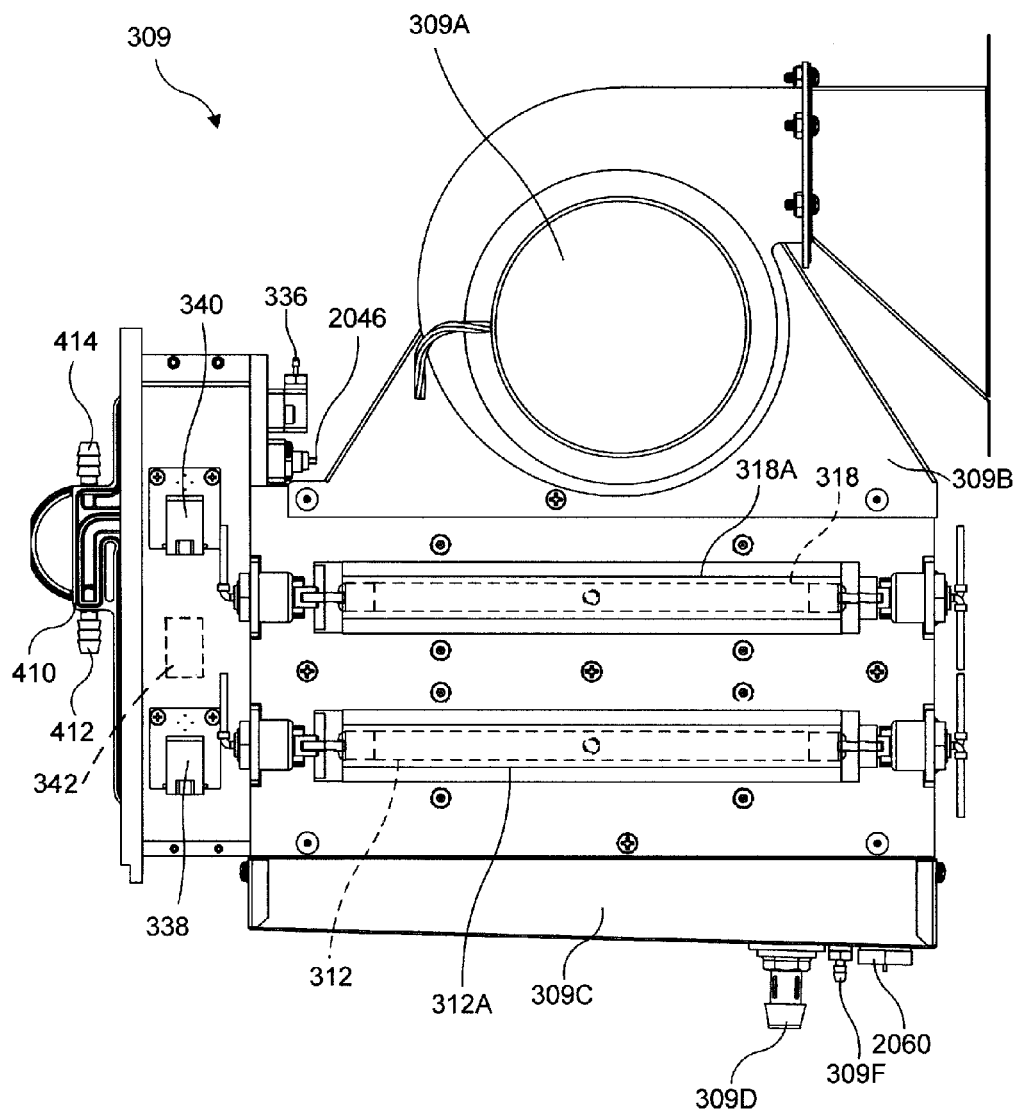
FIG. 17 is a side view of an exemplary heater assembly.
Figure 18:
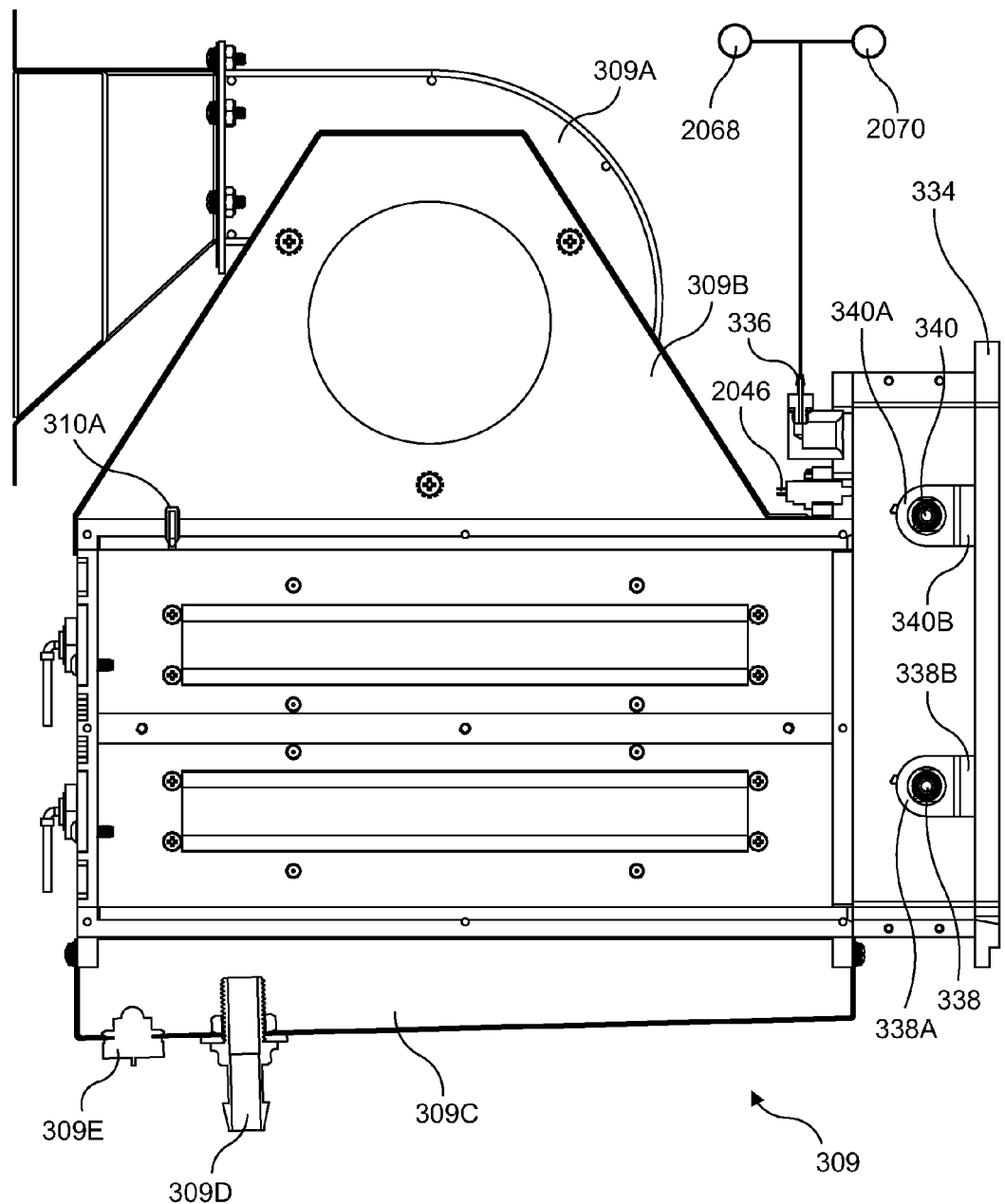
FIG. 18 is a cross-sectional view of an exemplary heater assembly.

An exemplary embodiment may include a cartridge 410 and a slot 310 (see, e.g., FIGS. 3 and 15) having complementary shapes, which may prevent insertion of the cartridge 410 in slot 310 in an improper orientation. For example, an exemplary cartridge may generally have an L-shape (see, e.g., the portion of cartridge 410 including bubble trap 418), and the slot 310 may prevent full insertion of the cartridge 410 in an inverted orientation by only accommodating the L-shape in the proper orientation. An exemplary embodiment may include one or more ridges, such a upper ridge 440 and/or a lower ridge 442, which may be arranged to engage one or more corresponding grooves in slot 310. In some exemplary embodiments, upper ridge 440 and lower ridge 442 may have different widths (and/or shapes), and their corresponding grooves in slot 310 may be sized such that cartridge 410 cannot be inserted into slot 310 in an inverted orientation. Upper ridge 440 and/or lower ridge may extend at least part of the length of cartridge 410 and/or may be discontinuous. In some exemplary embodiments, one or both of upper ridge 440 and lower ridge 442 may include an engagement feature, such as notch 410A, which may be used to releasably retain cartridge 410 within slot 310 of heater assembly 309.

Figure 14:
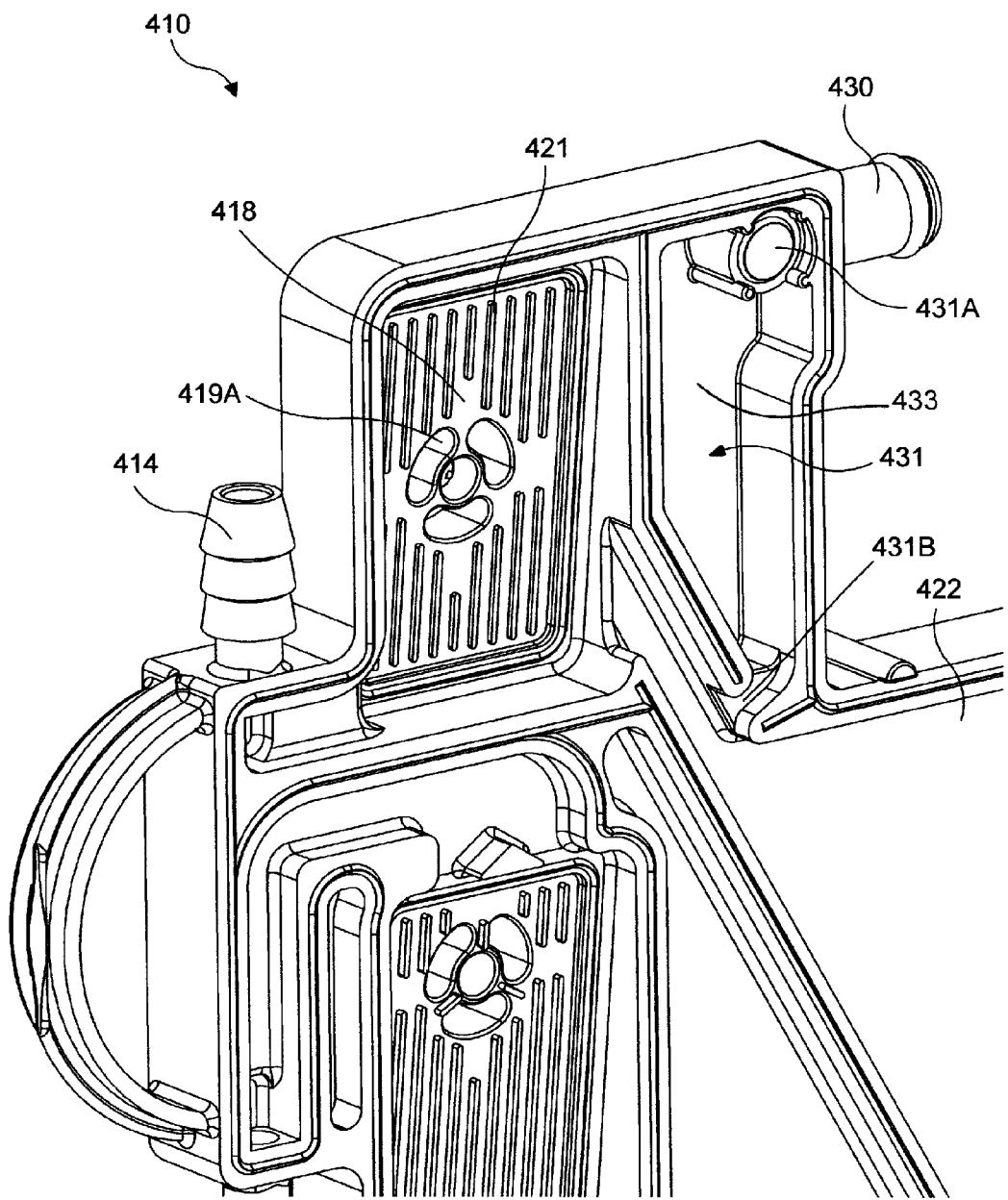
FIG. 14 is a perspective view of a heating cartridge illustration an exemplary bubble trap.

FIG. 14 is a detailed perspective view of a portion of an exemplary cartridge 410. An exemplary bubble trap 418 may be provided in the elevated section 417 of the cartridge and may include a plurality of vertically extending ridges 421 and/or one or more central openings 419A. The bubble trap 418 may be covered with a hydrophobic membrane adapted to vent bubbles of gas from fluid. Ridges 421 (and/or similar structures) may provide support for the hydrophobic membrane against the fluid while allowing gas to pass through the hydrophobic membrane. Gas may exit through openings 419A, which may be covered by a closure, such as an umbrella valve, which may be arranged to operate as a one-way valve. Thus, gas may exit through openings 419A but air may be prevented from entering through openings 419A.

In an exemplary embodiment, at least a portion of the bubble trap covered by the hydrophobic membrane may be canted towards the fluid side of the membrane. Such an arrangement may increase the contact between a bubble and the membrane, which may encourage the gas to pass through the membrane. More specifically, a bubble trap may include a generally vertically oriented chamber through which fluid may flow. At least one side of the chamber may include the hydrophobic membrane, which may be angled downwardly inward such that a rising bubble may be pressed against the hydrophobic membrane. The present disclosure contemplates that a relatively larger chamber may provide a relatively lower fluid velocity; thus, a larger chamber may increase the probability that a bubble may remain in the chamber and/or may exit through the hydrophobic membrane, as opposed to being swept away by the fluid flow prior to exiting through the hydrophobic membrane.

In an exemplary embodiment, fitting 430 may connect to the internal fluid path of the cartridge 410 via pressure sensor fluid path 431 provided in the vertical portion of the cartridge adjacent to the bubble trap 418, which may include a hydrophobic filter 431A. Pressure sensor fluid path 431 may include a narrowed opening 431B into a vertically disposed cavity 433, which may provide fluidic communication with fluid channel 422. The hydrophobic filter 431A may be provided in an upper portion of the cavity 433. In such an embodiment, fitting 430 (which may be connectable to a pressure sensing device) may convey substantially only gas, and fluid may be substantially retained within cartridge 410. Because the gas may pass through hydrophobic filter 431A, the gas may be exposed to the pressure of the fluid, and the gas may transmit the pressure to the pressure-sensing device. Thus, the pressure-sensing device may remain dry while sensing the fluid pressure. Additionally, hydrophobic filter 431A may assist in maintaining sterility of cartridge 410, such as by preventing infiltration of foreign matter into cartridge 410 through fitting 430.

The present disclosure contemplates that pressure readings may become inaccurate if fluid comes into contact with hydrophobic filter 431A. Some exemplary embodiments may be constructed such that the volume of gas downstream of hydrophobic filter 431A (e.g., fittings, conduits, and/or pressure sensors) and/or the volume of air upstream of hydrophobic filter 431A (e.g., in pressure sensor fluid path 431) may reduce the likelihood that fluid may contact hydrophobic filter 431A. For example, pressure sensor fluid path 431 may be configured to retain a volume of gas (e.g., air) in the cavity 433 sufficient to prevent fluid from contacting hydrophobic filter 431A during expected pressure excursions (e.g., the level of the fluid within pressure sensor fluid path 431 will not rise to hydrophobic filter 431A).

Some exemplary embodiments may include one or more pressure sensors and/or transducers fluidicly coupled to fitting 430, via heater assembly 309, as shall be described in greater detail below. For example, some exemplary embodiments may include two or more pressure sensors and/or transducers, the outputs of which may be compared. Comparisons of the outputs of a plurality of pressure sensors may aid in the identification of a faulty pressure sensor and/or an inaccurate pressure reading. For example, if pressure readings from at least two pressure sensors agree within an acceptable tolerance band, operation may continue. If the pressure readings from two pressure sensors differ by an amount in excess of the acceptable tolerance band, heater assembly 309 and/or pump 112 may be shut down and/or an alarm may be actuated.

FIGS. 15-19 are views of an exemplary heater assembly 309. An exemplary heater assembly 309 may include a slot 310 for receiving cartridge 410. In some exemplary embodiments, a portion of slot 310 may be defined by a guide 334 (see, e.g., FIG. 15), which may assist a user in inserting cartridge 410 into slot 310. An exemplary embodiment may include temperature sensors, such as IR temperature sensors 338, 340, which may be adapted to sense the temperature of fluid within cartridge 410. For example, IR temperature sensors 338, 340 may detect IR energy emitted by fluid within cartridge. By ascertaining the wavelength of the emitted energy, IR temperature sensor 338, 340 may provide an output associated with the temperature of the fluid adjacent the IR temperature sensor 338, 340. An exemplary heater assembly 309 may also include one or more intermediate temperature sensors as discussed below.

Some exemplary heater assemblies 309 may include a downwardly angled trough 309C, which may be mounted generally below slot 310 and/or which may be configured to catch fluid leakage from cartridge 410 in slot 310. In a lower portion, the trough 309C may include a drain fitting 309D and/or a fluid detector 2060 (such as an optical liquid detector, resistance liquid detector, continuity liquid detector, ultrasound liquid detector, infra-red liquid detector, and the like), which may output an electrical signal associated with detection of leakage from the cartridge. In some example embodiments, fluid detector 2060 may be located proximate a lowest level of trough 309C. In some exemplary embodiments, trough and/or drain fitting 309D may be sized to allow drainage of fluid at a rate greater than would be expected in the event of a catastrophic failure of cartridge 410 (e.g., the maximum flow rate delivered by pump 112). In some example embodiments, detection of fluid in trough 309C by fluid detector 2060, which may indicate a leak from cartridge 410, may result in an alarm and/or automatic shutdown of pump 112 and/or heater assembly 309.

Some exemplary embodiments may include a secondary drain fitting 309F, which may be coupled to a source of vacuum to remove fluid from trough 309C. More specifically, some drain fittings 309D may extend upwards from the floor of trough 309C, which may prevent complete draining of trough 309C through drain fitting 309D. Fluid detector 2060 may be mounted such that it may detect even minimal amounts of fluid within trough 309C. Thus, secondary drain fitting 309F may be used to withdraw residual fluid from trough 309C which may be at a level below drain fitting 309D but above fluid detector 2060.

Some exemplary heater assemblies 309 may include a blower 309A, which may be configured to draw cooling air through the heater assembly 309. In some exemplary embodiments, such cooling air may prevent an over temperature condition within heater assembly 309, such as at low fluid flow rates. In some exemplary embodiments, blower 309A may be attached to a plenum 309B, which may be connected to an upper portion of slot 310, such that air may be drawn upwards past cartridge 410. More specifically, some heater assemblies 309 may be configured such that blower 309A may be operative to draw air in around trough 309C, upward through slot 310 past cartridge 410, through plenum 309B, and away from heater assembly 309 through blower 309A. Some exemplary blowers 309A may be configured to run at more than one speed and/or the speed of the blower 309A may vary with temperature (e.g., such that the airflow is increased when the temperature is higher).

In some exemplary embodiments, temperature sensors 338, 340 may be mounted such that they detect the temperature of fluid flowing through cartridge 410 fluidicly near inlet fitting 412 and outlet fitting 414, respectively. In an exemplary embodiment, temperature sensors 338, 340 may be mounted such that they detect the temperature of fluid flowing through cartridge 410 prior to the fluid entering fluid channel 420 and after the fluid exits fluid channel 422. Some exemplary temperature sensors may be mounted such that they detect the temperature of fluid in cartridge 410 at positions that are unlikely to include stagnant areas, such that the detected temperatures are representative of the temperatures of the fluid flowing through cartridge 410. Some exemplary embodiments may include shields, such as rings 338A, 340A, which may reduce the effect of airflow caused by blower 309A on temperatures detected by temperature sensors 338, 340. Rings 338A, 340A may include tapered ramps 338B, 340B, which may assist in guiding cartridge 410 into slot 310. In an exemplary embodiment, a temperature sensor, such as an IR temperature sensor 342, may be mounted such that it senses the temperature of fluid in cartridge 410, such as fluid at an intermediate point in the internal flow path through cartridge 410. For example, IR temperature sensor 342 may be mounted within heater assembly 309 such that it measures the temperature of the fluid in cartridge 410 proximate turn section 436.

An exemplary heater assembly 309 may include a fitting 336 that may be fluidicly connected to fitting 430 on cartridge 410 when cartridge 410 is installed in the heater assembly. Connection of fitting 430 to fitting 336 may create a sensor fluid path that connects path (chamber) 431 in cartridge 410 to pressure sensors 2068, 2070, schematically illustrated in FIG. 18. In some exemplary embodiments, a hydrophobic filter mounted within cartridge 410 may be utilized to prevent liquid from flowing through fitting 430, while allowing gas flow through the sensor fluid path.

A first set of IR lamps 312, 318 may be mounted on one side of slot 310, and a second set of IR lamps 314, 316 may be mounted on the other side of slot 310. Thus, IR lamps 312, 318 may be directed towards one side of cartridge 10, and IR lamps 314, 316 may be directed towards the other side of cartridge 410. As shown in the figures, in an example embodiment, the IR lamps 312, 314, 316, 318 may be generally cylindrical and may have axes running generally along the horizontal direction of the cartridge. In some exemplary embodiments, individual IR lamps 312, 314, 316, 318 may include a reflective coating (e.g., gold or aluminum oxide), such as on about 60% of the surface area so as to direct IR energy toward cartridge 410. Some exemplary embodiments including IR lamps 312, 314, 316, 318 having reflective coatings may or may not include reflector shrouds 320, 322, 324, 326 running along the length of a respective IR lamp 312, 314, 316 and 318. In some exemplary embodiments, utilizing IR lamps 312, 314, 316, 318 with reflective coatings may provide improved efficiency over uncoated IR lamps 312, 314, 316, 318.

In some exemplary embodiments, individual IR lamps 312, 314, 316, 318 may be mounted within and/or behind protective covers, such as quartz glass tubes 312A, 314A, 316A, 318A. In some exemplary embodiments, quartz glass tubes 312A, 314A, 316A, 318A may prevent leakage of fluid from cartridge 410 from contacting IR lamps 312, 314, 316, 318. Some exemplary embodiments may not include quartz glass tubes 312A, 314A, 316A, 318A (or other covers) and/or IR lamps 312, 314, 316, 318 may be substantially directly exposed to cartridge 410, which may increase fluid warming efficiency.

The present disclosure contemplates that an ellipse includes two foci, and that rays emitted by a source at one of the foci are reflected to the other foci. In an exemplary embodiment, one or more reflector shrouds 320, 322, 324, 326 may include at least a partial substantially elliptical shape (in cross section) with an IR lamp 312, 314, 316, 318 located at or near one of the foci and with a portion of cartridge 410 located at or near the other foci. Accordingly, IR energy emitted by the IR lamp 312, 314, 316, 318 may be reflected to the portion of the cartridge 410. For example, reflector 324 and cartridge 410 may be arranged in relation to an ellipse 3320 and its two foci 3321, 3322. In an exemplary embodiment, IR lamp 316 may be located at or near foci 3321 and/or fluid channel 434 is located at or near foci 3322. One or more of reflector shrouds 320, 322, 324, 326 may have a similar arrangement.

In an exemplary embodiment, one or more reflector shrouds 320, 322, 324, 326 may be arranged to direct IR energy at particular locations on cartridge 410 and to limit the amount of IR energy directed at other locations on cartridge 410. For example, one or more reflector shrouds 320, 322, 324, 326 may be arranged to limit the IR energy directed at portions of cartridge 410 where limited IR exposure may be desired. For example, limited IR exposure may be desired for portions of cartridge 410 including little or no fluid and/or portions that are not substantially transparent to IR energy. For example, reflector shrouds 320, 322, 324, 326 may be arranged to limit the IR energy directed at various seams and/or welds. In some exemplary embodiments, such use of reflector shrouds 320, 322, 324, 326 may obviate a need to employ a cartridge 410 including substantially reflective portions to prevent absorption of IR energy in undesired locations. In some exemplary embodiments, directing a greater proportion of the IR energy towards desired positions on the cartridge 410 may increase the efficiency of the device.

In some exemplary embodiments, reflector shrouds including other shapes may be employed. For example, a reflector shroud having a parabolic shape in cross-section may be utilized, and an IR lamp may be located approximately at the focal point of the parabola, and the IR energy may be directed towards at least a portion of a cartridge. In some exemplary embodiments, parabolic reflector shrouds may obviate a need to employ a cartridge 410 including substantially reflective portions to prevent absorption of IR energy in undesired locations (such as seams and/or welds). In some exemplary embodiments, directing a greater proportion of the IR energy towards desired positions on the cartridge 410 may increase the efficiency of the device.

In an exemplary embodiment, reflector shrouds 320, 322, 324, 326 may be constructed from aluminum and/or another reflective material. In some exemplary embodiments, reflector shrouds 320, 322, 324, 326 may include a polished surface. For example, reflector shrouds 320, 322, 324, 326 may be constructed of aluminum and may include polished surfaces. In some exemplary embodiments, reflector shrouds 320, 322, 324, 326 may be plated or otherwise coated with a reflective material (such as gold or aluminum oxide). For example, a steel reflector may include a gold-plated reflective surface.

In some exemplary embodiments, heater assembly 309 may include one or more engagement features, such as ball detent 310A. Ball detent 310A may releasably engage notch 410A of rib 440, thereby releasably retaining cartridge 410 in slot 310. Some exemplary embodiments may include one or more cartridge switches 2046, which may open or shut when a cartridge 410 is fully installed in slot 310.

Figure 20:
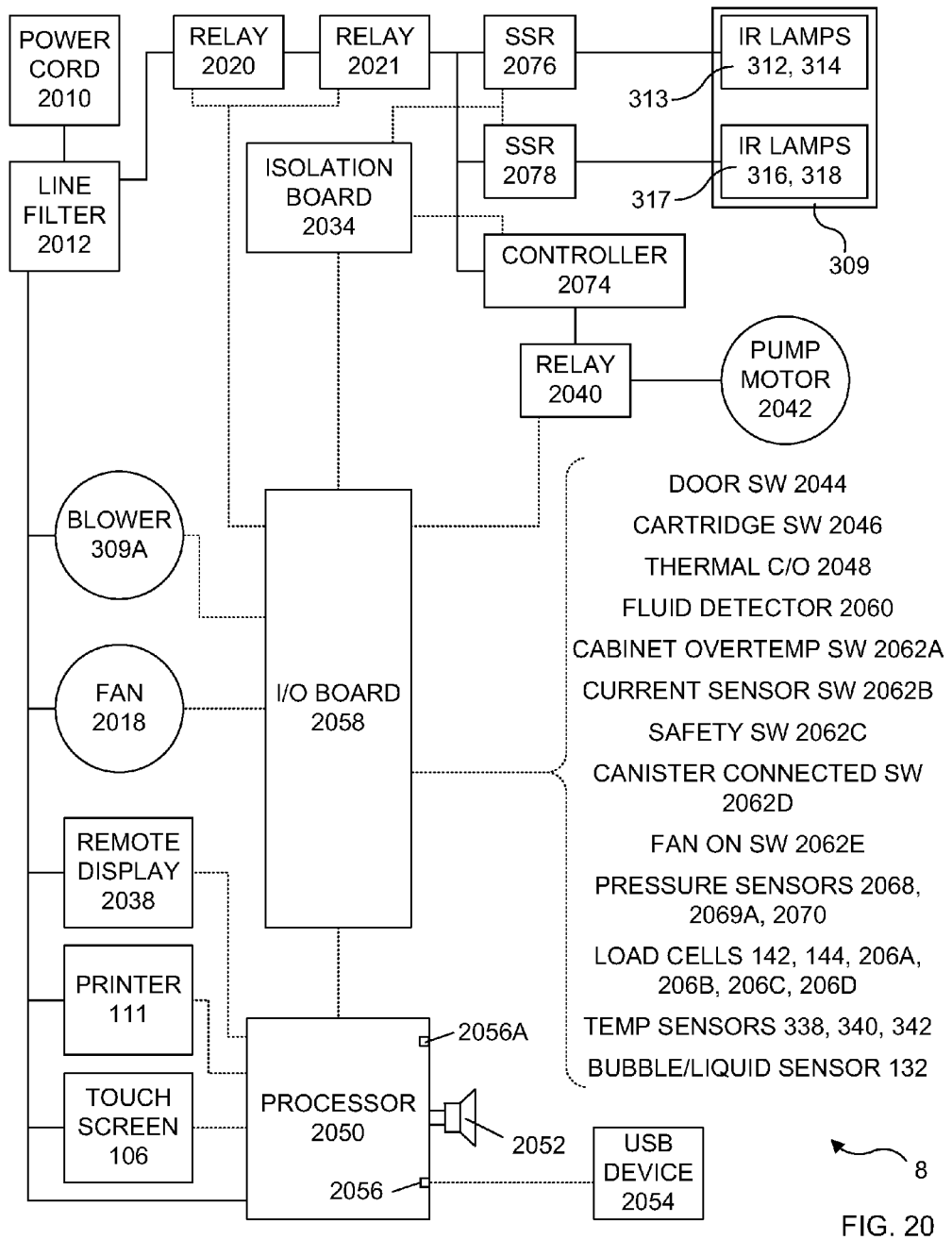
FIG. 20 is a schematic illustration of an exemplary power and control system.

FIG. 20 is a schematic diagram of an exemplary power and control system 8 for an exemplary fluid management system 10. It is to be understood that some exemplary embodiments may include various appropriate power supplies, circuit breakers, fuses, terminal boards, and the like, as would be apparent to one of skill in the art.

In an exemplary embodiment, electrical power may be supplied to a fluid management system 10 via a detachable power cord 2010, a line filter 2012, and appropriate fuses and/or circuit breakers. One or more power supply units may provide appropriate voltages and currents to the various electrical loads. In some exemplary embodiments, some components may receive power from more than one power supply. For example, a component utilizing two voltages may receive power from two power supplies.

An exemplary embodiment may include one or more fans and/or blowers (such as blower 309A and/or chassis fan 2018), one or more IR lamps 312, 314, 316, 318 (IR lamps 312, 314 may comprise a first group 313, and IR lamps 316, 318 may comprise a second group 317), a pump motor 2042 associated with pump 112, a printer 111, an isolation board 2034, and/or one or more remote display devices 2038 (such as a liquid crystal display, LED display, organic light-emitting diode display, and the like). For example, secondary display 106A may include a remote display 2038. Relays 2020, 2021, 2040 may selectively supply power to one or more components.

An exemplary isolation board 2034 may provide control signals to one or more solid state relays 2076, 2078, which may selectively supply power to IR lamps 312, 314, 316, 318, and/or controller 2074, which may be operatively coupled to pump motor 2042. In an exemplary embodiment, isolation board 2034 may include one or more digital-to-analog (D/A) converters which may supply an analog control signal (such as a 0-5V control signal for controller 2074). Isolation board 2034 may operate to isolate high voltages supplied to certain components (e.g., pump motor 2042 and/or IR lamps 312, 314, 316, 318), which may improve patient safety.

An exemplary embodiment may include one or more interlocks associated with certain conditions that may be operative to allow or prevent operation of various components of a fluid management unit 100. For example, a door switch 2044 may open if door 108 is opened, thereby cutting off power to IR lamps 312, 314, 316, 318 and/or pump motor 2042 via relays 2020, 2021, 2040. In some exemplary embodiments, door 108 may not be fully shut unless the cartridge 410 is properly installed, the tubing set is properly installed, and/or the pump head is properly shut. Thus, door 108 may function as a primary safety device by only allowing door switch 2044 to shut when these conditions are satisfied. In an exemplary embodiment, switch 2044 may be integrated with one or more of latch component 118 and corresponding latch component 120.

In an exemplary embodiment, a cartridge switch 2046 may shut when a cartridge 410 is fully inserted into heater assembly 309, thereby allowing relays 2020, 2021, 2040 to supply power to IR lamps 312, 314, 316, 318 and/or pump motor 2042. It is to be understood that in some exemplary embodiments, one or more switches 2044, 2046 may be configured to open when a condition is satisfied. In an exemplary embodiment, thermal cut off sensor(s) 2048 may open when a predetermined fluid temperature is exceeded, which may cause the cutting off of power to IR lamps 312, 314, 316, 318 and/or pump motor 2042.

An exemplary embodiment may include a main processor 2050, which may perform various functions (such as computing, calculation, control, interface, display, logging, and the like). Main processor 2050 may be operatively connected to one or more user interface components, such as touch screen 106 and/or remote display device 2038. An exemplary main processor 2050 may be operatively connected to one or more speakers 2052 and/or one or more universal serial bus ("USB") devices 2054 via one or more USB interfaces 2056. In an exemplary embodiment, data such as data pertaining to operations of the device and/or software updates may be transferred via the USB interface 2056, for example.

Some exemplary embodiments may provide network communication capabilities, such as by including an Ethernet port 2056A through which the device may be connected to a network, such as a local area network. Data transfer for any purpose may be accomplished via the network, such as providing software updates, transferring data pertaining to operations of the device, and/or transmitting error codes, for example.

An exemplary embodiment may include an input/output (I/O) board 2058 which may be operatively connected to main processor 2050 and/or which may receive signals from one or more sensors, such as IR temperature sensors 338, 340, 342. I/O board 2058 may be operatively connected to one or more switches associated with certain conditions, such as bubble detector 132 and/or leakage detector 2060, which may be associated with trough 309C. I/O board 2058 may receive signals from one or more sensors, such as load cells 142, 144, 206A, 206B, 206C, 206D and/or pressure sensors 2068, 2070.

Some exemplary embodiments may include various safety switches, such as cabinet over-temperature switch 2062A (which may detect a high temperature condition in fluid management unit 100), current sensor 2062B (which may sense whether electrical current is flowing to IR lamps 312, 314, 316, 318), blower-on switch 2062C (which may sense whether blower 309A is running), canister connected switch 2062D (which may sense whether suction container hanger assembly 200 is present), and/or fan-on switch 2062E (which may sense whether chassis fan 2018 is running).

In some exemplary embodiments, fluid management unit 100 may be user selectable between a pressure control mode and a flow control mode. In an exemplary pressure control mode, pump 112 may be controlled (e.g., started, stopped, and its speed adjusted) to maintain a fluid pressure delivered to a surgical site at about a target pressure and/or within a predetermined pressure band. In an exemplary flow control mode, pump 112 may be controlled (e.g., started, stopped, and its speed adjusted) to deliver fluid to a surgical site at a about target flow rate and/or within a predetermined flow rate band. In both pressure and flow control modes, heater assembly 309 may be controlled (e.g., IR lamps 312, 314, 316, 318 may be energized, deenergized, and/or the power level supplied to IR lamps 312, 314, 316, 318 may be adjusted) to maintain the temperature of the fluid delivered to the surgical site at about a target temperature and/or within a predetermined temperature band if the fluid warming feature has been enabled by the user.

Figure 21:
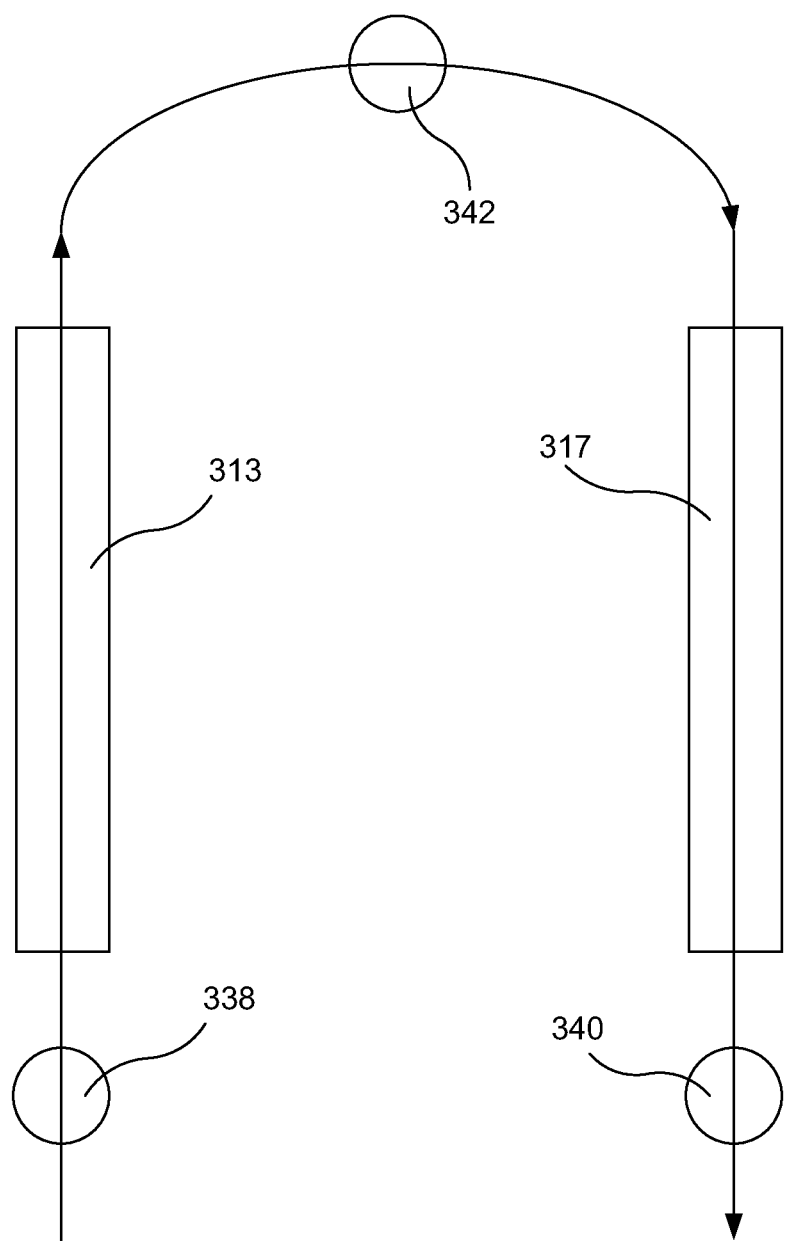
FIG. 21 is a schematic illustration of an exemplary equipment setup utilizing multi-stage heating.

FIG. 21 is a schematic diagram of an exemplary equipment setup utilizing multi-stage heating. In an exemplary embodiment, one or more of IR lamps 312, 314, 316, 318 may be controlled in association with one or more others of IR lamps 312, 314, 316, 318. For example, IR lamps 312, 314 may comprise a first group 313, and IR lamps 316, 318 may comprise a second group 317. In an exemplary embodiment, fluid may flow past the IR lamps associated with one group prior to flowing past the IR lamps associated with a second group, and the first and second groups may be controlled independently. For example, the fluid flow path in cartridge 410 including channels 420, 432, 434, 422 (in that order) may direct fluid past lamps 312, 314, 316, 318 (in that order).

In an exemplary embodiment, the first group 313 may be control based at least in part on a sensed inlet temperature (such as sensed by temperature sensor 338), and the second group 317 may be controlled based at least in part on a sensed temperature of the fluid between the first and second groups, which may be referred to as a midpoint temperature (such as sensed by temperature sensor 342), and/or a sensed outlet temperature (such as sensed by temperature sensor 340). An outlet temperature, which may be the temperature of the fluid after it has passed the second group (such as sensed by temperature sensor 340), may also be used to vary one or more power scaling factors associated with the power applied to one or more groups of IR lamps.

In some exemplary embodiments, the amount of power applied to one or more stages (e.g., groups 313, 317) may be based at least partially on a flow rate of fluid through heater assembly 309. In some exemplary embodiments, a flow rate may be determined using a known flow rate per rotation of the pump 112 and the rotational speed of the pump 112, for example. In some other exemplary embodiments including other types of positive displacement pumps, the flow rate may be determined in a similar manner. In some exemplary embodiments, a flow rate sensor may be utilized to measure a flow rate.

Some exemplary embodiments may be configured to account for one or more of the following conditions: variations in incoming fluid temperature during a procedure, variations in flow rate to maintain constant pressure, changes to temperature set point by the user, interruptions and/or changes in flow rate during a procedure caused by opening/closing of external valves (e.g., trumpet valves, valves in surgical instruments, etc.), and/or resuming warming when stopped flow resumes.

In some exemplary embodiments, the first group 313 may be powered based at least in part upon an estimated power requirement, which may be directly proportional to a total desired temperature change of the fluid (e.g., outlet temperature minus inlet temperature) and/or a flow rate of the fluid. In some example embodiments, the estimated power requirement may be multiplied by a load factor, which may determine a fraction of the estimate power that is to be delivered to the first group. In some exemplary embodiments, the first group may be deenergized whenever pump 112 is stopped.

In some exemplary embodiments, the second group 317 may be powered based at least in part upon a proportional control algorithm and/or an integral control algorithm. In an example proportional control algorithm, the estimated power may be multiplied by a proportional factor whose value varies with the temperature error (desired outlet temperature−current outlet temperature). For example, the proportional factor may be given by $$1.1 + \frac{\text{temperature\_error}^2}{400}.$$

In some exemplary embodiments, the constants may be selected such that the desired outlet temperature may be achieved reasonably quickly with limited overshoot. In addition, some constants may be selected to at least partially compensate for older lamps that may have begun to exhibit performance degradation. In an exemplary embodiment, the value of 1.1 results in a power at the desired outlet temperature that is about 10% above the estimated power. In an exemplary embodiment, the value of 400 ($20^2$) may be based on the notion that an expected initial error may be on the order of 20° C. which would result in proportional factor of 2.1.

In an example integral control algorithm, the power applied to the second group 317 may be adjusted in small increments (e.g., about 1% per increment) based on the integral of the temperature error. For example, if the integral of the temperature error is less than a predetermined negative value (e.g., fluid temperature is high), the power applied to the second group may be reduced by one increment. Similarly, if the integral of the temperature error is greater than a predetermined positive value (e.g., fluid temperature is low), the power applied to the second group 317 may be increased by one increment. The predetermined negative value and the predetermined positive value may vary based at least in part upon the flow rate of the fluid.

Some example embodiments may provide a pressure curve override, which may reduce heating when the pump 112 is running but little or no fluid is flowing. For example, if the irrigation valve on a trumpet valve is rapidly shut, pump 112 may continue to run until the fluid reaches a predetermined maximum pressure. In such a situation, it may be desirable to reduce the power supplied to the second group 317, or to deenergize the second group entirely. For example, if the sensed pressure increases at a rate in excess of 2 mmHg/second, the second group 317 may be deenergized.

Algorithm selection may be based at least in part upon the current deviation from the desired outlet temperature. For example, when the current outlet temperature is substantially below the desired outlet temperature, the proportional control algorithm may be used. As the current outlet temperature approaches the desired outlet temperature, integral control may be used. At some temperature deviations, a power reduction factor may be applied to reduce the power supplied to the second group 317 to prevent overshooting the desired outlet temperature. In some exemplary embodiments, the power reduction factor may vary from about 1.0 (no reduction) down to about 0 (no power applied) as the current outlet temperature reaches and/or exceeds the desired outlet temperature.

In an exemplary embodiment, pulse width modulation may be employed to vary the power applied to one or more IR lamps 312, 314, 316, 318. For example, processor 2050, via I/O board 2058 and/or isolation board 2034, may direct SSRs 2076, 2078 to selectively energize and deenergize first group 313 and/or second group 317. The duty cycle (e.g., the ratio of on time to the sum of the on and off times in an on/off cycle) may be varied to deliver more or less power to the first group 313 and/or second group 317 as desired. More specifically, if it is desired to increase the amount of power delivered to first group 313, the first group's duty cycle may be adjusted by causing SSR 2076 to increase the on time and reduce the off time in each on/off cycle. Similarly, if it is desired to reduce the amount of power delivered to the second group 317, the second group's duty cycle may be adjusted by causing SSR 2078 to reduce the on time and increase the off time in each on/off cycle.

Some exemplary embodiments may utilize pressure control modes for distention applications, and some pressure control modes may be referred to as distention modes although the fluid is likely being used for both distention (body cavity expansion) and irrigation (blood and debris removal) purposes. Some exemplary embodiments may utilize flow control modes for irrigation applications, and some flow control modes may be referred to as irrigation modes.

Figure 22:
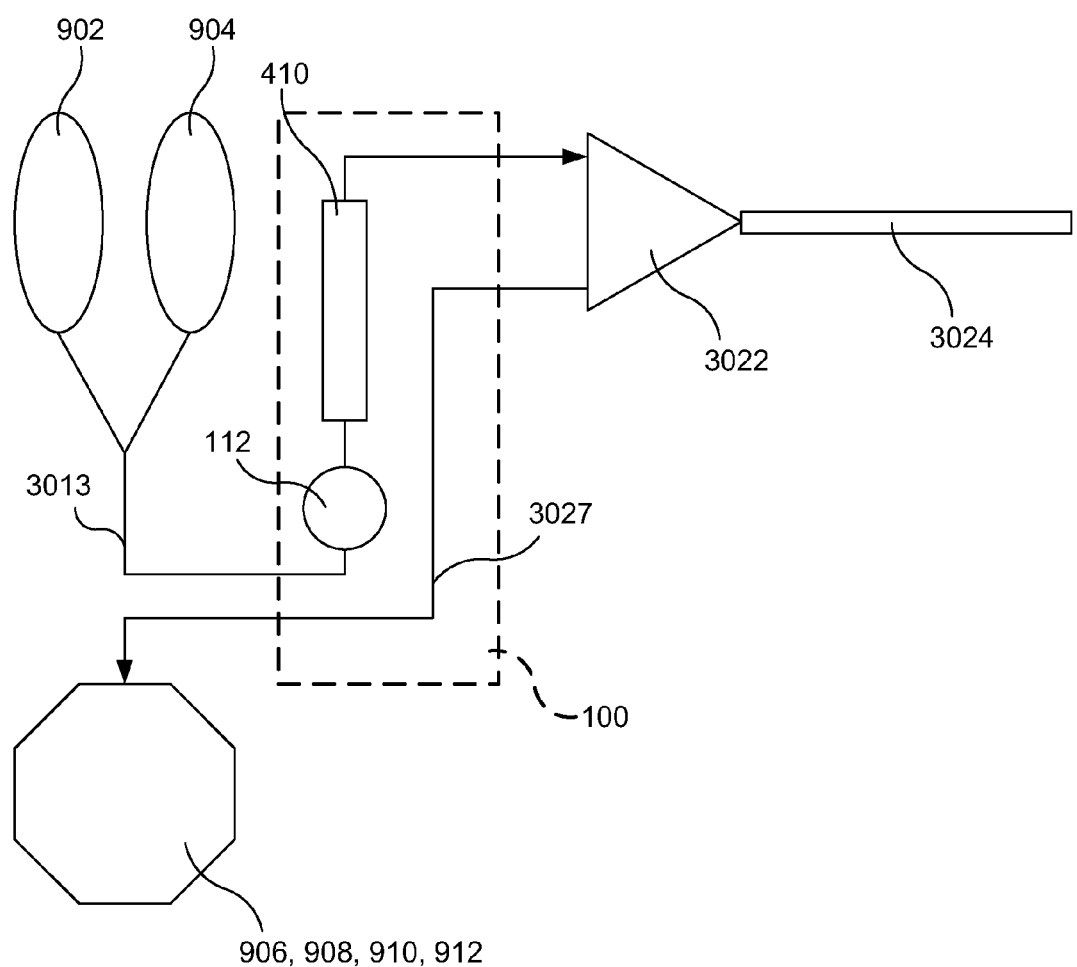
FIG. 22 is a schematic diagram of an exemplary equipment setup for use with a trumpet valve.

FIG. 22 is a schematic diagram of an exemplary equipment setup for use with a trumpet valve. In an exemplary embodiment, irrigation tubing 3013 may extend through pump 112 such that pump 112 is operative to pressurize and/or propel liquid in irrigation tubing 3013.

Figure 23:
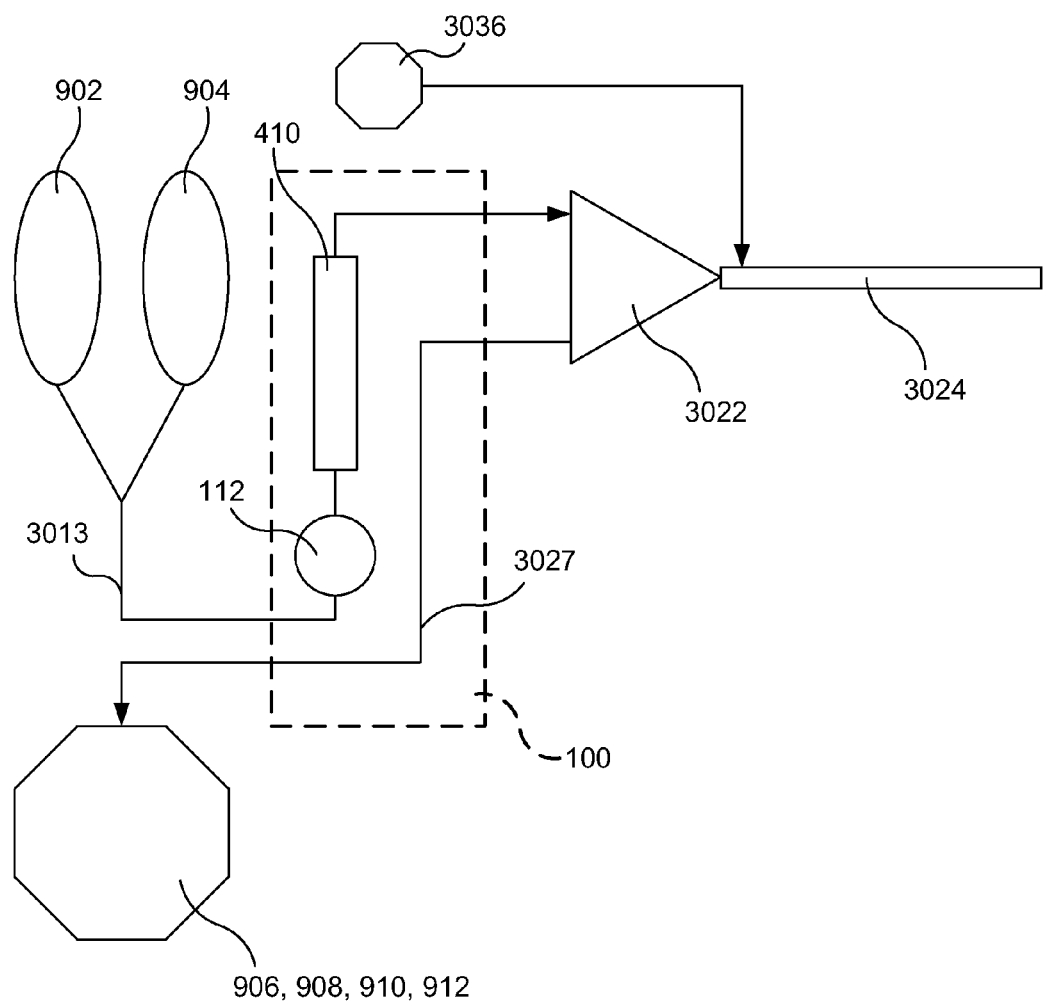
FIG. 23 is a schematic diagram of an exemplary equipment setup for use with an electrosurgical device.

FIG. 23 is a schematic diagram of an exemplary equipment setup for use with an electrosurgical device. In some exemplary embodiments, an electrosurgical tip 3024 may receive electrical power from an external power source 3036, such as an electrosurgical generator.

Figure 24:
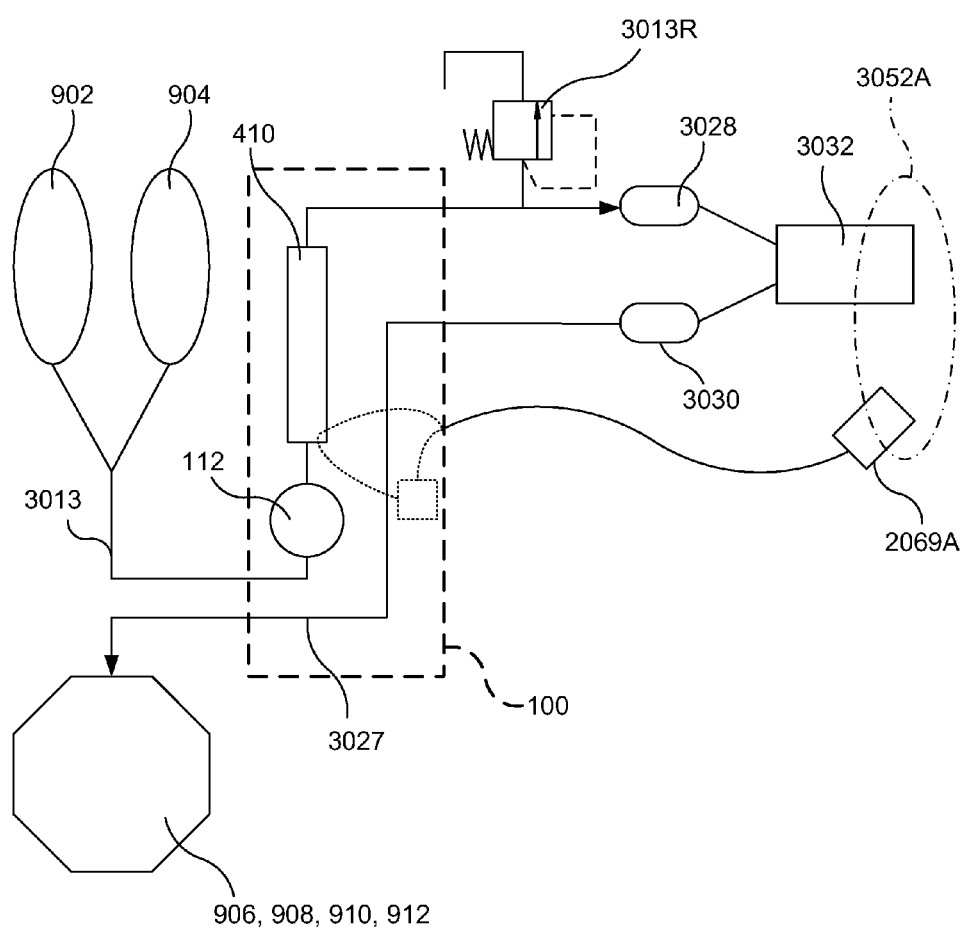
FIG. 24 is a schematic diagram of an exemplary equipment setup for use with a tubing set including one or more connectors for connecting to a surgical instrument.

FIG. 24 is a schematic diagram of an exemplary equipment setup for use with a tubing set including one or more connectors 3028, 3030 for connection to one or more surgical instruments 3032. For example, Luer connectors may be provided. Exemplary surgical instruments which may be utilized with exemplary fluid management units 100 may include arthroscopes, hysteroscopes, and/or cystoscopes, and the like. Similar devices may be employed in other procedures, such as transurethral resection of the prostate (TURP). The present disclosure contemplates that other surgical instruments known in the art may be utilized in connection with various exemplary embodiments.

Any tubing set and/or equipment setup used in connection with exemplary fluid management units 100 according to the present disclosure may include one or more relief valves. For example, one or more relief valves 3013R may be fluidicly connected in and/or to irrigation line 3013 downstream of pump 112. In such embodiments, if the fluid pressure downstream of pump 112 exceeds the set pressure of the relief valve 3013R for any reason, including a failure in fluid management system 100, the relief valve 3013R may discharge fluid until the fluid pressure falls below the re-seat pressure of the relief valve 3013R. Such a pressure relief valve 3013R may be completely independent of the microprocessor-based control system for fluid management unit 100 and, therefore, may comprise a substantially redundant safety mechanism.

Some exemplary embodiments may include one or more remote pressure sensors 2069A. For example, a remote pressure sensor 2069A may be placed at least partially in a body cavity 3052A being distended, such as a uterus or a bladder, and such remote pressure sensor 2069A may provide a pressure signal to fluid management unit 100. For example, a remote pressure sensor 2069A located in a body cavity being distended may provide an electrical (e.g., analog and/or digital) and/or pneumatic signal indicative of fluid pressure within the cavity. Such analog, digital, and/or pneumatic signal may be conveyed to fluid management unit 100 directly and/or via the heating cartridge 410. Fluid management unit 100 may use such signal from remote pressure sensor 2069A indicating fluid pressure in the body cavity 3052A being distended in place of, or in addition to, the signal indicating fluid pressure in cartridge 410 to control fluid pressure at the desired level selected by the user and, if necessary, to trigger alarms or shut down the pump 112 to prevent unsafe conditions.

Figure 25:
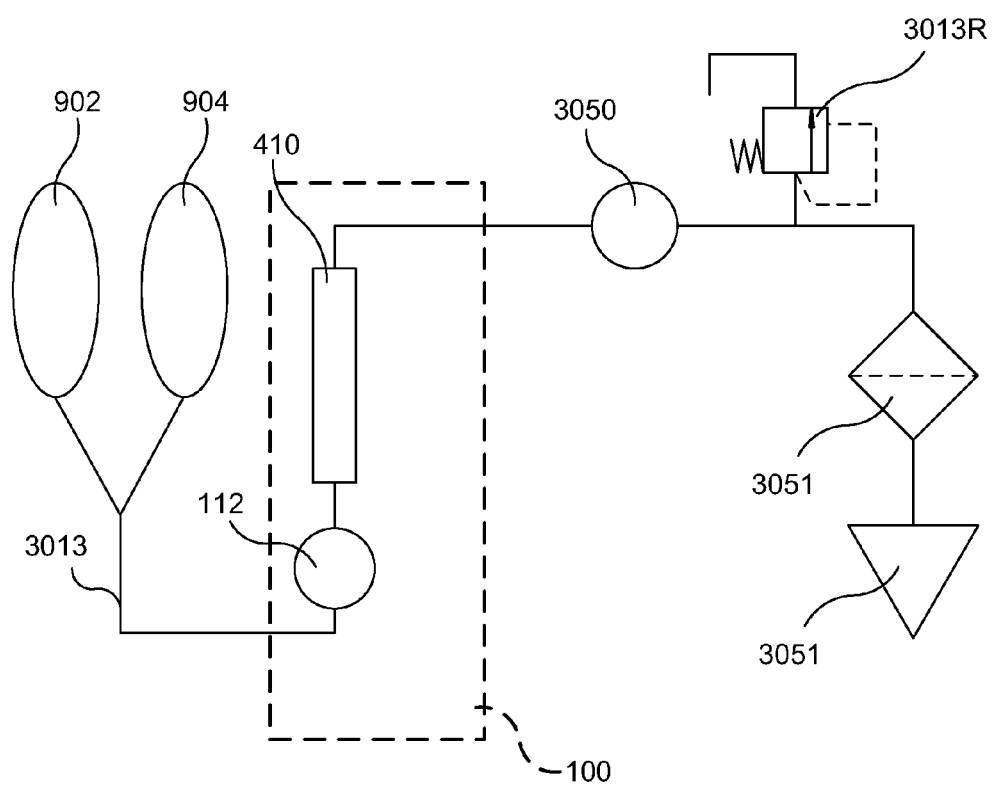
FIG. 25 is a schematic diagram of an exemplary equipment setup for infusion.

FIG. 25 is a schematic diagram of an exemplary equipment setup for infusion. Such a device may be utilized with any fluids to be infused into a patient, including pharmaceuticals and/or blood components. Some exemplary embodiments may include one or more bubble detectors 132 (FIG. 2) within unit 100 and/or one more bubble detectors 3050 external to fluid management unit 100. In some exemplary embodiments, the fluid may be gravity fed, and the tubing may bypass pump 112. In some exemplary embodiments, an in-line filter 3051 may be employed, such as when blood is being infused. Such tubing sets used for infusion may also include a pressure relief valve 3013R to reduce the likelihood of infusing fluids into a patient at excess pressures for any reason, including a failure of fluid management system 100.

Figure 26:
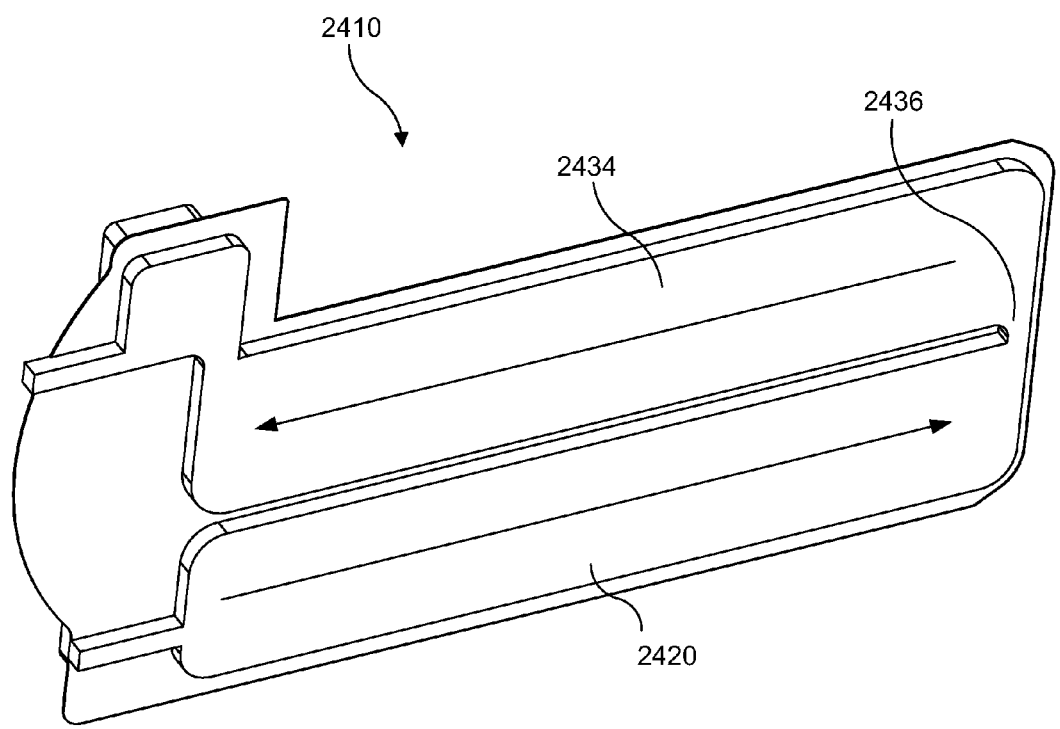
FIG. 26 is a perspective view of an alternative exemplary heating cartridge.
Figure 27:
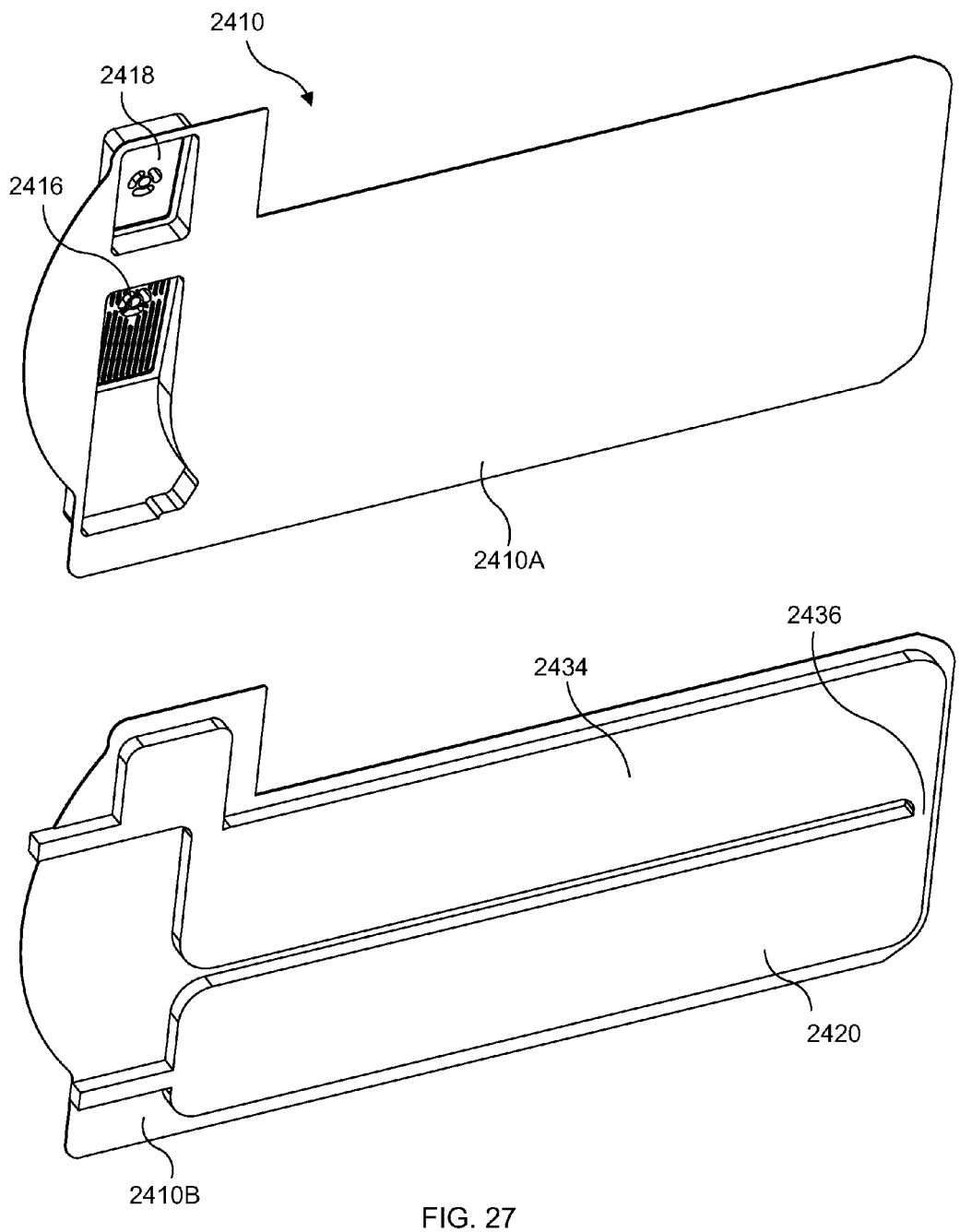
FIG. 27 is an exploded perspective view of an alternative exemplary heating cartridge.

FIGS. 26 and 27 illustrate an alternative example cartridge 2410. Cartridge 2410 may be generally similar to cartridge 410, except that cartridge 2410 may include a two-dimensional fluid flow path. Specifically, in some example embodiments, fluid may enter cartridge 2410 at an inlet fitting which may be generally similar to inlet fitting 412, may flow past bubble trap 2416, and into lower fluid channel 2420. Then, fluid may generally reverse direction in turn section 2436 and may flow into upper fluid channel 2434. Fluid may then flow past bubble trap 2418 and out of cartridge 2410 via an outlet fitting which may be generally similar to outlet fitting 414. Cartridge 2410 may include any other features discussed herein with reference to cartridge 410, such as fitting 2430.

Some example cartridges 2410 may comprise two sections 2410A, 2410B, which may be joined together using adhesive, solvent bonding, ultrasonic bonding, and/or RF welding, or the like. Sections 2410A, 2410B may be constructed by vacuum forming thin plastic to form the desired features. Unlike cartridge 410, some exemplary cartridges 2410 may not include a substantially rigid center section. In some exemplary embodiments, one section (e.g., section 2410A) may be flat and/or flatter than another section (e.g., 2410B). For example, certain fluid flow paths and/or fluid channels (lower fluid channel 2420 and/or upper fluid channel 2434) may be formed in one section (e.g., section 2410B) while at least some of the other section (e.g., section 2410A) may be substantially flat and/or configured to lie against section 2410B to form certain features.

An example cartridge 2410 may be configured for use in connection with heater assembly 309 described herein. Accordingly, fluid within cartridge 2410 may be warmed by IR lamps 312, 314, 316, 318. In some example embodiments, lower fluid channel 2420 may be warmed from one side by IR lamp 312 and from the opposite side by IR lamp 314. Similarly, upper fluid channel 2434 may be warmed from one side by IR lamp 318 and from the opposite side by IR lamp 316.

Figure 28:
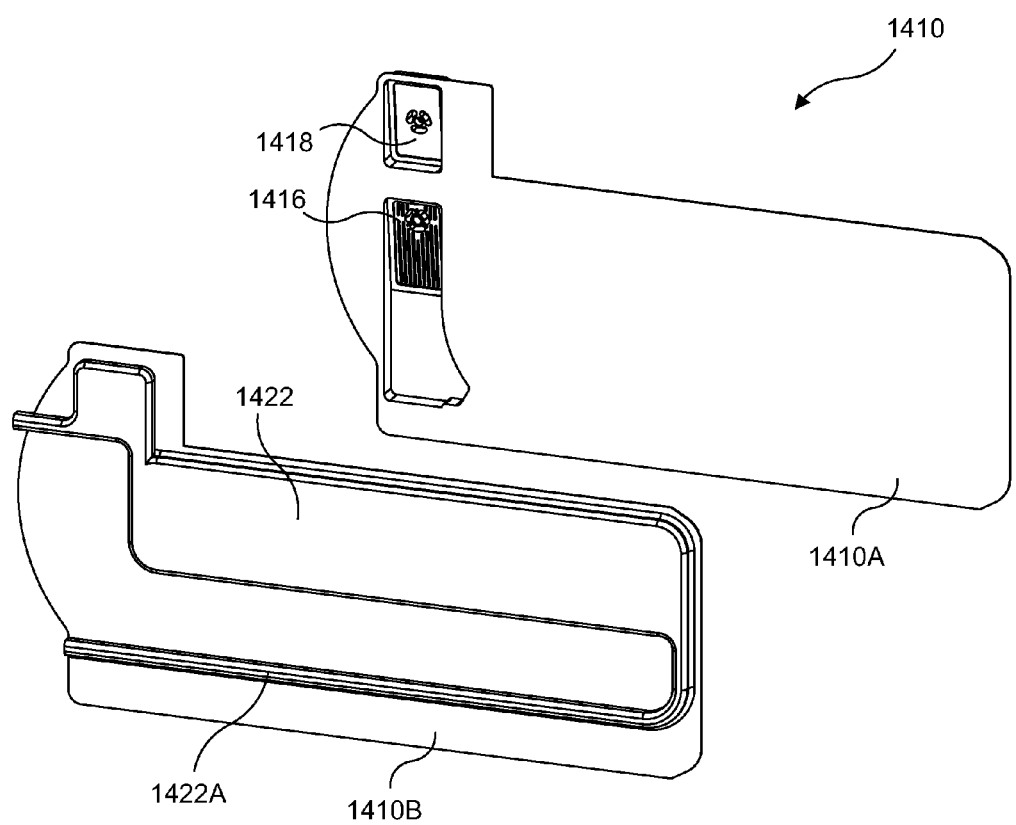
FIG. 28 is an exploded perspective view of an alternative exemplary heating cartridge.

FIG. 28 illustrates an alternative example cartridge 1410. Similar to cartridge 2410 described above, some example cartridges 1410 may comprise two sections 1410A, 1410B. In some exemplary embodiments, section 1410A may include bubble traps 1416, 1418, which may be generally similar to bubble traps 416, 418 described above. In some exemplary embodiments, cartridge 1410 may include one or more fluid channels 1422 to which fluid may be supplied to or discharged from via one or more fluid conduits 1422A. Some exemplary fluid conduits 1422A may be formed in one or more of sections 1410A, 1410B in a manner similar to fluid channel 1422. In some exemplary embodiments, fluid may enter cartridge 1410 through in inlet fitting generally similar to inlet fitting 412, flow through bubble trap 1416, flow through fluid conduit 1422A, flow through fluid channel 1422, flow through bubble trap 1418, and/or may exit cartridge 1410 via an outlet fitting generally similar to outlet fitting 414. Some exemplary cartridges 1410 may include a pressure tap and/or fluid path generally similar to those of cartridge 410.

In some exemplary embodiments, only one or more IR lamps 312, 314, 316, 318 may be used in connection with cartridge 1410. For example, upper lamps 316, 318 may be used in connection with cartridge 1410, while lower lamps 312, 314 may remain deenergized. Some exemplary fluid management units 100 may be configured for such operations by entry of a part number corresponding to the cartridge type by a user.

Some exemplary cartridges 1410 may have a lower internal volume that cartridge 410 described above, which may utilize a smaller volume of fluid for priming than cartridge 410. Some exemplary cartridges 1410 may provide relatively lower fluid flow rates than some exemplary cartridges 410. Thus, some exemplary cartridges 1410 may be used in place of some exemplary cartridges 410 in some procedures in which lower fluid flow rates may be expected.

Some exemplary embodiments may include a remote control device, such as a pneumatic remote control device. For example, a pneumatic signal may be produced by a pneumatic actuator (such as a bulb, button, bellows, piston, or the like), which may be mounted near or on, or integrated with a hand piece and/or surgical instrument. The pneumatic signal may be conveyed to the fluid management unit 100. For example, a the pneumatic signal may be conveyed via tubing extending from the pneumatic actuator to a fitting on a cartridge, through a passage in the cartridge, and to a pressure transducer (or other device capable of producing an electrical signal based at least partially upon the pneumatic signal) via a fitting which releasably engages a corresponding fitting in heater assembly 309. As another example, a pneumatic signal may be conveyed via tubing extending from the pneumatic actuator, to a fitting on fluid management unit 100, and to a pressure transducer (or other device capable of producing an electrical signal based at least partially upon the pneumatic signal). The pneumatic signal may be utilized to cause an adjustment in a desired pressure, flow rate, or other operating parameter, for example. Such an adjustment may be a momentary or a sustained incremental adjustment, for example.

Some exemplary embodiments may provide a perforation alarm, which may be particularly useful in hysteroscopic procedures and the like, for example. An exemplary perforation alarm may be based on an increased rate of change of the deficit. For example, an alarm may be triggered when the deficit is increasing at a rate in excess of 200 mL/min. In exemplary embodiments, the set point of one or more perforation alarms may be programmed by a user.

Some exemplary embodiments may be capable of warming fluids from a storage temperature to an appropriate temperature for use without pre-warming in a warming cabinet, for example.

Some exemplary embodiments may include a user interface allowing a user to specify a particular type of tubing set that is being utilized. In some exemplary embodiments, the device may automatically determine a particular type of tubing set that is being installed by, for example, using one or more bar codes (or other optical codes), radio-frequency identification (RFID) transponders, color-coding, and the like. In some exemplary embodiments, default parameters may be automatically set based upon a sensed tubing set type.

Some exemplary embodiments may include a user-configurable interface, which may be provided using touch screen 106. In exemplary embodiments, user may be able to specify the data (such as temperature, pressure, flow rate, deficit, etc.) that are displayed, and may be able specify a manner of display (e.g., numeric value, graphical representation of a single value or a value over time, etc.). In some exemplary embodiments, the user interface may be adapted to provide instructions (such as startup instructions, cleaning instructions, and/or operating instructions) to a user via touch screen 106, for example. In some exemplary embodiments, a language used on a display may be user-selectable. In some exemplary embodiments, the touch screen interface may be configured to display error codes, conditions, and/or descriptions and may also be configured to display preventative maintenance notifications.

Figure 29:
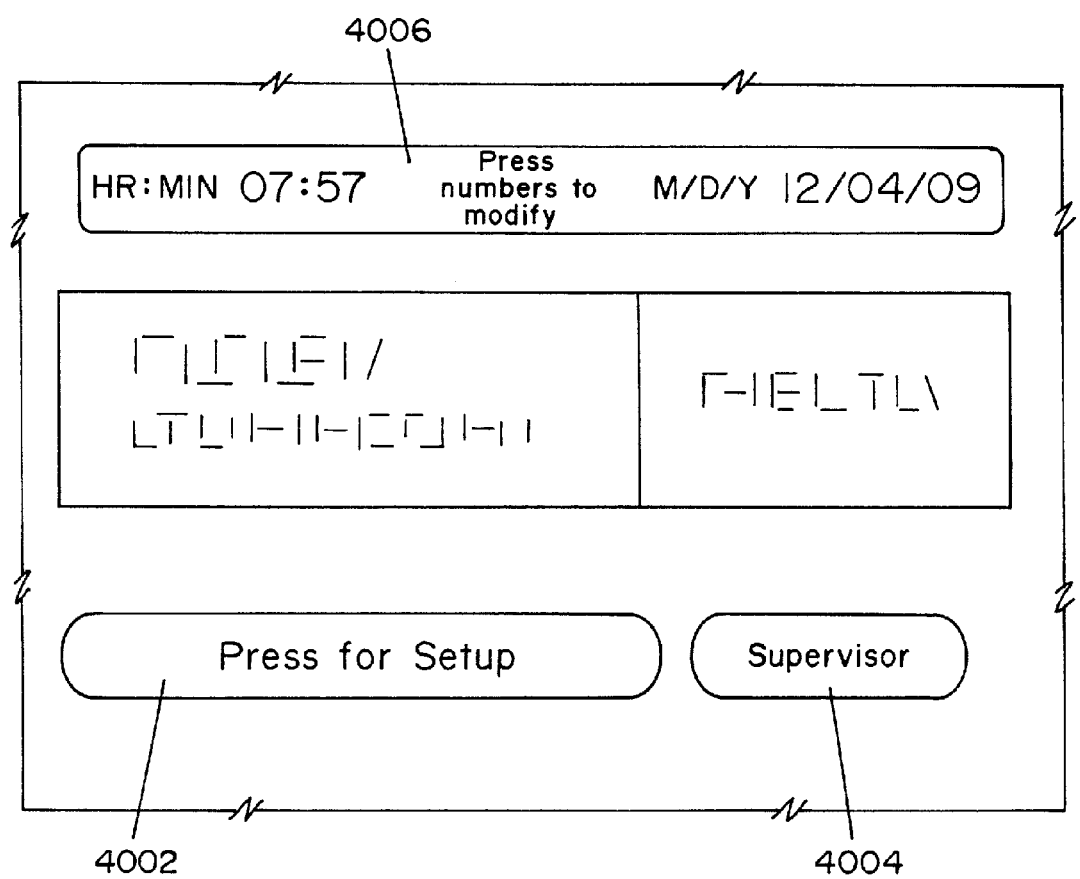
FIG. 29 is a screen shot of an exemplary setup screen.

FIGS. 29-40 are screen shots of an exemplary touch screen 106. These screen shots are described with reference to "buttons," which may comprise portions of touch screen 106 configured to appear like buttons and/or which may provide functionality similar to physical buttons. FIG. 29 illustrates an example setup screen, which may include a setup button 4002, a supervisor mode button 4004, and/or a date/time display 4006. Setup button 4002 may be used to initiate setup of fluid management unit 100 for a procedure, supervisor mode button 4004 may be used to enter a supervisor mode (which is discussed in detail below), and/or the date and/or time may be adjusted using date/time display 4006.

Figure 30:
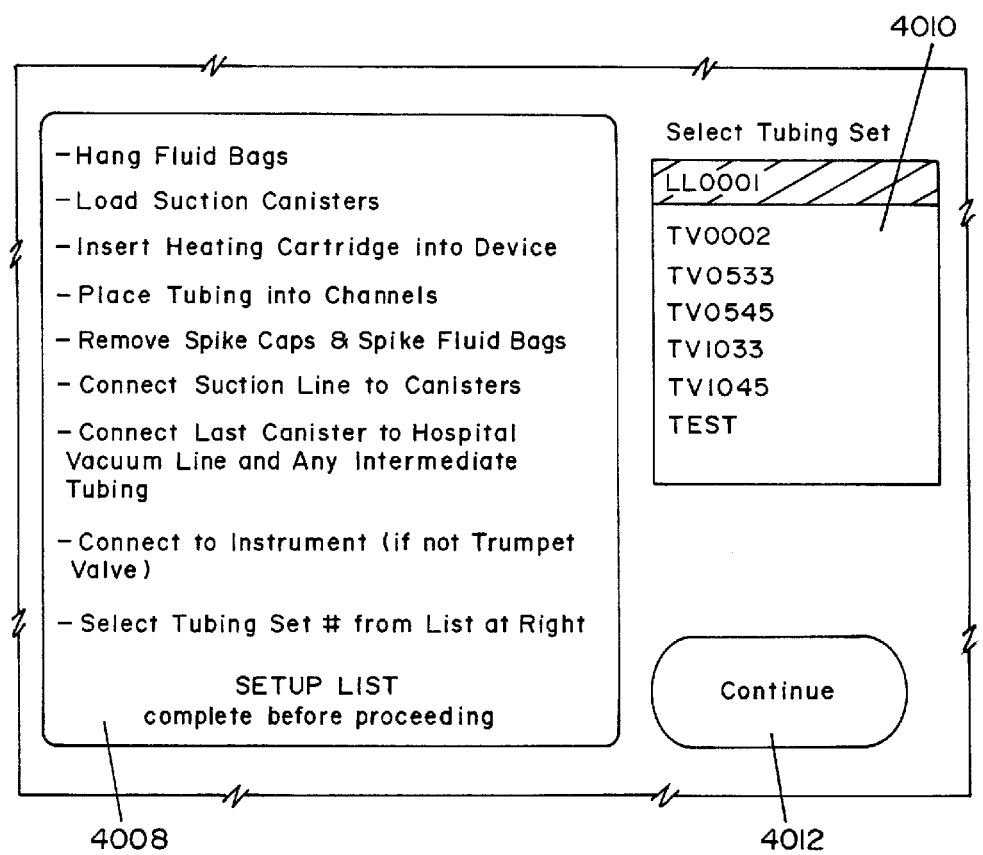
FIG. 30 is a screen shot of an exemplary tubing set selection screen.

FIG. 30 illustrates an exemplary tubing set selection screen, which may include setup instructions 4008, a tubing set list 4010, and/or a continue button 4012. Tubing set list 4010 (which may include one or more tubing set types) and/or continue button 4012 may be used to specify a particular type of tubing set that will be used.

Figure 31:
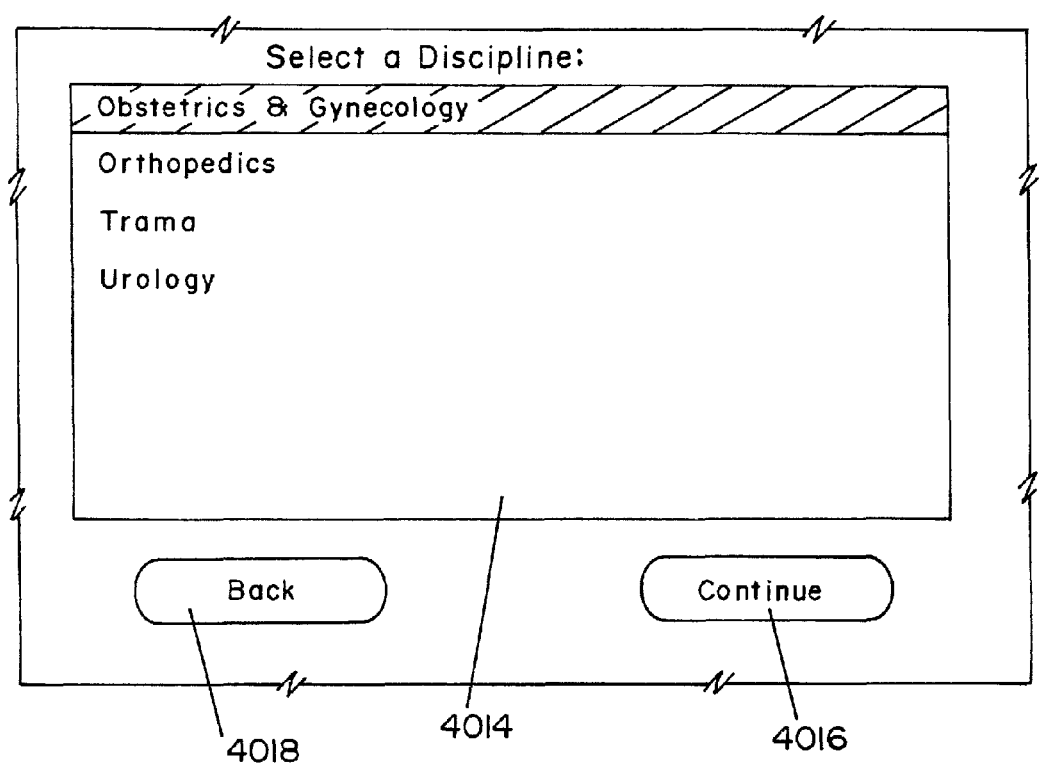
FIG. 31 is a screen shot of an exemplary surgical discipline selection screen.

FIG. 31 illustrates an exemplary surgical discipline selection screen, which may include a discipline list 4014, a continue button 4016, and/or a back button 4018. Discipline list 4014 (which may include one or more surgical disciplines) and/or continue button 4016 may be used to specify a surgical discipline associated with a desired procedure. Discipline list 4014 may be automatically populated based at least in part upon the previously selected type of tubing set. Back button 4018 may return the user to the tubing set selection screen.

Figure 32:
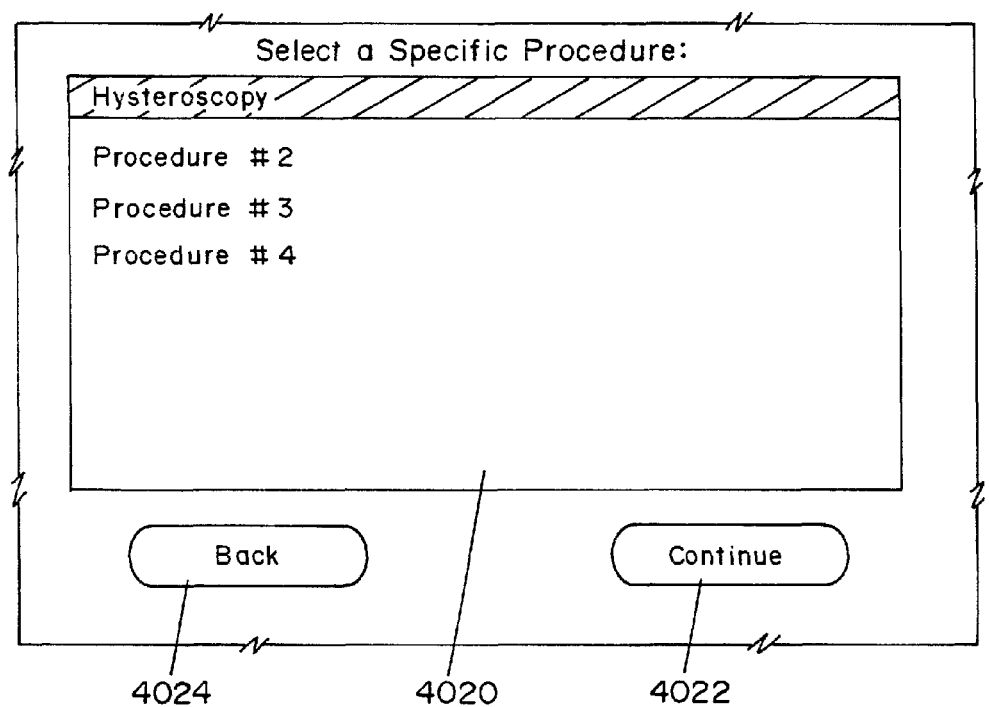
FIG. 32 is a screen shot of an exemplary procedure selection screen.

FIG. 32 illustrates an exemplary procedure selection screen, which may include a procedure list 4020, a continue button 4022, and/or a back button 4024. Procedure list 4020 (which may include one or more procedures) and/or continue button 4022 may be used to specify a desired surgical procedure. Procedure list 4020 may be automatically populated based at least in part upon the previously selected type of tubing set and/or the previously selected surgical discipline. Back button 4024 may return the user to the discipline selection screen.

Figure 33:
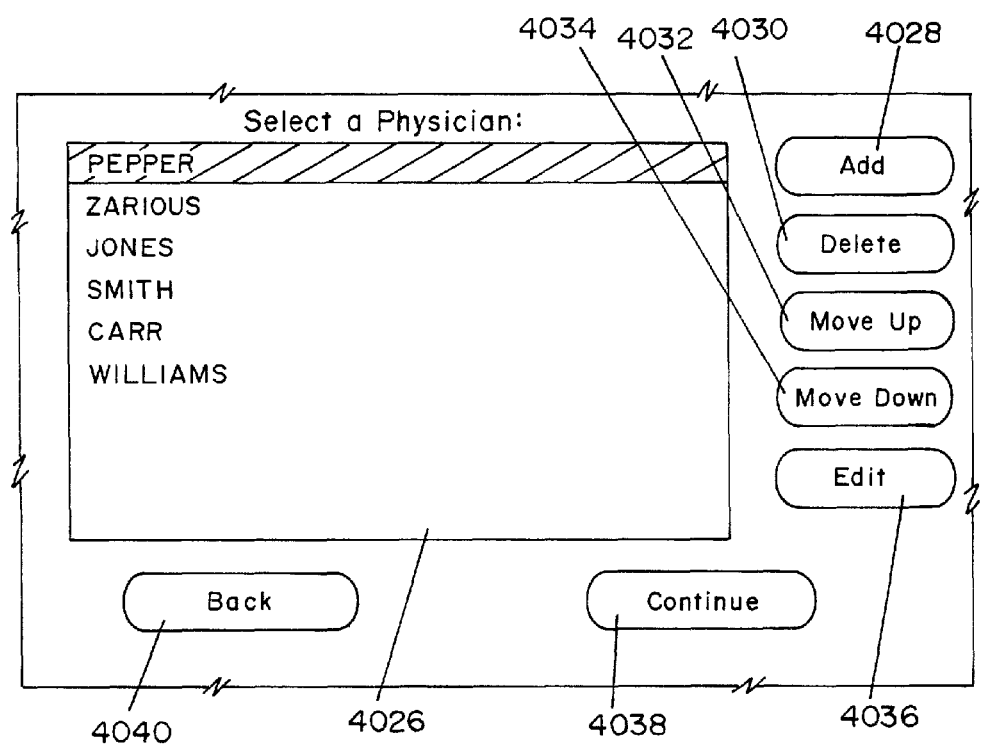
FIG. 33 is a screen shot of an exemplary physician selection screen.

FIG. 33 illustrates an exemplary physician selection screen, which may include a physician list 4026, an add button 4028, a delete button 4030, a move up button 4032, a move down button 4034, an edit button 4036, a continue button 4038, and/or a back button 4040. Physician list 4026 (which may include one or more physicians) and/or continue button 4038 may be used to specify a physician. Physician names may be added to, deleted from, or reordered on physician list 4026 using the add button 4028, the delete button 4030, the move up button 4032, and/or the move down button 4034. Back button 4040 may return the user to the procedure selection screen.

Figure 34:
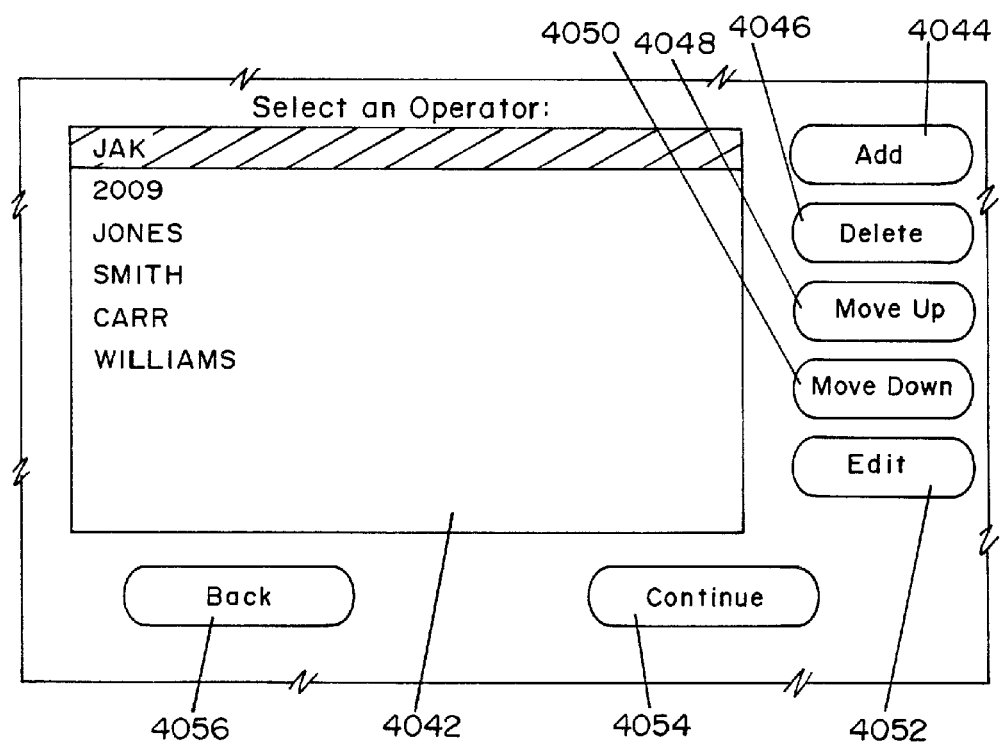
FIG. 34 is a screen shot of an exemplary operator selection screen.

FIG. 34 illustrates an exemplary operator selection screen, which may include an operator list 4042, an add button 4044, a delete button 4046, a move up button 4048, a move down button 4050, an edit button 4052, a continue button 4054, and/or a back button 4056. Operator list 4042 (which may include one or more operators) and/or continue button 4054 may be used to specify a operator. Operator names may be added to, deleted from, or reordered on operator list 4042 using the add button 4044, the delete button 4046, the move up button 4048, and/or the move down button 4050. Back button 4056 may return the user to the procedure selection screen.

Figure 35:
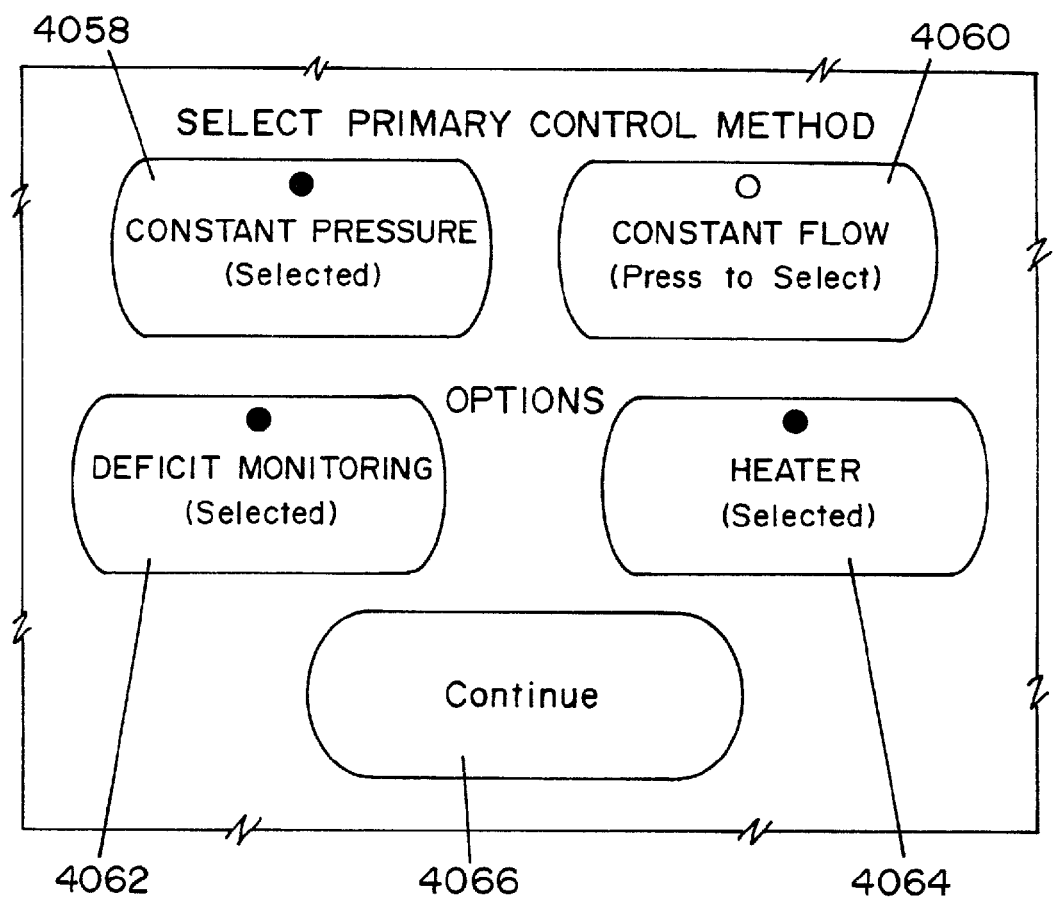
FIG. 35 is a screen shot of an exemplary control mode selection screen

FIG. 35 illustrates an exemplary control mode selection screen. Pressure mode button 4058 and/or flow mode button 4060 may allow toggling between a pressure control mode and a flow control mode. Option buttons, such as deficit monitoring button 4062 and/or heater button 4064 may allow selection of optional functions. Continue button 4066 may advance the interface to the next screen. In some exemplary embodiments, the control mode (e.g., pressure or flow) and/or optional functions may be selected by default based at least in part upon previously entered information. For example, if the entered discipline and procedure utilize pressure mode, the system may assume that pressure mode, deficit monitoring, and/or heater should be enabled. Similarly, if the entered discipline and procedure utilize flow mode, the system may assume that flow mode and/or heater should be enabled and/or that deficit monitoring should be disabled. These defaults may be accepted by pressing the continue button 4066, or the settings may be adjusted as desired prior to pressing the continue button 4066.

Figure 36:
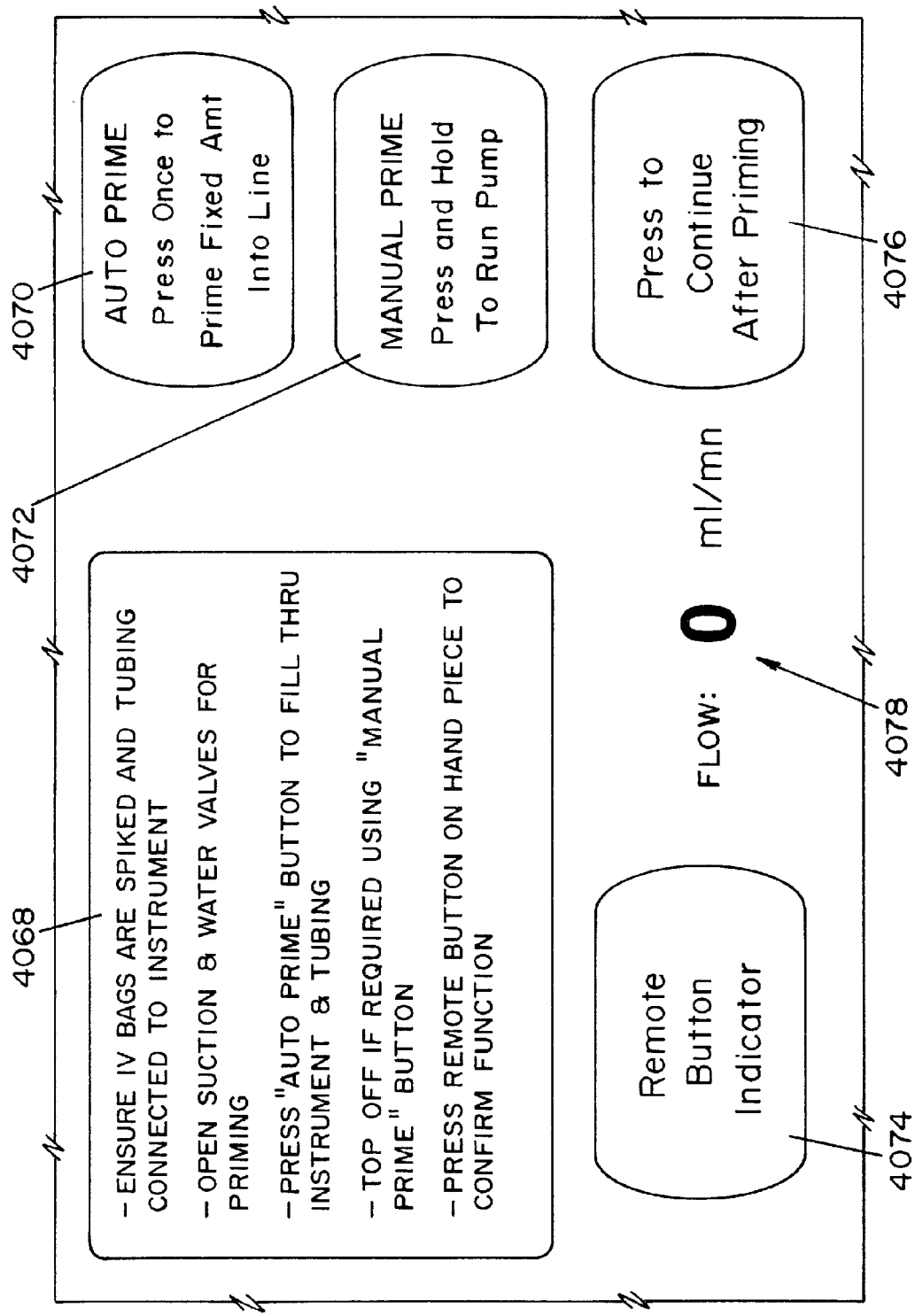
FIG. 36 is a screen shot of an exemplary priming screen.

FIG. 36 illustrates an exemplary priming screen, which may include priming instructions 4068, and automatic prime button 4070, a manual prime button 4072, a remote button indicator button 4074, a continue button 4076, and a flow rate indicator 4078. In some exemplary embodiments, the automatic prime button 4070 may cause pump 112 to run for a predetermined time sufficient to prime tubing set assuming the user has opened the irrigation valve on the trumpet valve or surgical instrument to vent air that would otherwise be trapped in the tubing set, where the predetermined time may vary based upon the tubing set type selected previously. In some exemplary embodiments, the manual prime button 4072 may cause pump 112 to run while it is depressed and pump 112 may stop running when it is released. Manual prime button 4072 may be depressed until fluid has substantially filled the tubing set. In some exemplary embodiments, flow rate indicator may display the current flow rate of fluid.

Figure 37:
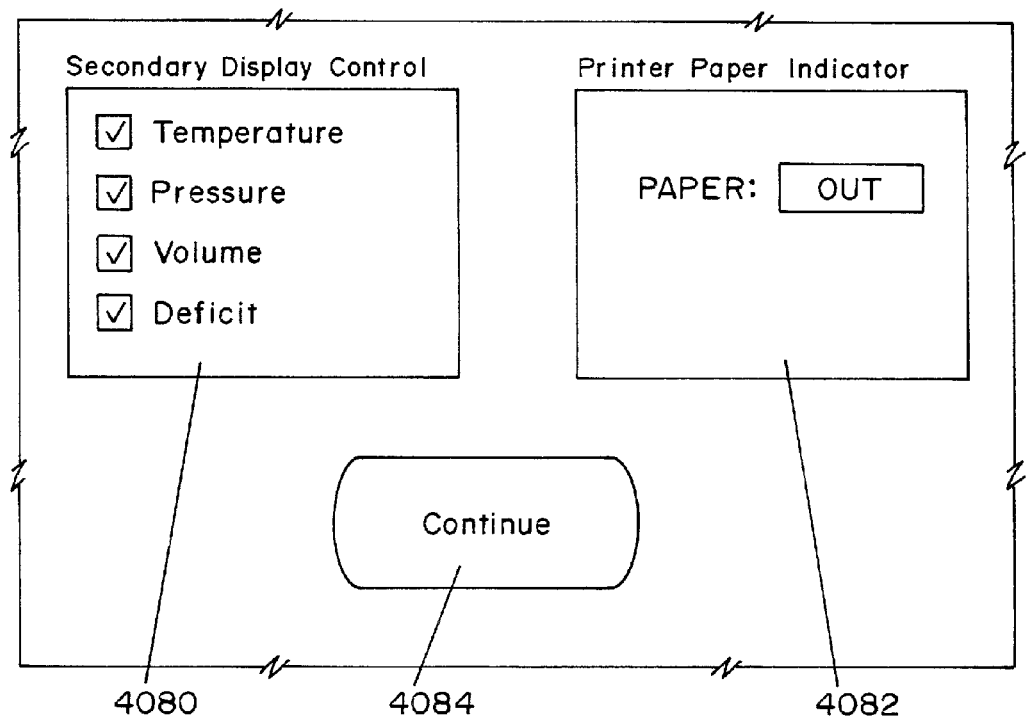
FIG. 37 is a screen shot of an exemplary secondary display and printer control screen.

FIG. 37 illustrates an exemplary secondary display and printer control screen. A secondary display control box 4080 may allow a user to select parameters that will be displayed on secondary display 106A, such as temperature, pressure, volume, and/or deficit. A printer control box 4082 may display information related to printer 111 (e.g., whether printer 111 is out of paper) and/or may allow a user to select information to be printed at the end of a procedure (e.g., temperature, pressure, volume, deficit, and the like). Continue button 4084 may be used to advance to the next screen.

Figure 38:
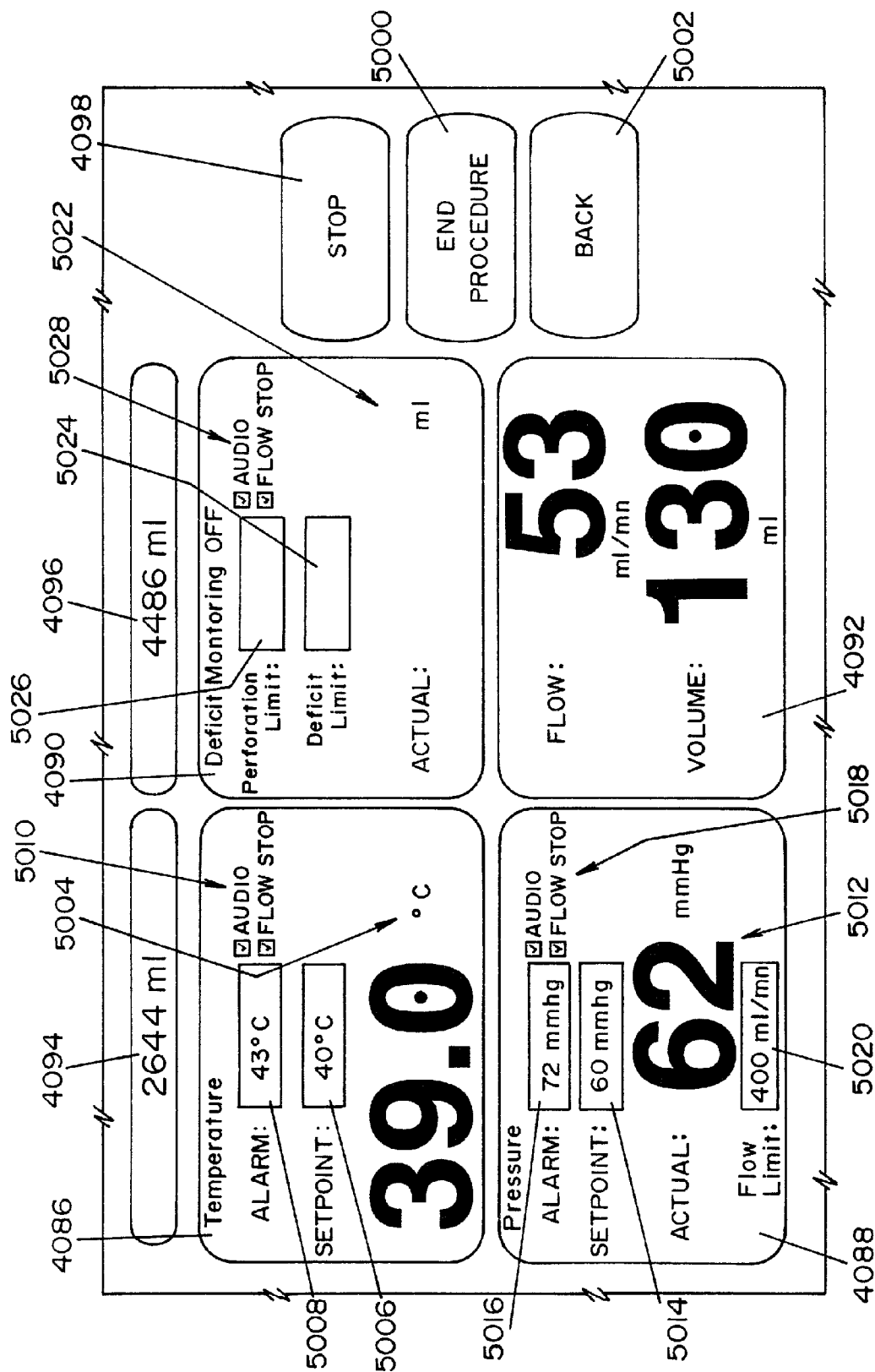
FIG. 38 is a screen shot of an exemplary run screen.

FIG. 38 illustrates an exemplary run screen for a procedure requiring fluid pressure control, which may include a temperature section 4086, a pressure section 4088, a deficit monitoring section 4090, a flow section 4092, a fluid remaining indicator 4094 (which may indicate an approximate amount of fluid remaining in fluid bag 902), a fluid remaining indicator 4096 (which may indicate an approximate amount of fluid remaining in fluid bag 904), a start/stop button 4098, an end procedure button 5000, and/or a back button 5002. An exemplary temperature section 4086 may include current temperature 5004, setpoint temperature 5006 (e.g., target temperature), temperature alarm setpoint 5008, and/or temperature alarm action settings 5010 (e.g., what actions, in addition to a visual alarm, will automatically be taken upon actuation of the temperature alarm, such as sounding an audio alarm and/or stopping fluid flow). An exemplary pressure section 4088 may include current pressure 5012, setpoint pressure 5014 (e.g., a target pressure), pressure alarm setpoint 5016, pressure alarm action settings 5018 (e.g., what actions, which may be in addition to a visual alarm, will automatically be taken upon actuation of the pressure alarm, such as sounding an audio alarm and/or stopping flow), and/or a flow limit 5020 (e.g., a maximum allowable flow rate). An exemplary deficit monitoring section 4090 may include current deficit 5022, deficit alarm limit 5024, perforation alarm limit 5026, and/or perforation alarm action settings 5028 (e.g., what actions will automatically be taken upon actuation of the perforation alarm, such as sounding an audio alarm and/or stopping flow). Start/stop button 4098 may be used to start and/or stop the fluid management unit 100 without terminating the procedure, the end procedure button 5000 may be used to terminate the procedure, and/or back button 5002 may be used to return to the secondary display and printer control screen.

In some exemplary fluid pressure control embodiments, default operating parameters (e.g., one or more of setpoint temperature 5006, temperature alarm setpoint 5008, temperature alarm action settings 5010, setpoint pressure 5014, pressure alarm setpoint 5016, pressure alarm action settings 5018, flow limit 5020, deficit alarm limit 5024, perforation alarm limit 5026, and/or perforation alarm action settings 5028) may be set based at least in part upon the selected discipline and/or selected procedure. In some exemplary embodiments, these operating parameters may be adjusted by touching the corresponding portion of the touch screen 106. Some exemplary embodiments may allow adjustment of these operating parameters up to predetermined maximum limits, which may be associated with safety considerations. If a condition exceeds an operating parameter when the operating parameter is below its respective maximum limit, the resulting alarm may be overridden and operation may continue provided that the maximum limit is not reached. Some exemplary embodiments may stop operation upon reaching a maximum limit, which may not be overridden.

Figure 39:
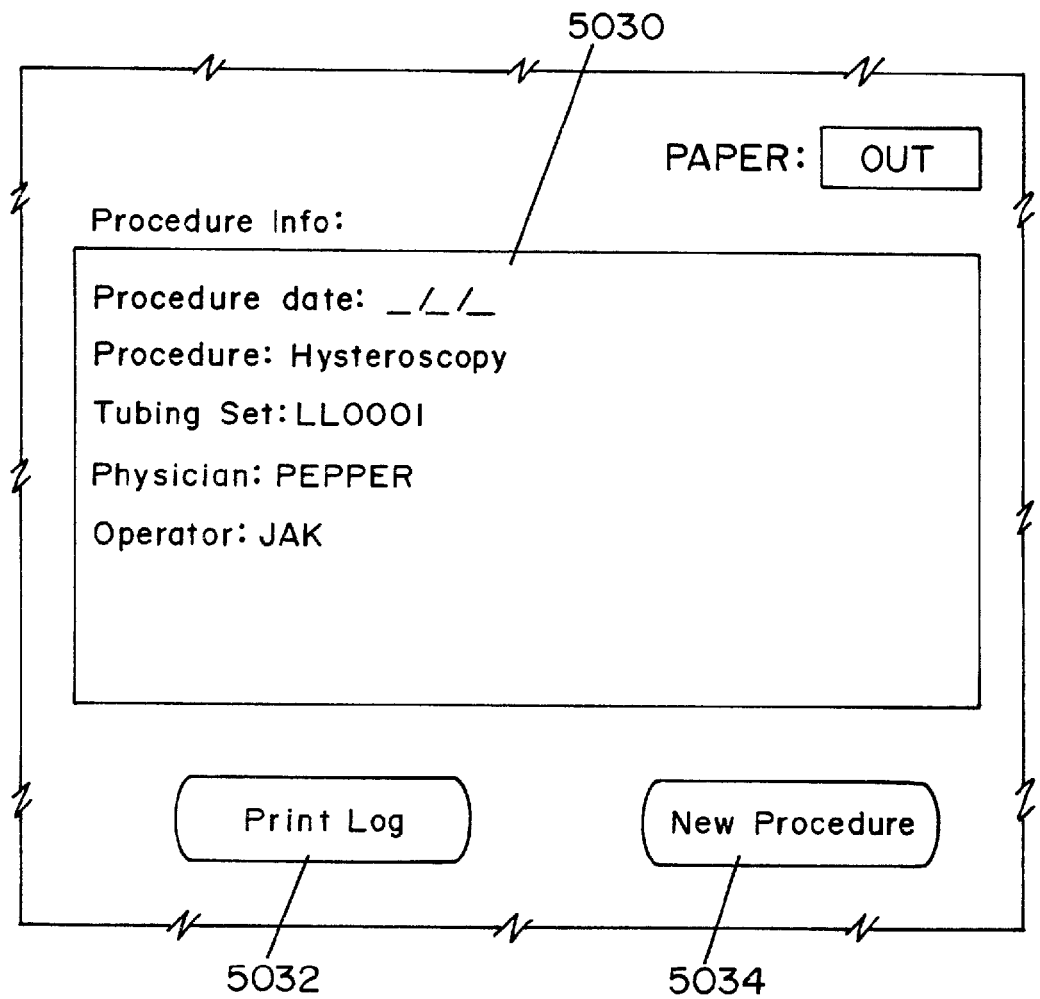
FIG. 39 is a screen shot of an exemplary summary screen.

FIG. 39 illustrates an exemplary summary screen, which may display procedure information 5030. A print button 5032 may cause printer 111 to print the procedure information 5030. A new procedure button 5034 may return the user to the setup screen described above to prepare fluid management unit 100 for use in a new procedure.

Figure 40:
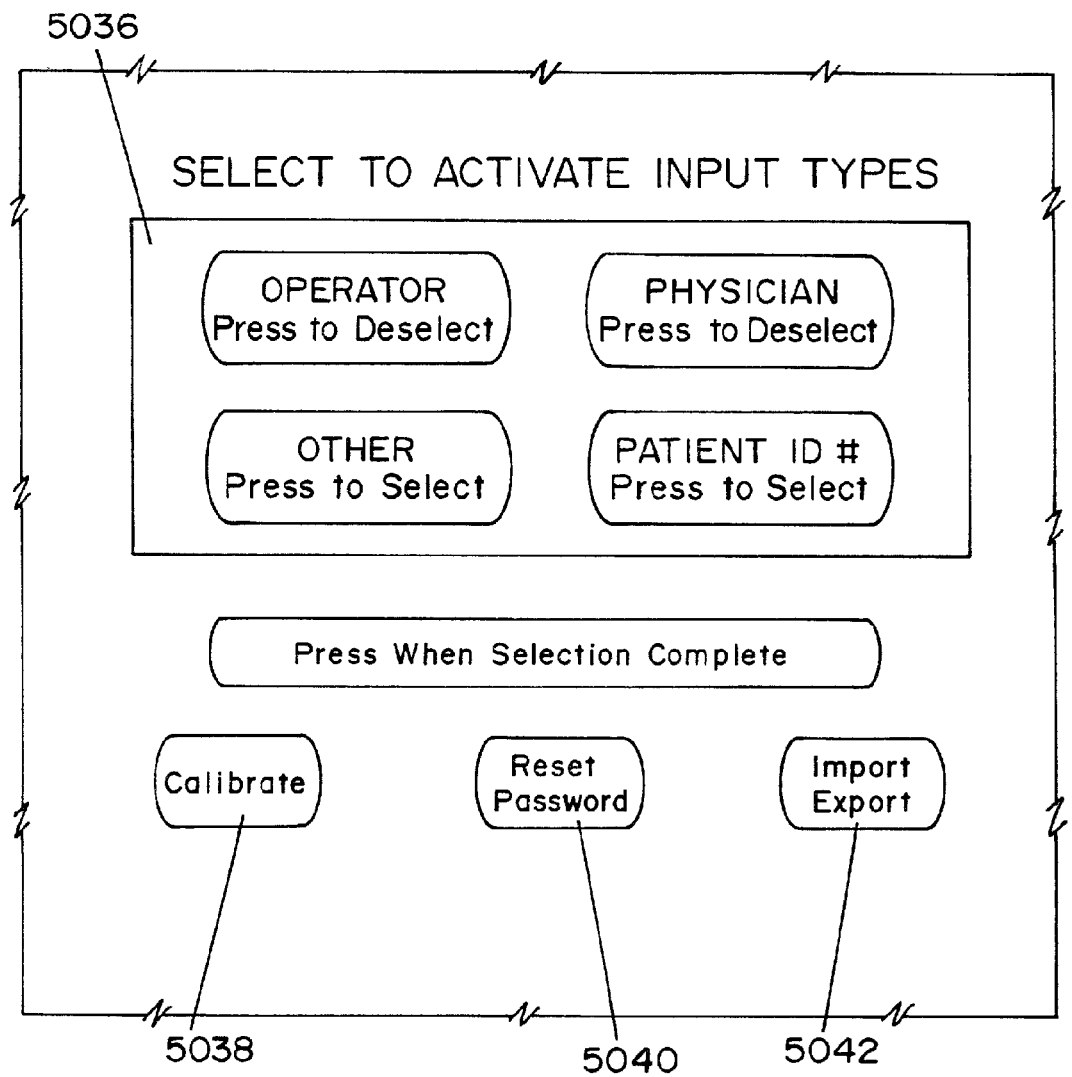
FIG. 40 is a screen shot of an exemplary supervisor screen.

FIG. 40 illustrates an exemplary supervisor screen, which may include an input type selection section 5036. Input type selection section 5036 may allow a supervisor to select information that will be gathered during the setup process. For example, physician and/or operator identities may be gathered as described above. Similarly, patient identifying information and/or other information may be gathered in a similar fashion. An exemplary supervisor screen may allow a supervisor to perform other functions, such as calibrating one or more of load cells 142, 144, 206A, 206B, 206C, 206D via calibrate button 5038, resetting a password via password reset button 5040, and/or importing or exporting data via import/export button 5042.

An exemplary embodiment may be operated as follows. An operator may hang one or more fluid bags 902, 904 on one or more of fluid bag hangers 102, 104. The operator may install one or more suction canisters 906, 908, 910, 912 into suction canister hanger 202. The operator may connect a tubing set (e.g., trumpet valve tubing set 3010) to the fluid bags 902, 904, load a section of tubing into pump 112, load cartridge 410 into heater assembly 309, load a section of irrigation tubing 3013 into path 124, connect suction tubing 3027 to one or more suction canisters 906, 908, 910, 912, and shut door 108. The operator may then utilize touch screen 106 to set up the fluid management unit 100, which may include selecting the tubing set, a surgical discipline, procedure type, set point fluid temperature, set point fluid pressure (in pressure control mode), set point fluid flow rate (in flow control), and/or other parameters (such as display content and/or arrangement, alarm set points and/or indications, and the like).

An exemplary embodiment may be operated in a pressure control mode. The pressure of the fluid may be sensed via a tap (which may be a fluid connection) in fluid communication with the fluid flow path (such as fitting 430) and/or via a pressure sensor located at or in the surgical site (e.g., remote pressure sensor 2069A). In an exemplary embodiment where the fluid is sensed via a tap in fluid communication with the fluid flow path, the pressure of the fluid may be sensed by more than one pressure sensor 2068, 2070 for redundancy purposes.

An exemplary pressure control mode may be configured to pump fluid at about a flow rate that establishes and maintains the pressure within an acceptable range corresponding to the set point established by the user. In an exemplary embodiment, the manner in which pressure is controlled is determined may be based at least in part on the relationship of actual pressure to the set point pressure. Accordingly, the system may determine if actual pressure is in Zone 0 (which may be defined as actual pressure between 0 and the pressure at the lowest value of the set point tolerance band which may be referred to as Low Tolerance Level), Zone 1 (which may be defined as actual pressure between the Low Tolerance Level and the desired pressure level which may be referred to as Set Point Level), Zone 2 (which may be defined as actual pressure between the Set Point Level and the pressure at the highest value of the set point tolerance band which may be referred to as High Tolerance Level), Zone 3 (which may be defined as actual pressure between the High Tolerance Level and the pressure level that triggers alarms which may be referred to as the Alarm Level), and/or Zone 4 (which may be defined as pressure exceeding the Alarm Level).

Some example fluid management units 100 may be configured to employ multiple modes of pressure control. In an exemplary Slope mode, the desired minimum slope of pressure (rate of pressure increase) may be calculated and the fluid flow rate may be adjusted at least in part based on the actual slope of the pressure increase. In an exemplary Control mode, the fluid flow rate may be adjusted incrementally (e.g., by about ±1 ml/min) based at least in part upon a sum of errors methodology. For example, an integral Control mode may include calculating an integral of a pressure error (e.g., set point pressure−actual pressure) over time and adjusting operation of the pump 112 to incrementally adjust a fluid flow rate based at least in part upon the integral of the pressure error. In an exemplary Coast mode, pump speed may be substantially maintained. In an exemplary Reduction mode, the fluid flow rate may be monitored and left substantially unchanged if actual pressure is decreasing, but may be aggressively reduced if pressure is not decreasing with the amount of the reduction based, at least in part, upon the deviation between actual pressure and Set Point Level. In an exemplary Reverse mode, pump rotation may be reversed (e.g., at a fluid flow rate of about 130 ml/min) until actual pressure is reduced to the appropriate Zone.

In some exemplary embodiments, the control scheme employed at a particular time may depend on current and previous Zones of actual pressure as set forth in the following table:

| Current Zone | Previous Zone | Mode |
| --- | --- | --- |
| 0 | — | Slope |
| 1 | 0 | Slope |
| 2 | 1 | Control |
| 3 | 2 | Reduction (if flow rate > 0); Otherwise Reverse |
| 4 | 3 | Reduction (if flow rate > 0); Otherwise Reverse |
| 3 | 4 | Reduction (if flow rate > 0); Otherwise Reverse |
| 2 | 3 or 4 | Coast |
| 1 | 2 | Control |
| 1 | 3 or 4 | Slope |

In some exemplary embodiments, an overpressure alarm may be delayed for a short period (e.g., 5 seconds) to allow reversal of pump 112 to correct an overpressure condition.

An exemplary embodiment may provide automatic and/or manual priming functions. For example, an exemplary automatic priming function may be initiated by a user after installing a tubing set and connecting the tubing set to one or more fluid bags 902, 904. An exemplary automatic priming sequence may include running pump 112 until liquid is detected by bubble detector 132, and may include continuing to run pump 112 after liquid is detected by bubble detector 132. For example, pump 112 may continue to run after liquid is detected by bubble detector 132 to deliver a predetermined volume to fill the remainder of the tubing set provided the user has opened the irrigation valves in the downstream trumpet valve or surgical instrument to vent air. In some exemplary embodiments, the predetermined volume pumped after liquid is detected by bubble detector 132 may vary depending on the type of tubing set being utilized. For example, the fluid management system 10 may be programmed to automatically prime certain known types of tubing sets. An exemplary manual priming function may include a user starting and stopping the pump 112 using a user interface, such as pressing and releasing a button on touch screen display 106. A user may employ the manual priming function to prime a tubing set for which the fluid management system 10 is not programmed for automatic priming, to perform additional priming subsequent to automatic priming, and/or whenever it is desired to manually prime a tubing set, for example.

In some exemplary embodiments, detection of fluid by bubble detector 132 during automatic and/or manual priming may result in initiation of fluid warming by heating assembly 309. In some exemplary embodiments, fluid may be warmed during priming subsequent to detection of fluid by bubble detector 132 to reduce the amount of unwarmed fluid in the tubing set. In such embodiments, overheating of cartridge 410 (such as may occur if heating was initiated without fluid in cartridge 410) may be avoided by utilizing the detection of liquid by bubble detector 132 as an indication of proper priming.

An exemplary embodiment may be operated in a flow control mode. A flow rate may be determined using a known flow rate per rotation of the pump 112 and the rotational speed of the pump 112, for example. In some other exemplary embodiments including other types of positive displacement pumps, the flow rate may be determined in a similar manner. In some exemplary embodiments, a flow rate sensor may be utilized to measure a flow rate. In an exemplary flow control mode, the rotational speed (or equivalent for other types of pumps) may be increased or decreased to minimize or reduce a deviation between a set point flow rate and the flow rate determined from the pump speed, flow rate sensor, etc. An example flow control mode may employ pressure sensors 2068, 2070 to prevent an overpressure condition. For example, the user may select a maximum allowable pressure, which may be approximately 3× the actual fluid pressure in the "open valve" configuration of the trumpet valve or surgical instrument necessary to achieve the desired fluid flow rate and pump 112 may be operated to provide the desired flow rate, without exceeding the maximum allowable pressure. Thus, if fluid flow is obstructed (e.g., by shutting the irrigation valve on a trumpet valve), pump 112 will stop operating prior to reaching the maximum allowable pressure. Once the pressure is reduced (e.g., by opening the irrigation valve on the trumpet valve), pump 112 may resume operation to deliver the desired flow rate.

In some exemplary embodiments, fluid management unit 100 may be operated in an infusion mode. An example infusion mode may be generally similar to the flow control mode described above. For example, an infusion mode may allow a user to input a desired flow rate, such as by using touch screen 106. Similar to the flow control mode described above, an example infusion mode may include a maximum allowable pressure. Pump 112 may be stopped or slowed if the output pressure approaches and/or reaches the maximum allowable pressure. In addition, as mentioned above, one or more bubble detectors 132 may monitor fluid being delivered to the patient. Pump 112 may be stopped if a bubble is detected by one or more bubble detectors 132.

In some example embodiments, fluid management unit 100 may be configured to perform a deficit monitoring function. In some example embodiments, deficit monitoring may be based at least partially upon an assumption that fluid may be one of four places: in the fluid supply containers (e.g., fluid bags 902, 904), in the tubing set, in the patient, and/or in the fluid collection containers (e.g., canisters 906, 908, 910, 912). Any fluid that is not in the fluid supply containers, the tubing set, or in the fluid collection containers is assumed to be in the patient. Thus, some embodiments may utilize total system weights (e.g., the weight of the fluid supply containers plus the fluid collection containers) to calculate the amount of fluid that may be in the patient (e.g., the deficit). For example, after the tubing has been primed, an "initial total system reference weight" may be calculated from the initial weight of the fluid supply containers (e.g., fluid bags 902, 904), as determined by load cells 142, 144 and from the initial weight of the fluid collection containers (e.g., canisters 906, 908, 910, 912), as determined by load cells 206A, 206B, 206C, 206D. The "initial total system reference weight" may be determined (e.g., at the beginning of a procedure when the "run" button is pressed) by summing the initial weight of the fluid supply containers and the initial weight of the fluid collection containers. As the fluid management unit 100 operates, the weight of the fluid supply containers and the weight of the fluid collection containers are monitored by controller at periodic time intervals. At each time interval, a deficit may be calculated by subtracting the combined weights of the fluid supply containers and the fluid collection canisters, as measured at that time, from the initial total system reference weight. In some exemplary embodiments, the periodic time intervals may be sufficiently short (e.g., a fraction of a second) such that the deficit is effectively continuously monitored (e.g., a plurality of times per second). The calculated deficit is an indication of fluid that may be within the patient at the time the deficit is calculated. The calculated deficit at a time interval may be displayed on displays 106, 106A when calculated by the controller for observation by a user of fluid management unit 100.

Some exemplary fluid management units may be configured to automatically detect fluid supply container and/or fluid collection container replacements. For example, replacement of a fluid supply container (e.g., an empty or near empty fluid supply container with a full fluid supply container) may be detected by observation of a substantial increase in the sensed weight of the fluid supply containers. Similarly, replacement of a fluid collection container (e.g., a full or nearly full fluid collection container with an empty fluid collection container) may be detected by observation of a substantial decrease in the sensed weight of the fluid collection containers. Bumping or shaking of fluid management unit 100 to may cause momentary weight errors, so some example fluid management units 100 may be configured to allow a period of time for any transient conditions to dissipate. Thus, transient weight errors may be automatically corrected when the transient ends.

Some example fluid management units 100 may automatically account for fluid supply container replacements by noting the change in fluid supply container weight when the replacement occurs. The change in weight may then be added to the system total reference weight to provide an updated total system reference weight for use in subsequent deficit determinations. Similarly, some example fluid management units 100 may automatically account for fluid collection container replacements by noting the change in fluid collection container weight when the replacement occurs. The change in weight may then be subtracted from the system total reference weight to provide an updated total system reference weight for use in subsequent deficit determinations. Some example systems may automatically account for a plurality of fluid supply container replacement and/or fluid collection container replacement in this manner on an ongoing basis by updating the reference total system weight each time a replacement occurs.

Figure 41:
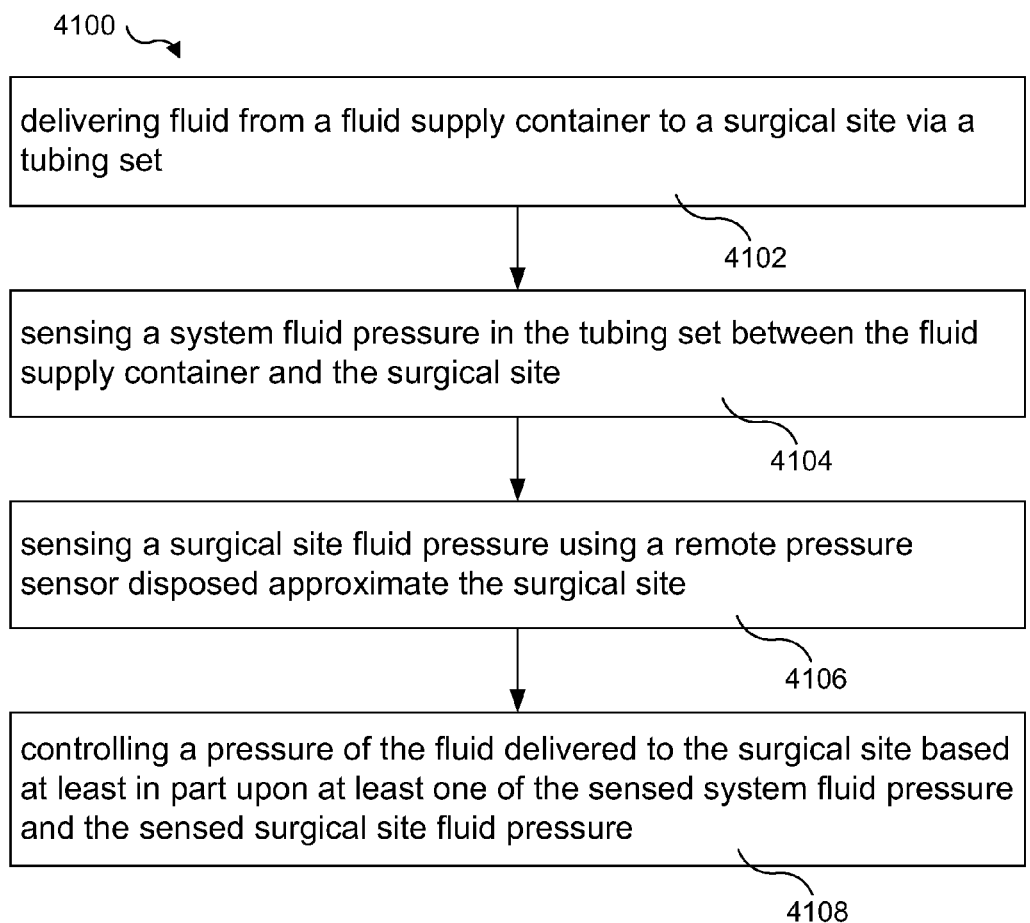
FIG. 41 is a flowchart illustrating an example method of operating a surgical fluid management system.

FIG. 41 illustrates an example method 4100 of operating a surgical fluid management system. Operation 4102 may include delivering fluid from a fluid supply container to a surgical site via a tubing set. Operation 4104 may include sensing a system fluid pressure in the tubing set between the fluid supply container and the surgical site. Operation 4106 may include sensing a surgical site fluid pressure using a remote pressure sensor disposed approximate the surgical site. Operation 4108 may include controlling a pressure of the fluid delivered to the surgical site based at least in part upon at least one of the sensed system fluid pressure and the sensed surgical site fluid pressure.

Figure 42:
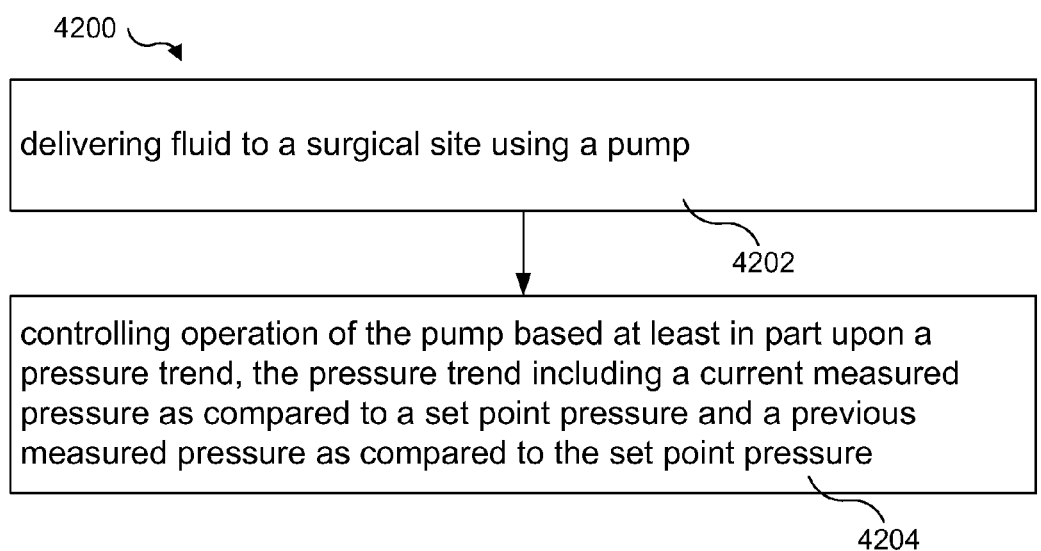
FIG. 42 is a flowchart illustrating an example method of operating a surgical fluid management system.

FIG. 42 illustrates an example method 4200 of operating a surgical fluid management system. Operation 4202 may include delivering fluid to a surgical site using a pump. Operation 4204 may include controlling operation of the pump based at least in part upon a pressure trend, the pressure trend including a current measured pressure as compared to a set point pressure and a previous measured pressure as compared to the set point pressure.

Figure 43:
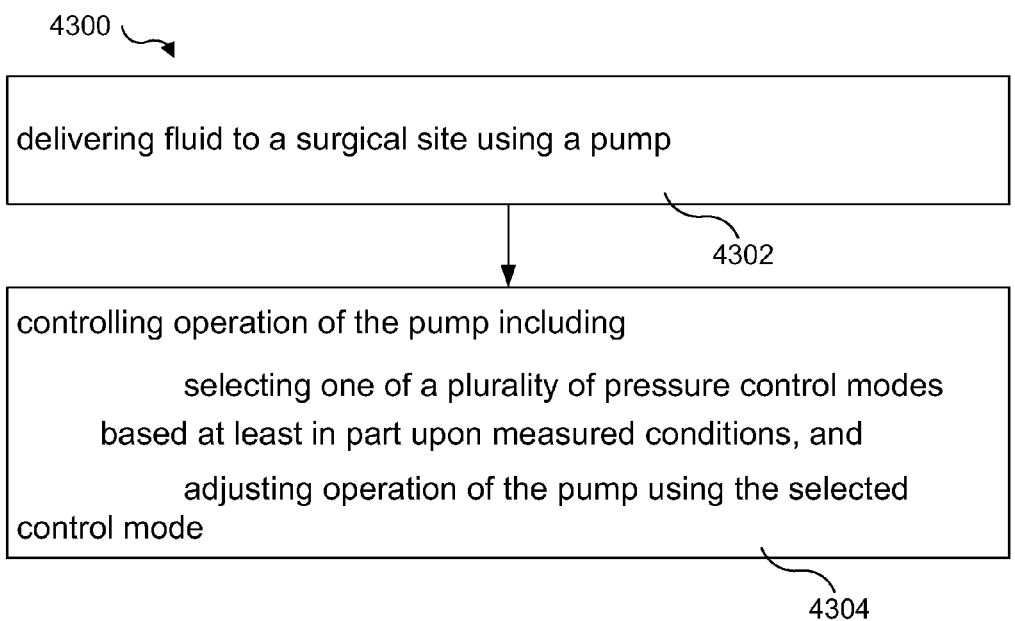
FIG. 43 is a flowchart illustrating an example method of operating a surgical fluid management system.

FIG. 43 illustrates an example method 4300 of operating a surgical fluid management system. Operation 4302 may include delivering fluid to a surgical site using a pump. Operation 4304 may include controlling operation of the pump including selecting one of a plurality of pressure control modes based at least in part upon measured conditions, and adjusting operation of the pump using the selected control mode.

Figure 44:
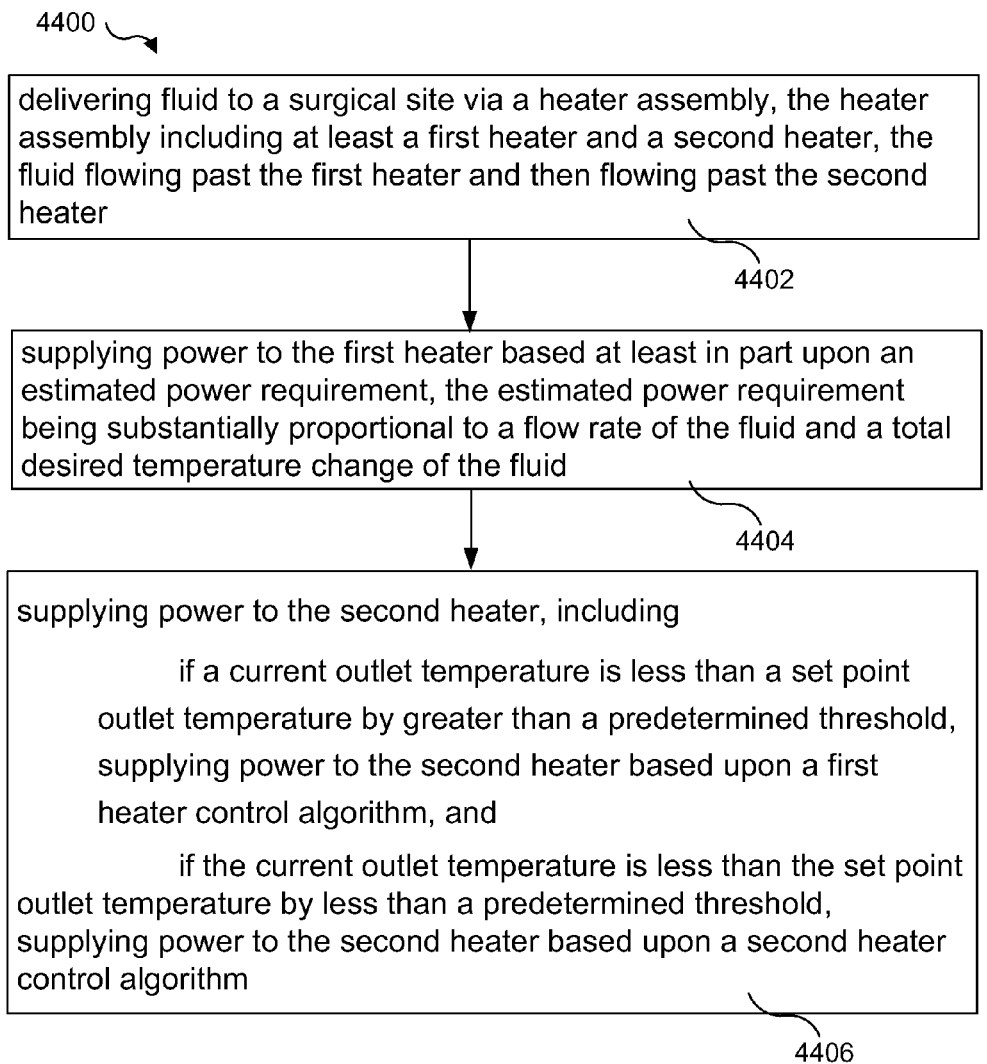
FIG. 44 is a flowchart illustrating an example method of operating a surgical fluid management system.

FIG. 44 illustrates an example method 4400 of operating a surgical fluid management system. Operation 4402 may include delivering fluid to a surgical site via a heater assembly, the heater assembly including at least a first heater and a second heater, the fluid flowing past the first heater and then flowing past the second heater. Operation 4404 may include supplying power to the first heater based at least in part upon an estimated power requirement, the estimated power requirement being substantially proportional to a flow rate of the fluid and a total desired temperature change of the fluid. Operation 4406 may include supplying power to the second heater, including, if a current outlet temperature is less than a set point outlet temperature by greater than a predetermined threshold, supplying power to the second heater based upon a first heater control algorithm, and if the current outlet temperature is less than the set point outlet temperature by less than a predetermined threshold, supplying power to the second heater based upon a second heater control algorithm.

Figure 45:
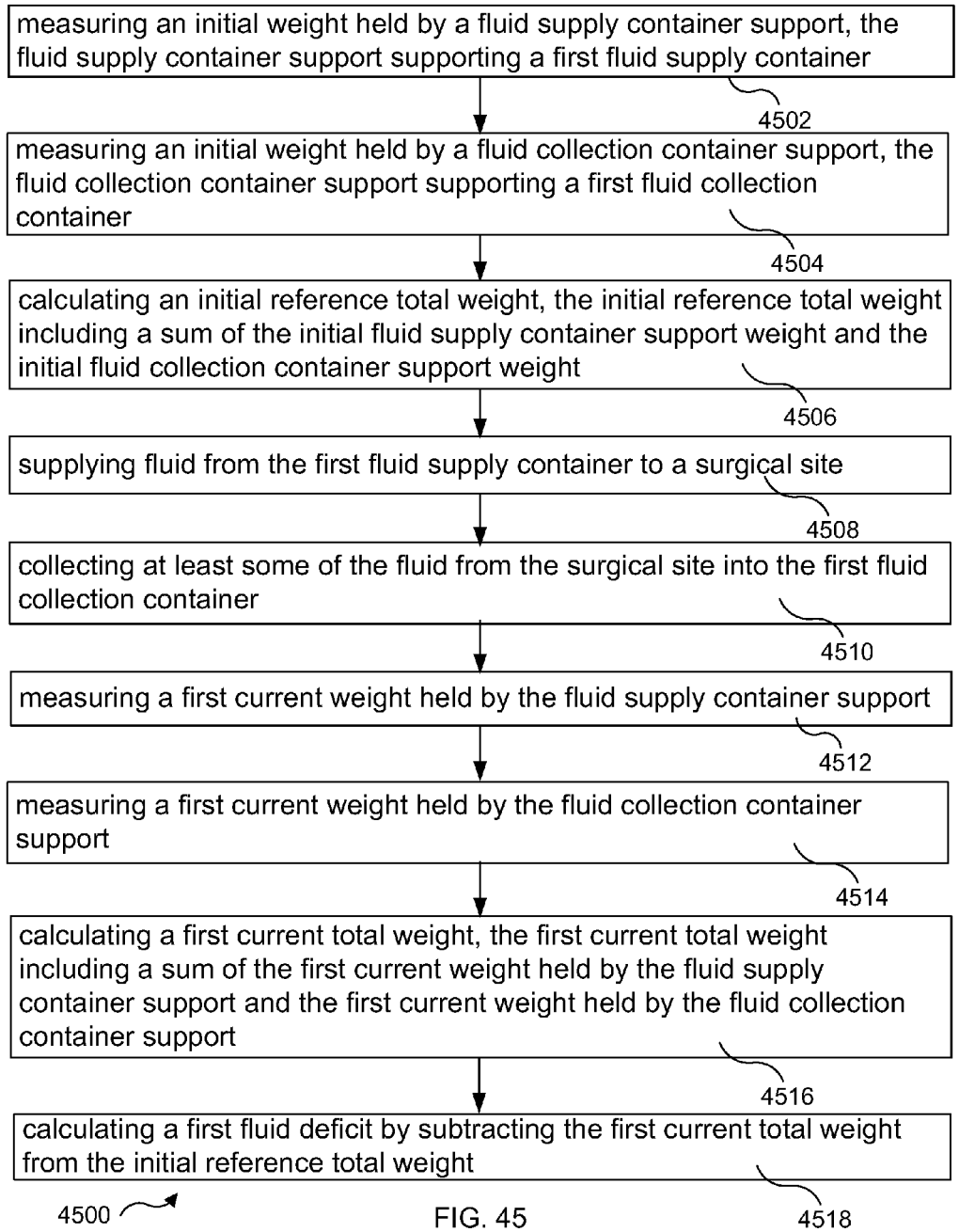
FIG. 45 is a flowchart illustrating an example method of monitoring a fluid deficit in a surgical fluid management system.

FIG. 45 illustrates an example method 4500 of monitoring a fluid deficit in a surgical fluid management system. Operation 4502 may include measuring an initial weight held by a fluid supply container support, the fluid supply container support supporting a first fluid supply container. Operation 4504 may include measuring an initial weight held by a fluid collection container support, the fluid collection container support supporting a first fluid collection container. Operation 4506 may include calculating an initial reference total weight, the initial reference total weight including a sum of the initial fluid supply container support weight and the initial fluid collection container support weight. Operation 4508 may include supplying fluid from the first fluid supply container to a surgical site. Operation 4510 may include collecting at least some of the fluid from the surgical site into the first fluid collection container. Operation 4512 may include measuring a first current weight held by the fluid supply container support. Operation 4514 may include measuring a first current weight held by the fluid collection container support. Operation 4516 may include calculating a first current total weight, the first current total weight including a sum of the first current weight held by the fluid supply container support and the first current weight held by the fluid collection container support. Operation 4518 may include calculating a first fluid deficit by subtracting the first current total weight from the initial reference total weight.

Figure 46:
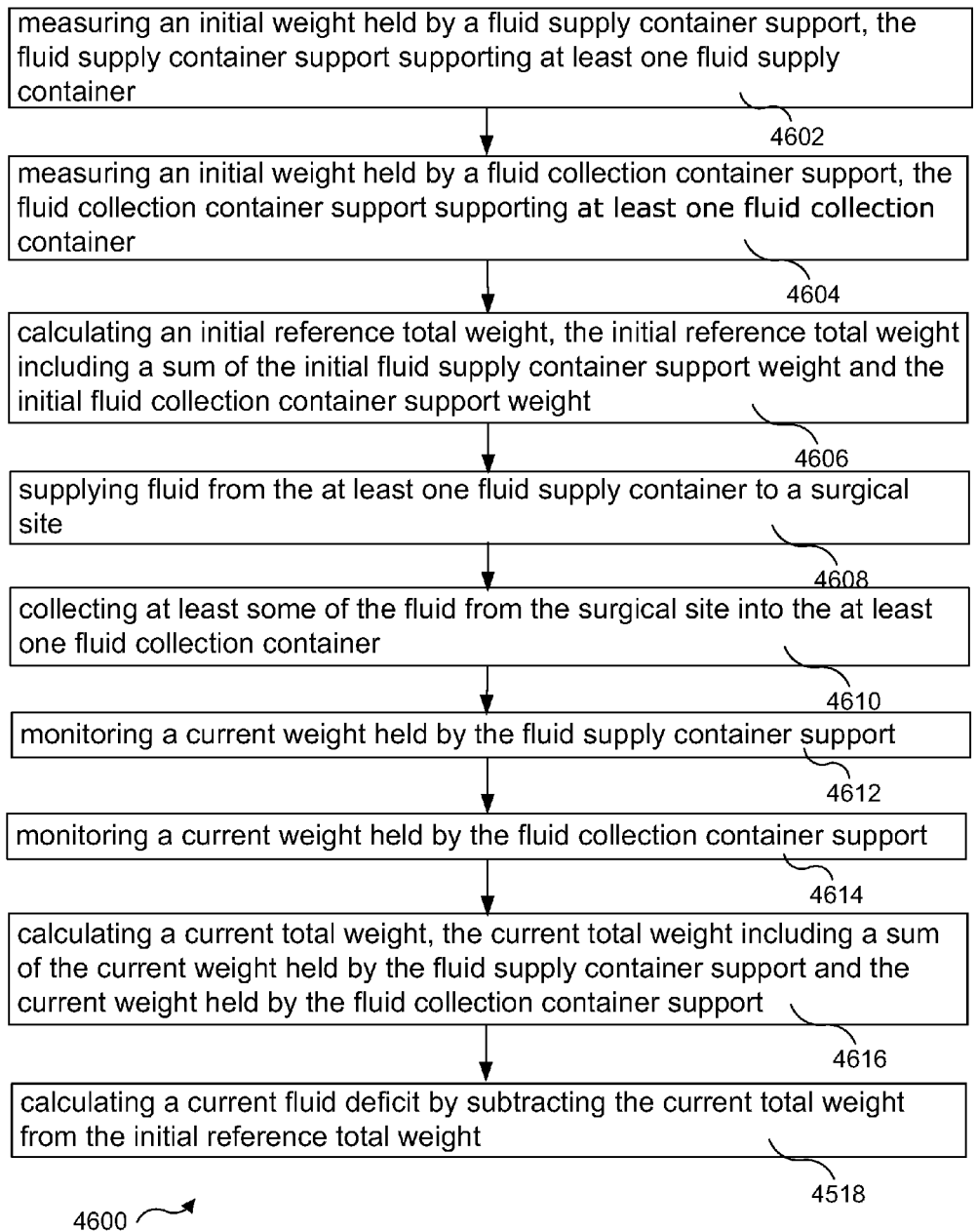
FIG. 46 is a flowchart illustrating an example method of monitoring a fluid deficit in a surgical fluid management system.

FIG. 46 illustrates an example method 4600 of monitoring a fluid deficit in a surgical fluid management system. Operation 4602 may include measuring an initial weight held by a fluid supply container support, the fluid supply container support supporting at least one fluid supply container. Operation 4604 may include measuring an initial weight held by a fluid collection container support, the fluid collection container support supporting at least one fluid collection container. Operation 4606 may include calculating an initial reference total weight, the initial reference total weight including a sum of the initial fluid supply container support weight and the initial fluid collection container support weight. Operation 4608 may include supplying fluid from the at least one fluid supply container to a surgical site. Operation 4610 may include collecting at least some of the fluid from the surgical site into the at least one fluid collection container. Operation 4612 may include monitoring a current weight held by the fluid supply container support. Operation 4614 may include monitoring a current weight held by the fluid collection container support. Operation 4616 may include calculating a current total weight, the current total weight including a sum of the current weight held by the fluid supply container support and the current weight held by the fluid collection container support. Operation 4618 may include calculating a current fluid deficit by subtracting the current total weight from the initial reference total weight.

Figure 47:
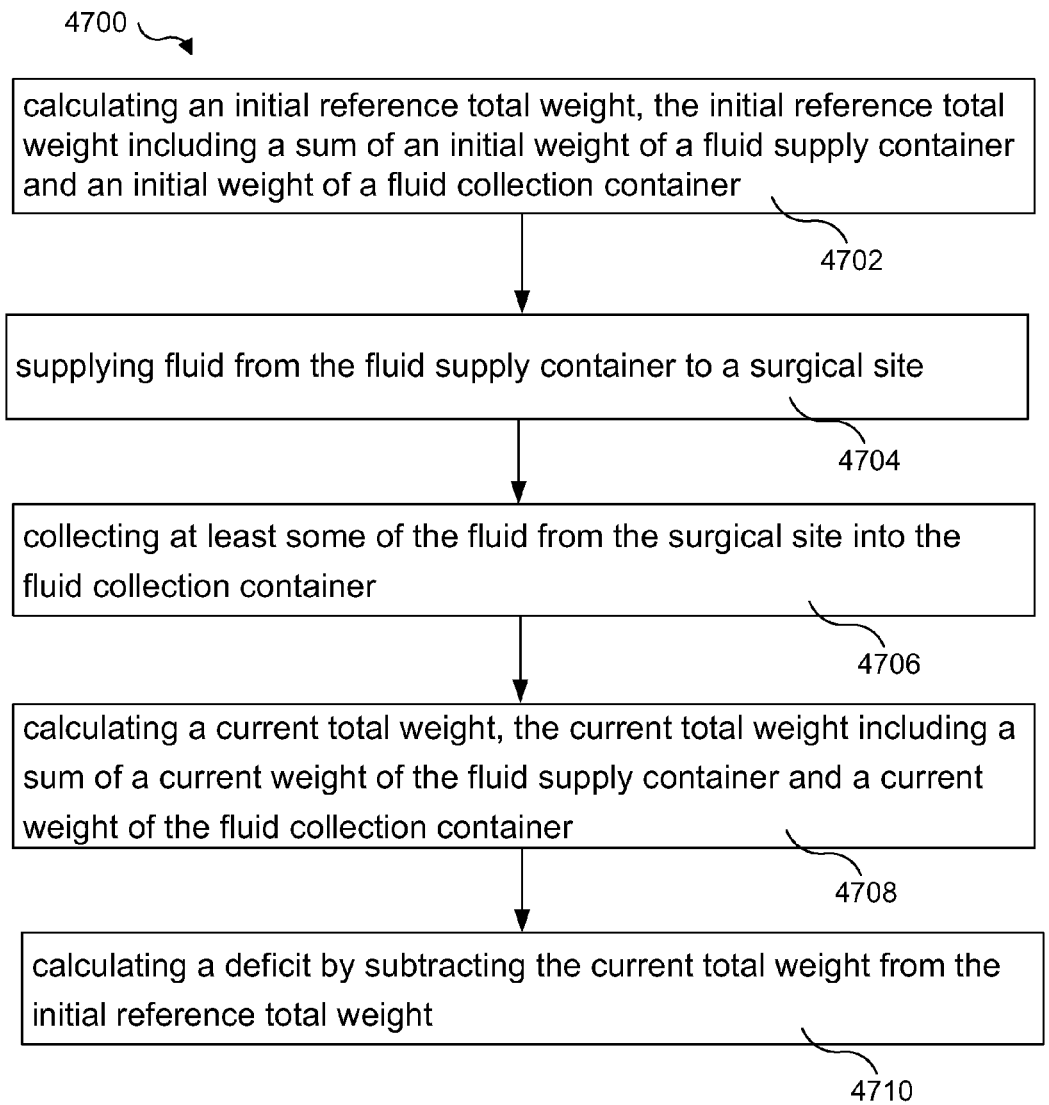
FIG. 47 is a flowchart illustrating an example method of operating a surgical fluid management system.

FIG. 47 illustrates an example method 4700 of operating a surgical fluid management system. Operation 4702 may include calculating an initial reference total weight, the initial reference total weight including a sum of an initial weight of a fluid supply container and an initial weight of a fluid collection container. Operation 4704 may include supplying fluid from the fluid supply container to a surgical site. Operation 4706 may include collecting at least some of the fluid from the surgical site into the fluid collection container. Operation 4708 may include calculating a current total weight, the current total weight including a sum of a current weight of the fluid supply container and a current weight of the fluid collection container. Operation 4710 may include calculating a deficit by subtracting the current total weight from the initial reference total weight.

Figure 48:
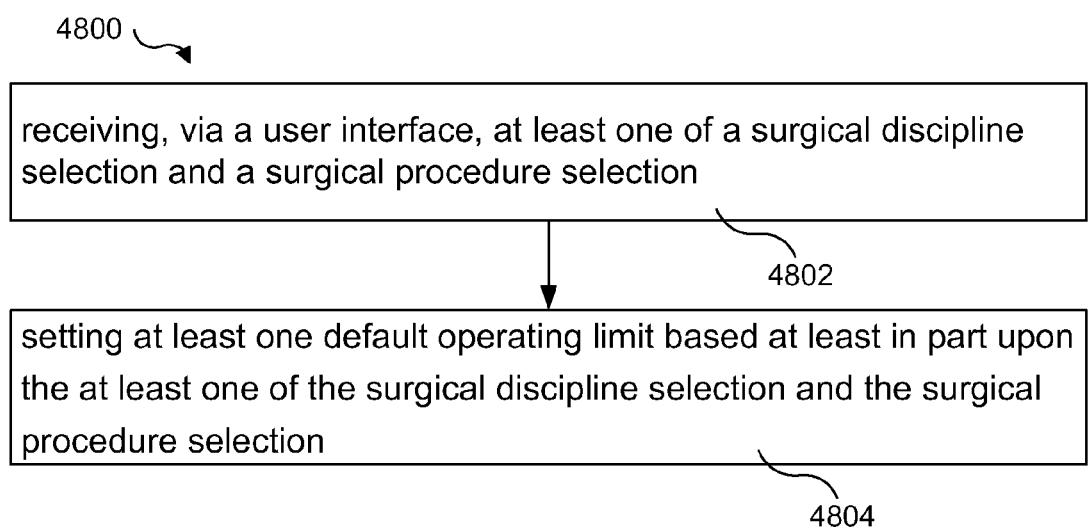
FIG. 48 is a flowchart illustrating an example method of operating a multi-functional fluid management system.

FIG. 48 illustrates an example method 4800 of operating a multi-functional fluid management system. Operation 4802 may include receiving, via a user interface, at least one of a surgical discipline selection and a surgical procedure selection. Operation 4804 may include setting at least one default operating limit based at least in part upon the at least one of the surgical discipline selection and the surgical procedure selection.

Figure 49:
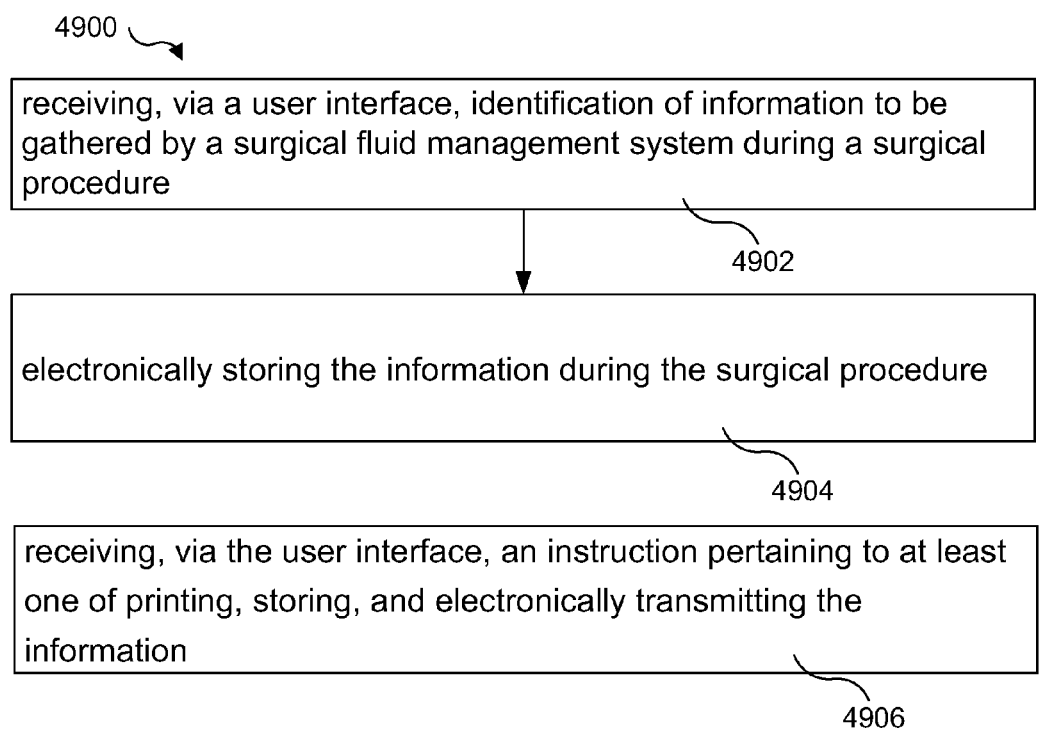
FIG. 49 is a flowchart illustrating an example method of operating a surgical fluid management system.

FIG. 49 illustrates an example method 4900 of operating a surgical fluid management system. Operation 4902 may include receiving, via a user interface, identification of information to be gathered by a surgical fluid management system during a surgical procedure. Operation 4904 may include electronically storing the information during the surgical procedure. Operation 4906 may include receiving, via the user interface, an instruction pertaining to at least one of printing, storing, and electronically transmitting the information.

Figure 50:
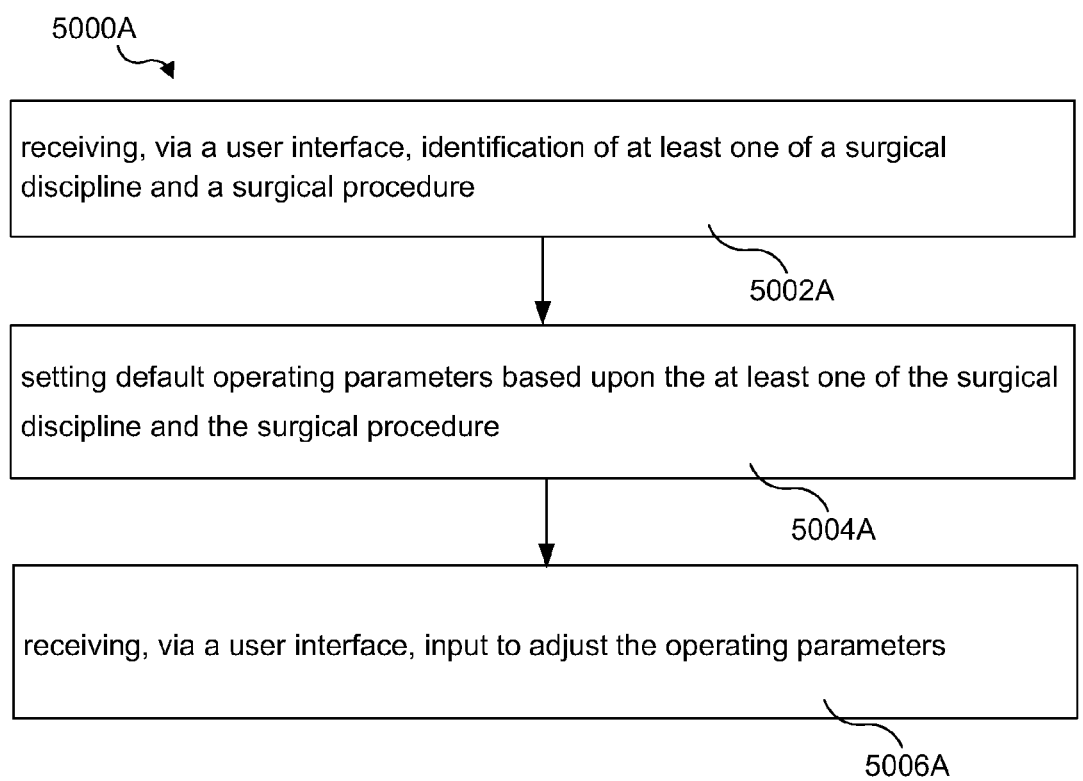
FIG. 50 is a flowchart illustrating an example method of operating a multi-functional surgical fluid management system.

FIG. 50 illustrates an example method 5000A of operating a multi-functional surgical fluid management system. Operation 5002A may include receiving, via a user interface, identification of at least one of a surgical discipline and a surgical procedure. Operation 5004A may include setting default operating parameters based upon the at least one of the surgical discipline and the surgical procedure. Operation 5006A may include receiving, via a user interface, input to adjust the operating parameters.

Figure 51:
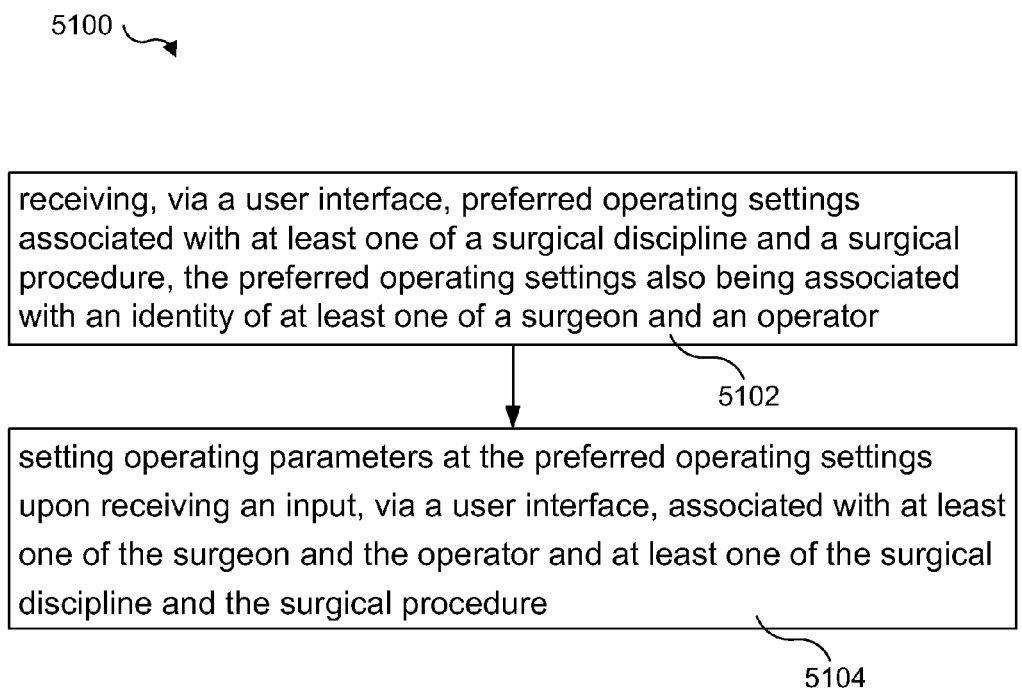
FIG. 51 is a flowchart illustrating an example method of operating a surgical fluid management system.

FIG. 51 illustrates an example method 5100 of operating a surgical fluid management system. Operation 5102 may include receiving, via a user interface, preferred operating settings associated with at least one of a surgical discipline and a surgical procedure, the preferred operating settings also being associated with an identity of at least one of a surgeon and an operator. Operation 5104 may include setting operating parameters at the preferred operating settings upon receiving an input, via a user interface, associated with at least one of the surgeon and the operator and at least one of the surgical discipline and the surgical procedure.

Figure 52:
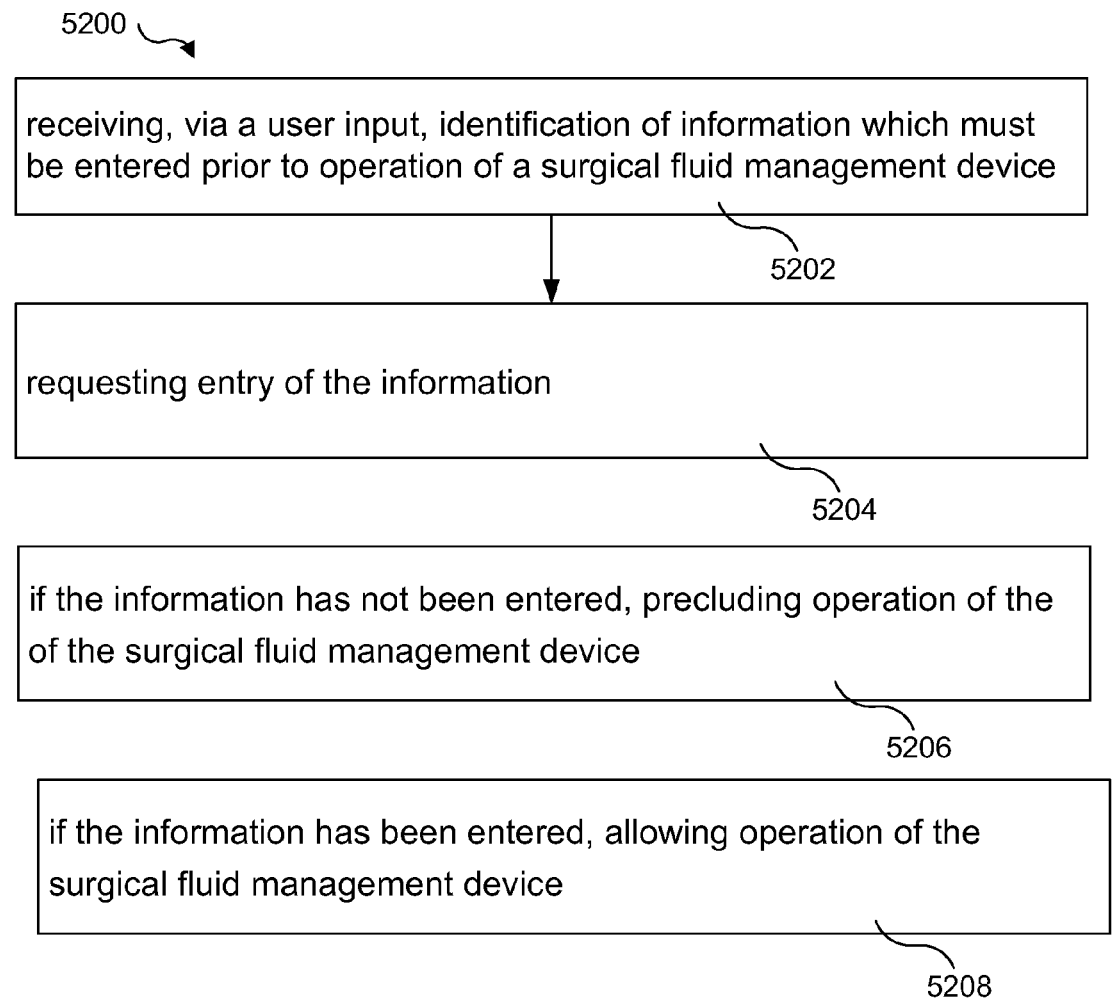
FIG. 52 is a flowchart illustrating an example method for of controlling a surgical fluid management device.

FIG. 52 illustrates an example method 5200 of controlling a surgical fluid management device. Operation 5202 may include receiving, via a user input, identification of information which must be entered prior to operation of a surgical fluid management device. Operation 5204 may include requesting entry of the information. Operation 5206 may include if the information has not been entered, precluding operation of the of the surgical fluid management device. Operation 5208 may include if the information has been entered, allowing operation of the surgical fluid management device.

As has been described above, the present invention is directed to a fluid management system 10 for managing fluids used in connection with a wide variety of "medical procedures" that may be performed in connection with humans and animals. As should be apparent from the invention disclosure provided above, the term "medical procedure" as used in the present application refers to procedures, including, but not limited to: surgical procedures, irrigation procedures, and infusion procedures, said procedures performed on humans or animals. It should be understood that a medical procedure may be comprised of multiple elements, wherein each element is an individual medical procedure. In other words, a plurality of individual medical procedures may be carried out in succession to complete a comprehensive medical procedure. Thus, "medical procedure" may refer to an individual medical procedure or a comprehensive medical procedure comprised of a plurality of individual medical procedures.

The medical procedures may be associated with such medical disciplines, including but not limited to: gynecology, obstetrics, urology, orthopedics, general surgery and trauma. Examples of medical procedures, include but are not limited to, hysteroscopy, cystoscopy, ureteroscopy, laparascopy, arthroscopy, and infusion. These medical procedures are identified in general or specific terms.

The medical procedures carried out with use of fluid management system 10 disclosed herein may involve one or more of the following fluid delivery functions, including but not limited to: fluid irrigation, distention of a body cavity, and fluid infusion into a patient. Fluid management system 10 of the present invention may also provide additional functions with respect to the medical procedures, including, but not limited to: fluid deficit monitoring associated with delivery and return of fluid to/from a site (wherein, the site is a surgical site or a patient), fluid warming, fluid pulsation, and circulation of fluid (e.g., into and out of a body cavity).

Depending upon the selected medical procedure, fluid management system 10 operates in either a pressure control mode (wherein control system 8 controls pump 112 to deliver fluid to the site at approximately a target pressure), or in a flow control mode (wherein control system 8 controls pump 112 to deliver fluid to the site at approximately a target flow rate).

In order to safely and effectively deliver fluid for carrying out the medical procedure, several "default" operating parameters are established in accordance with the medical procedure selected by the user. These default operating parameters include, but are not limited to, a target pressure and a target flow rate. A range of acceptable pressures and flow rates are respectively defined by minimum and maximum pressures and minimum and maximum flow rates. By maintaining the pressure within the acceptable pressure range and maintaining the flow rate within the acceptable flow rate range, fluid management system 10 of the present invention safely and effectively delivers fluid to the site in connection with the selected medical procedure.

Described below are additional features of the present invention. Certain aspects of these features have been described in the preceeding sections of the specification.

Heating Suspension

In accordance with one embodiment of the present invention, heater assembly 309 is disabled when pump 112 is inactive (i.e., not rotating), unless fluid management system 10 is in an "idle" state. This disablement of heater assembly 309 prevents any dangerous conditions that could arise from heating stagnant fluid in cartridge 410. Control system 8 is programmed to deactivate pump 112 when a threshold fluid pressure ($P_{threshold}$) is detected by control system 8 (e.g., using pressure sensors 2068, 2070). The threshold fluid pressure ($P_{threshold}$) is typically achieved when a user closes an inflow or outflow valve on a surgical instrument, or tubing downstream of cartridge 410 is intentionally or unintentionally occluded.

However, it is recognized that if tubing located upstream of cartridge 410 is occluded or the fluid supply source (i.e., fluid supply container(s); fluid bags 902, 904) have become depleted, then pump 112 continues to be activated due to the fact that the threshold fluid pressure ($P_{threshold}$) cannot be achieved. As a result, heater assembly 309 continues to be enabled (even though the fluid in cartridge 410 is stagnant). This situation may result in undesirable conditions, such as overheating of the fluid in cartridge 410.

According to an aspect of the present invention, control system 8 is programmed to monitor the weight of the fluid supply source when pump 112 is in an activate state, and thereby determine whether or not fluid is "flowing." As discussed above, one or more load cells 142, 144, may output electrical signals associated with the weight of the fluid supply containers suspended from the fluid bag hangers. Control system 8 determines whether the weight of the fluid supply source is decreasing. If the weight of the fluid supply source is not decreasing, then control system 8 determines that tubing upstream of cartridge 410 is occluded, or that the fluid supply source has become depleted, and thus disables heater assembly 309 to prevent any further heating of the fluid.

If a user selects a medical procedure that allows fluid heating and the user has enabled the fluid heating function (e.g., by selecting heater button 4064 as shown in FIG. 35), then heater assembly 309 will continue to be enabled if (a) pump 112 is activated; (b) bubble detector 132 is sensing the presence of fluid; and (c) the weight of the fluid supply source is decreasing. If any one of the conditions (a), (b) or (c) is not present, then heater assembly 309 will be disabled to stop further heating of the fluid in cartridge 410.

In accordance with an alternative embodiment, control system 8 does not monitor the weight of the fluid supply source, but instead, receives a signal from a flow sensor located along a fluid path upstream of cartridge 410 indicative of whether fluid is flowing along the fluid path.

Manual Lost Fluid Estimator

In accordance with certain medical procedures (such as operative hysteroscopy), fluid absorption by a patient must be carefully monitored to guard against excess fluid absorption, which may result in complications. The amount of fluid that can be safely absorbed by the patient is dependent upon a number of factors, including the type of fluid being used.

In some fluid management systems, the fluid deficit is monitored by measuring the amount of fluid delivered to a site and the amount of fluid returned from the site (e.g., via suction or gravity). Such fluid management systems may provide an alarm when the fluid deficit is approaching an unsafe level, and prevent any further fluid delivery to the site when the fluid deficit has reached an unsafe limit. However, such fluid management systems are not able to measure the amount of fluid that is "lost" including, but not limited to, fluid that has spilled onto the floor and/or has been absorbed by surgical drapes, gowns, and/or blankets. As a result, such "lost" fluid is deemed by the fluid management system to have been absorbed by the patient, and thereby results in an artificially high fluid deficit. Consequently, the user may experience corresponding false fluid deficit alarms, procedure interruptions, and/or premature terminations of procedures.

According to an aspect of the present invention, control system 8 is programmed to present the user with a data entry screen (via touch screen 106) that allows the user to manually enter a value that is an estimate of the amount of fluid "lost" during a medical procedure. This value may be entered in units of volume or weight.

Control system 8 incorporates the "lost" fluid estimate into the fluid deficit calculations (such as those described in detail above), thus providing the user with a fluid deficit having greater accuracy. For example, the "lost" fluid estimate may be incorporated into the fluid deficit calculations by subtracting the weight of the estimated "lost" fluid from the initial total system weight, or by adding the weight of the estimated "lost" fluid to the current total system weight.

To minimize the risk associated with "lost" fluid estimates and to ensure accountability for users making and manually entering the "lost" fluid estimates, control system 8 may also be programmed to provide one or more of the following features:

1. Visually and/or audibly providing a warning (via touch screen 106 and/or speaker 2052) to the user against overestimating the "lost" fluid due to inaccurate fluid deficit monitoring and corresponding adverse consequences that could result from overestimations;
2. Visually and/or audibly providing a warning (via touch screen 106 and/or speaker 2052) to the user against entering "lost" fluid estimates considered nominal in nature (e.g., less than 100 ml);
3. Providing a "lost" fluid estimate on a printed procedure summary that may be printed by printer 111 at the completion of a medical procedure to provide a printed record of the medical procedure. Printer control box 4082 may provide a user with a selection for printing the "lost" fluid estimate at the end of a medical procedure (see FIG. 37); and
4. Programming control system 8 to prohibit the "lost" fluid estimate from being incorporated into fluid deficit calculations during the medical procedure in order to eliminate the possibility of a user manipulating or effectively raising the fluid deficit alarm limit by overestimating the amount of "lost" fluid. In this case, the only purpose for manual entry of the "lost" fluid estimate would be to have such estimate printed in the procedure summary for a more accurate record of the fluid deficit occurring during the medical procedure.

Default Maximum Fluid Deficit by Fluid Type

As discussed above, the amount of fluid that can be safely absorbed by a patient is dependent upon a several factors, including the type of fluid being used. However, some fluid management systems default to a fluid deficit alarm limit that is independent of the type of fluid being used, and thus allows a user to adjust the fluid deficit alarm limit within a range inclusive of all permissible levels of fluid absorption for all types of fluids that could be used during a medical procedure. As a result, a user may program the fluid management system with a fluid deficit alarm limit set to a high limit (e.g., 2500 ml) when the fluid management system is being used to supply a fluid that requires a lower fluid deficit alarm limit (e.g., 1500 ml).

In accordance with an aspect of the present invention, where deficit monitoring is enabled, control system 8 is programmed to prompt a user to enter or select a "type" of fluid to be used in connection with the medical procedure, via touch screen 106. Control system 8 defaults to an appropriate/safe fluid deficit alarm limit for the entered or selected fluid "type" and allows the user to adjust such fluid deficit alarm limit within a range deemed safe for that particular "type" of fluid. The "type" of fluid indicated by the user, the fluid deficit alarm limit set by the user, and the total fluid deficit may be provided on a printed procedure summary at the conclusion of the medical procedure.

Alternatively, control system 8 may default to a fluid deficit alarm limit deemed safe for all possible fluids and only prompt the user to enter or select the fluid "type" if the user desires to increase the fluid deficit alarm limit above the initial default fluid deficit alarm limit or other low fluid deficit alarm limit.

Deficit Monitoring by Type of Fluid Used and Purge Button

During certain medical procedures, including operative hysteroscopy having both hysteroscopic and laparoscopic elements, it may be necessary to change the tubing set and the type of fluid being used during the procedure to accomplish the respective distention and/or irrigation functions. For example, in the hysteroscopic element, an endoscopic tubing set and saline fluid may be used. In the laparoscopic element, a laparoscopic tubing set and a non-conductive fluid (such as glycine) may be used in order to perform electrocautery. It may also be necessary to return to the hysteroscopic element (i.e., endoscopic tubing and saline) to complete the procedure.

Fluid management system 10 is operable in both pressure and flow control modes, and includes tubing sets that facilitate the transition between to two or more elements of a procedure (e.g. between hysteroscopic and laparoscopic elements). These tubing sets include a proximal portion that includes cartridge 410, and a distal portion downstream of cartridge 410 that terminates in a connector, such as a luer lock connector (e.g., for hysteroscopic use) or a surgical instrument, such as a trumpet valve (e.g., for laparoscopic use). For example, see FIGS. 9 and 24. It is contemplated that other types of connectors and instruments may be used in connection with the present invention.

In one embodiment of the present invention, the distal portion is adapted to be interchangeable, i.e., a distal portion terminating in a first type of connector (e.g., a luer lock connector) can be interchanged with a distal portion terminating a surgical instrument (e.g., a trumpet valve) or a second type of connector. This allows a luer lock connector to be interchanged with a trumpet valve, thereby facilitating a transition between different medical procedures (e.g., laparoscopic and hysteroscopic procedures). Interchangeable distal portions are discussed in detail below.

If the fluid used during a second element of a procedure is different from the fluid used during a first element of the procedure, then a user must ensure that the fluid used in the first element of the procedure is completely purged from fluid management system 10 prior to commencing the second element of the procedure. This requires the user to manually estimate the amount of fluid that must be pumped to completely purge the fluid used in the first element of a procedure. Moreover, the user must manually track the fluid deficit associated with the first element of the procedure and the fluid deficits associated with any subsequent elements of the procedure in order to have an accurate total fluid deficit.

In accordance with another aspect of the present invention, control system 8 is programmed to present the user with a prompt or data entry screen (via touch screen 106) that allows the user to indicate a transition from a first element of a procedure to a second element of the procedure (e.g., from a hysteroscopic element to a laparoscopic element). Upon such indication, control system 8 uses touch screen 106 to prompt the user to select the procedure associated with the second element; instruct the user to change the distal portion of tubing; and query the user whether a different fluid will be used for the second element of the procedure and, if so, prompts the user to enter or select the "new" fluid via touch screen 106. If the user indicates that a different fluid will be used for the second element of the procedure, control system 8 is programmed to display a "purge" button that, when pressed, causes control system 8 to activate pump 112 in order to pump a sufficient volume of the "new" fluid to thereby completely purge the "old" fluid from the proximal portion of the tubing set before connecting the new distal portion.

Control system 8 is further programmed to incorporate the above-described "purge" function into the fluid deficit monitoring calculations (described above) in order to avoid artificially high fluid deficit and corresponding false alarms, procedure interruptions, and/or early procedure terminations. For example, the volume of "purged" fluid may be incorporated into the fluid deficit calculations by subtracting the weight of the "purged" fluid from the initial total system weight, or by adding the weight of the "purged" fluid to the current total system weight.

Control system 8 is also programmed to present the user with the "purge" button if the user indicates to control system 8 that a fluid change is going to be made during a single element of the procedure (e.g., during a hysteroscopic element). In this situation the distal portion remains unchanged. As a result of selecting the "purge" button, control system 8 performs the fluid "purge" and adjusts the fluid deficit monitoring levels accordingly.

Control system 8 is further programmed to automatically track and display (a) the fluid deficit associated with the "old" fluid used during the first element of the procedure; (b) the fluid deficit associated with the "new" fluid used during the second element of the procedure; and (c) the total fluid deficit for the entire procedure (i.e., all elements of the procedure). Furthermore, if there is a third (or subsequent) element(s) of the procedure (e.g., hysteroscopic element changing to laparoscopic element changing back to hysteroscopic element), control system 8 is programmed to track and display the fluid deficits based on the fluid used during that element.

Change Canister Prompt

Fluid management unit 100 is capable of sensing a significant weight change indicative of the replacement of a fluid collection container. A user may be presented with a "change canister" button displayed on touch screen 106 to eliminate potential errors that can be caused by movement or vibration of fluid management unit 100 (e.g., shifting of fluid inside canisters 906, 908, 910, 912). However, if the user fails to press the "change canister" button, the volume of the fluid associated with the full fluid supply container that was removed is no longer accounted for and, therefore, deemed by control system 8 to have been absorbed by the patient. This situation can result in an artificially high fluid deficit calculation and display, as well as accompanying false alarms, procedure interruptions, or early procedure terminations.

According to an aspect of the present invention, control system 8 is programmed to sense a large decrease in weight on load cell base 204 indicative of the removal of a full or substantially full fluid supply container, without the user having pressed the "canister change" button. Furthermore, control system 8 is programmed to store the weight determined prior to the significant weight change, and displays a query on touch screen 106 to request the user to confirm that a fluid supply container has been removed (e.g., "Did you just remove a canister? If so, please press canister change button now"). As described above, the total weight supported by load cells 206A, 206B, 206C, 206D is about equal to the sum of the weight of suction canister hanger 202, the empty weights of canisters 906, 908, 910, 912, and the weight of any contents of canisters 906, 908, 910, 912.

Bolus Button

During certain medical procedures (e.g., ureteroscopy), a user may need a bolus of higher pressure fluid to carry out a particular mechanical function (such as move kidney stones, separate tissue, expand passageways, etc.). The bolus can be achieved via a syringe or bulb that is manually operated by the user. This approach may result in unsafe fluid pressure levels or volumes, and often requires a separate tubing set which can be inefficient and costly.

In accordance with an aspect of the present invention, when a user selects a medical procedure where a "bolus" of fluid might be necessary (e.g., ureteroscopy), control system 8 is programmed to display (via touch screen 106) a "bolus" button that can be selected by the user at any time during the procedure. Upon selection of the "bolus" button, control system 8 is programmed to provide a "bolus" of fluid. The user may set parameters associated with the "bolus" including, but not limited to, a desired fluid pressure level and a desired duration (in either time or fluid volume). It is also contemplated that control system 8 may be programmed to display numerous "bolus" buttons, wherein each button is associated with a specific pressure and duration combination. This feature enables the user to more efficiently employ the correct "bolus" without having to "reprogram" a single "bolus" button for different pressure and duration combinations.

Intra-Procedure Multi-Functionality

In the medical discipline of gynecology, the associated procedures may involve both hysteroscopic and laparoscopic elements of a procedure. Typically, these procedures will commence with diagnostic or operative hysteroscopy and progress to gynecologic and/or abdominal laparoscopy. Fluid management systems that require the use of multiple devices and/or multiple tubing sets to complete such types of multi-element procedures decrease efficiency, increases the costs associated with such procedures, and might potentially adversely affect patient safety.

In hysteroscopy, irrigation fluid is circulated into and out of the uterine cavity at a pressure deemed optimal to maintain proper distention and to achieve good visualization by washing out blood and debris resulting from the procedure. Due to the dangers associated with intravasation, the fluid deficit (i.e., the difference in volume between the amount of fluid delivered to a site and the amount of fluid returned from the site), must be closely monitored by the fluid management system. Also, due to procedural requirements and/or the adverse outcomes associated with intraoperative hypothermia, warming of the irrigation fluid to approximately body temperature may be necessary or desired.

In laparoscopy, the irrigation fluid is delivered to the site at a flow rate deemed appropriate to clear the site of blood and debris and to maintain good visualization. Again, due to procedural purposes and/or the adverse outcomes associated with intraoperative hypothermia, warming of the irrigation fluid to approximately body temperature may be desired or necessary.

Due to functional limitations of certain existing fluid management systems, procedures that include multiple elements (e.g., hysteroscopic and laparoscopic elements) may require the use of multiple fluid management systems during such procedures. These functional limitations, include, but are not limited to: single operating mode (i.e., operable in a pressure control mode or a fluid control mode, but not both modes); lack of tubing sets that can be configured for hysteroscopic and laparoscopic use (i.e., requiring the use of separate tubing sets for each element of a procedure); lack of automated deficit monitoring capabilities; lack of user-selectable on-demand fluid warming capabilities; and lack of trumpet valves with suction/irrigation and electrocautery capability.

According to an aspect of the present invention there is provided a "multi-functional" fluid management system 10 that includes a fluid management unit 100 that operates in fluid pressure control mode or flow control mode depending upon a selected medical procedure, monitors fluid deficits, provides on-demand fluid warming; and provides a tubing set that is configurable for various different medical procedures, such as hysteroscopy and laparoscopy (suction/irrigation alone or in combination with electrocautery).

Figure 53A:
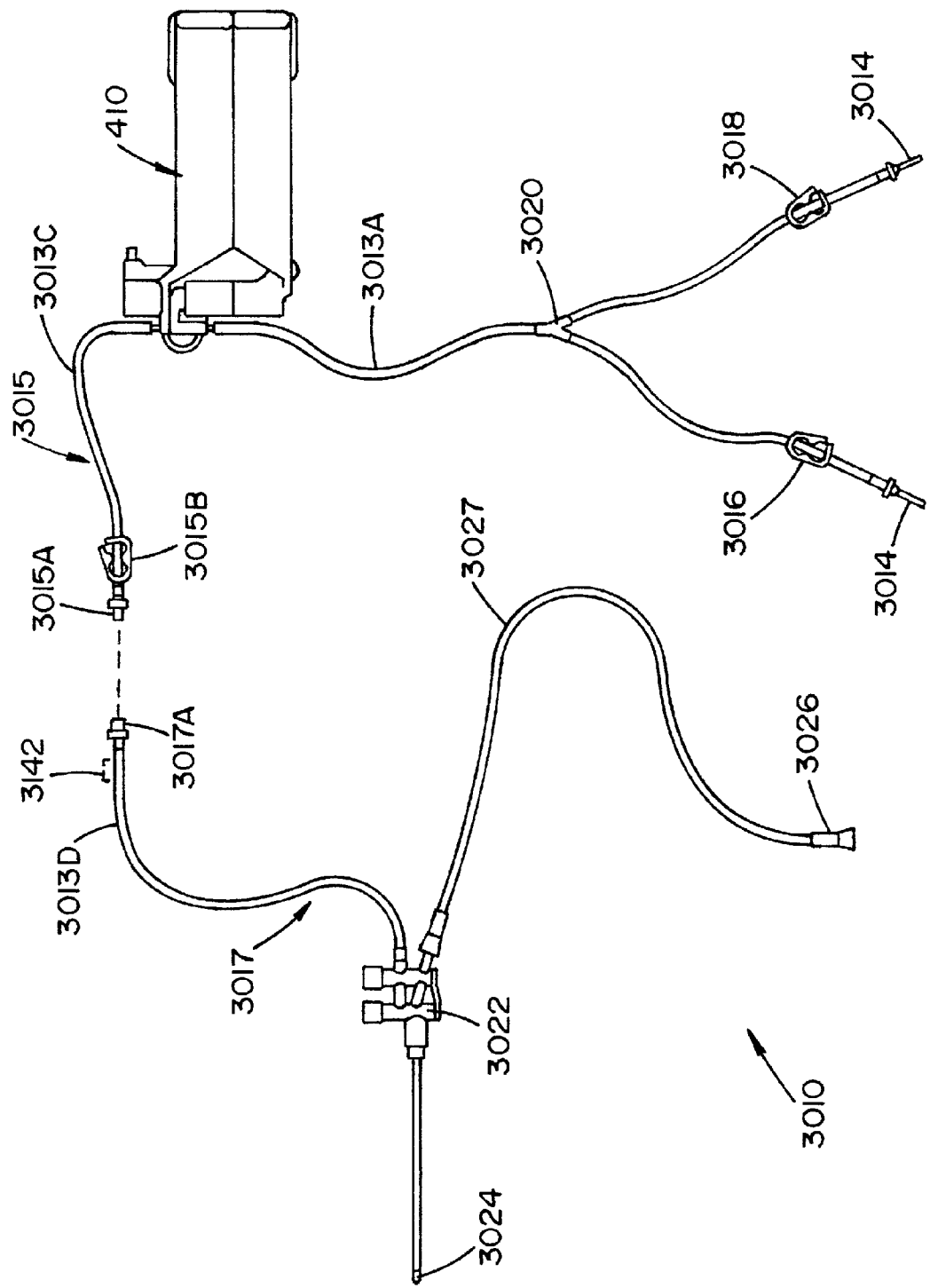
FIG. 53A illustrates a tubing set having detachable proximal and distal portions, according to a first embodiment.
Figure 53B:
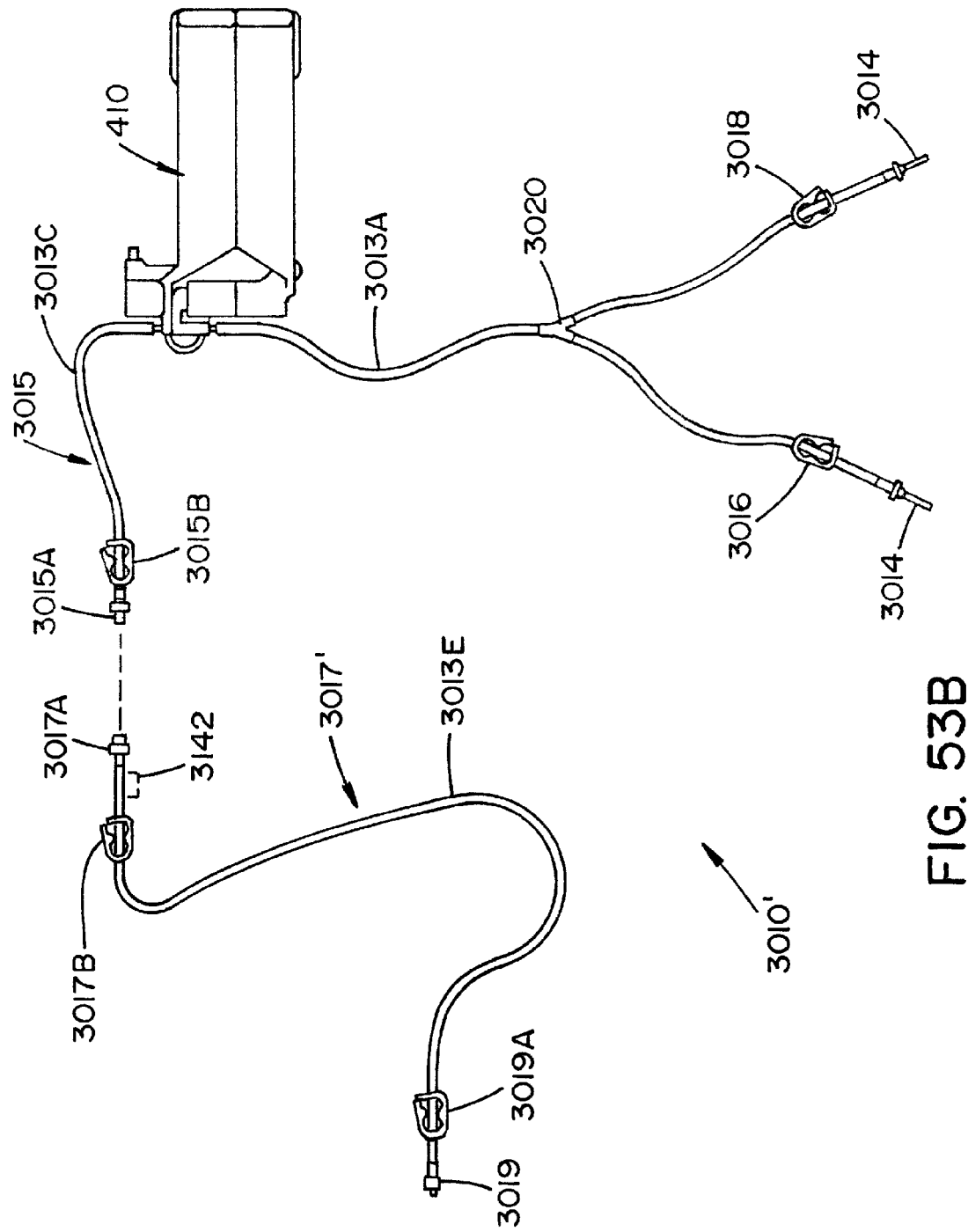
FIG. 53B illustrates a tubing set having detachable proximal and distal portions, according to a second embodiment.

FIG. 53A illustrates a trumpet valve tubing set 3010 useable in connection with a first medical procedure (e.g., a laparoscopic procedure), while FIG. 53B illustrates a luer lock connector (single lumen) tubing set 3010' useable in connection with a second medical procedure (e.g., a hysteroscopic procedure). Each tubing set 3010, 3010' is comprised of a cartridge or proximal portion 3015 and a distal portion 3017, 3017'. The proximal portion includes dual spikes 3014 with clamps 3016, 3018, a "Y" connector 3020, a first section 3013A of tubing connecting "Y" connector 3020 and a cartridge 410 (fluid inflow), cartridge 410, and a second section 3013C of tubing (with a clamp 3015B) that connects cartridge 410 and a connector 3015A (fluid outflow).

Distal portions 3017, 3017' are adapted for use with a particular medical procedure. In the illustrated embodiment, distal portion 3017 provides a trumpet valve, while distal portion 3017' provides a single lumen terminating in a luer lock connection or other connection to a surgical instrument. It is contemplated that the distal portion may be adapted for use with devices other than those illustrated herein.

Distal portion 3017 includes a tubing section 3013D (irrigation line) and a connector 3017A for connection to proximal portion 3015 of tubing set 3010. In the illustrated embodiment, tubing section 3013D terminates at the distal end in a trumpet valve 3022 and a conjoined suction tubing or line 3027 that terminates in a standard suction connector 3026.

Distal portion 3017' includes a tubing section 3013E (irrigation line) and a connector 3017A with an optional clamp 3017B for connection to proximal portion 3015 of tubing set 3010'. In the illustrated embodiment, tubing section 3013E terminates at the distal end in a luer lock 3019 with a clamp 3019A For example, fluid management system 10 may be configured for a hysteroscopy procedure by selecting the hysteroscopy procedure from a medical procedure menu (e.g., see FIG. 32), which automatically puts fluid management system 10 in a pressure control mode. A user installs proximal portion 3015 of tubing set 3010' (FIG. 53B) that includes dual bag spikes 3014 and "y" connector 3020, a cartridge 410 that is inserted 410 into slot 310 (see FIG. 2), and a segment 3013C of tubing extending from cartridge 410 to a male or female connector 3015A for enabling coupling to distal portion 3017' of tubing set 3010' outside of fluid management unit 100. Distal portion 3017' includes mating connector 3017A and segment 3013E of tubing for delivering fluid from fluid management unit 100 to the site. Segment 3013E of tubing terminates in luer lock connector 3019 for coupling to a hysteroscope or other instrument.

Control system 8 facilitates transitions between two different elements of a procedure. For example, when the hysteroscopic element of the procedure is complete, or it becomes necessary to interrupt the hysteroscopic element of the procedure to perform a laparoscopic element, the user indicates to control system 8, via touch screen 106, a change in the medical procedure to laparoscopy. As a result, control system 8 automatically transitions the fluid management unit 100 to a flow control mode.

The user disconnects distal portion 3017' of the tubing used for hysteroscopy from proximal portion 3015, and connects distal portion 3017 (FIG. 53A) to proximal portion 3015. Proximal portion 3015 includes mating connector 3015A that couples to connector 3017A of distal portion 3017. Distal portion 3017 includes segment 3013D of tubing that terminates in trumpet valve 3022, for delivering fluid from fluid management system 10 to the site. Trumpet valve 3022 has a standard suction/irrigation probe or a combination probe that includes suction/irrigation and electrocautery. When the distal portion substitution has been completed by the user, the user will indicate to control system 8 (via touch screen 106) that fluid management system 100 is properly configured to start the laparoscopic element of the procedure. If a different fluid is being used, then the "purge" function described above may be implemented.

Although fluid deficit is less of a concern during laparoscopy, control system 8 is programmed to prompt the user (via touch screen 8) to indicate whether the user wants to continue fluid deficit monitoring. If the user elects to continue the deficit monitoring, control system 8 will regard the laparoscopy element as a continuation of the same procedure (i.e., the originally selected procedure) for purposes of the deficit monitoring function. If the user elects to discontinue the deficit monitoring, control system 8 will regard the laparoscopy element as a "new" procedure. Accordingly, the deficit monitoring function of control system 8 is adapted to facilitate changes between elements of a procedure.

When the laparoscopic element of the procedure is complete, or when it becomes necessary to interrupt the laparoscopic element to perform an additional hysteroscopic element, the user indicates to control system 8, via touch screen 106, a change in the procedure to return back to hysteroscopy. As a result, control system 8 automatically transitions the fluid management unit 100 back to a pressure control mode. Fluid management unit 100 indicates, via touch screen 106, that the fluid deficit monitoring calculations from the previous hysteroscopic element of the procedure will be restored and comprise the basis for continuing the fluid deficit monitoring calculations. The user changes the distal portion of tubing from the laparoscopic tubing (FIG. 53A) to the hysteroscopic tubing (FIG. 53B), and then indicates to control system 8 (via touch screen 106), that fluid management system 100 is properly configured to return to the hysteroscopic element of the procedure.

It should be appreciated that the following features of fluid management system 10 enable performance of the functions described above: operates in a pressure control mode or a flow control mode depending on the selected procedure; tubing sets are configurable for different procedures (e.g., hysteroscopic and laparoscopic procedures); microprocessor-based fluid deficit monitoring (for storing, recalling and computing fluid deficit calculations); selectable on-demand fluid warming; and combination suction/irrigation electrocautery trumpet valve probes.

Fluid management system 10 as described above has several advantages, including, but not limited to:

a. only one fluid management system is needed to perform a procedure involving multiple elements (e.g. hysteroscopic and laparoscopic elements), thereby saving time since only one fluid device has to be set up, reducing costs since only one device has to be acquired and maintained, and minimizing space requirements in the operating room (OR);

b. only one tubing set is needed, with appropriate accessories, thereby reducing costs over separate tubing sets needed for hysteroscopic and laparoscopic elements;

c. the ability of fluid management system 10 to function for multiple elements (e.g., both hysteroscopy and laparoscopy elements) increases the efficiency of the procedure;

d. the ability of fluid management system 10 to store, retrieve, and build upon fluid deficit calculations from a first element (e.g., a hysteroscopic element) performed earlier in a procedure increases patient safety by reducing possible recording errors;

e. the "selectable" on-demand fluid warming feature of fluid management system 10 enables the use of fluid management system 10 in a variety of situations, i.e., when there are procedural requirements for fluid warming (such as the warm fluid indication in certain hysteroscopic sterilization procedures), when there are concerns with intraoperative hypothermia that require on-demand fluid warming, and when there are procedural requirements or other clinical issues that require room-temperature or cool irrigation fluid; and f. the trumpet valve of fluid management system 10 can receive a standard suction/irrigation probe or a combination suction/irrigation and electrocautery probe, thereby saving time and money, and eliminating the need for two separate ports into an insufflated surgical site.

g. the purge function when transitioning from a first fluid to a second fluid.

According to another embodiment of the present invention, fluid management system 10 includes an automatic tubing detection feature and allows control system 8 to automatically detect changes in tubing sets in use with fluid management system 10. In this regard, control system 8 is programmed to automatically recognize a change between a distal portion 3017' of tubing set 3010' (e.g., used for hysteroscopy) and a distal portion 3017 of tubing set 3010 (e.g., used for laparoscopy), and automatically respond to such detected change by making a corresponding change to system operation, e.g., changing between pressure mode control and flow control mode, and adjusting alarm limits. The automatic recognition contemplated herein may be accomplished using detection technology well know in the art, including but not limited to RFID tagging, or a variety of other electrical (wired and wireless communication devices), mechanical, optical, or pneumatic means. An illustrated embodiment of the present invention will be described with reference to a fluid management system 10 that includes radio frequency identification device (RFID) tagging as an electrical communication device.

As will be described in detail below, a readable memory such as an RFID is integral with the distal portion of the tube set. The RFID includes a memory that stores data identifying characteristics of the distal portion of the tube set. An interface unit reads the data in the RFID memory. Based on this data, the control system 8 then regulates operation of fluid management system 10 according to a pressure control mode or a flow control mode in accordance with the type of distal portion that has been detected using the RFID.

Control system 8 also controls pump 112 such that fluid, when required, is delivered at a pressure level or flow rate according to the data read out from the RFID memory. This data is also used by the control system 8 to regulate priming of pump 112 so that when fluid management system 10 is initially setup, a head of irrigation fluid can be pumped close to the end of the hand piece tool from which the fluid is to be discharged.

Referring now to FIGS. 53A and 53B, respective distal portion 3017, 3017' of tube sets 3010, 3010' include an RFID 3142. RFID 3142 includes a memory in which data is stored that identifies characteristics of distal portion 3017, 3017' (e.g., which type(s) of medical procedure(s) use the distal portion, whether the distal portion is used in connection with a pressure control mode or a flow control mode, and associated pressure level or flow rate). RFID 3142 also includes the following components that facilitate the reading of data to and the writing of data from the memory: a coil, a signal modulator/demodulator; a processor; and a rechargeable power supply.

Figure 54:
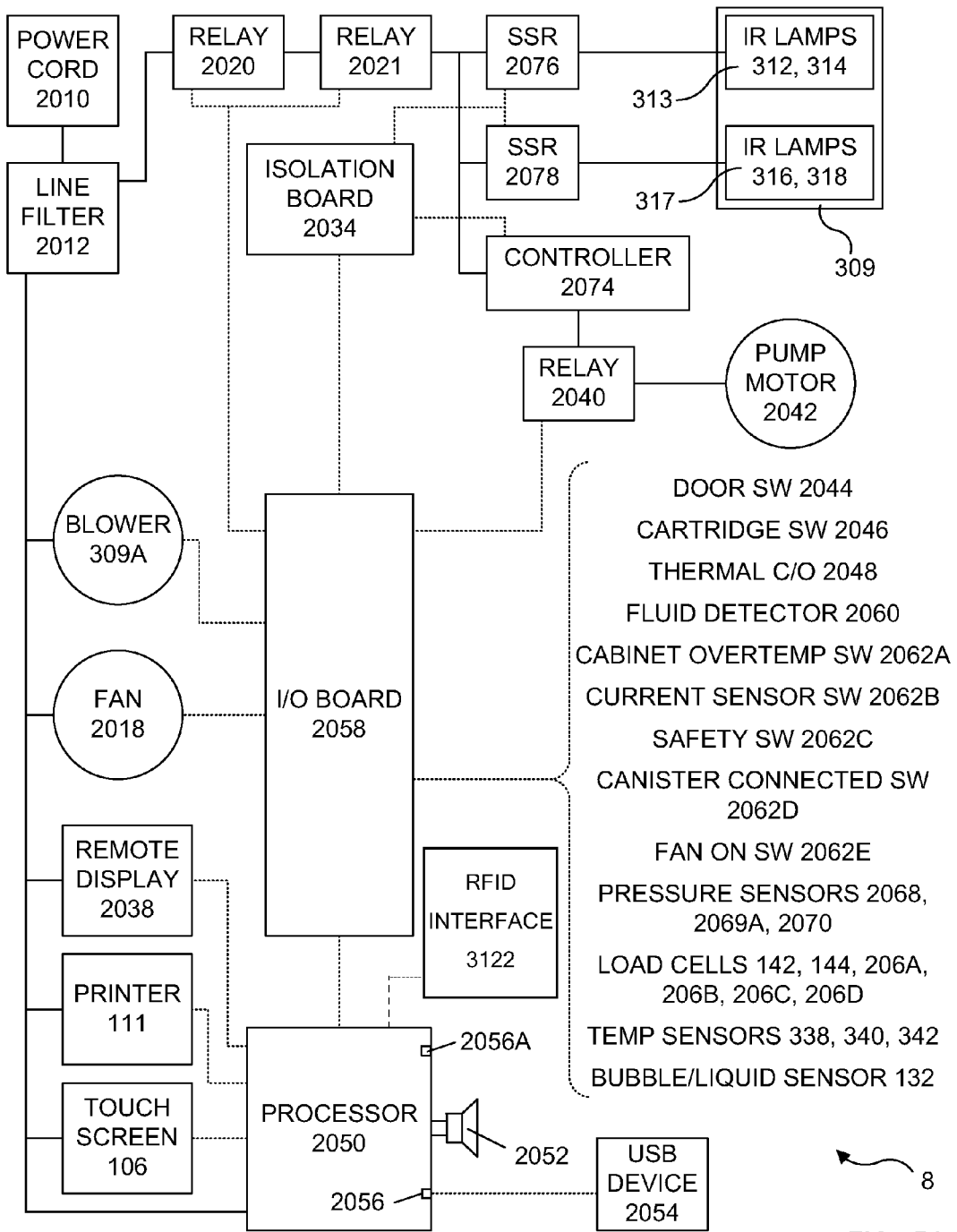
FIG. 54 is a block diagram illustrating an embodiment of the control system for the fluid management system that includes an RFID interface.

With reference to FIG. 54, control system 8 is modified to include an RFID interface unit 3122 for communicating with RFID 3142. In this regard, interface unit 3122 reads data from and writes data to RFID 3142. Interface unit 3122 includes an antenna that is positioned such that when the distal portion 3017 or 3017' is positioned for connection with proximal portion 3015, the antenna and the coil integral with RFID 3142 are close enough to facilitate inductive signal transfer therebetween. Interface unit 3122 also includes a modulator/demodulator for encoding the signals for forwarding data to RFID 3142 and decoding received signals received from RFID 3142. Once a distal portion 3017 or 3017' is connected with proximal portion 3015, data is read out of the RFID memory. It should be appreciated that interface unit 3122 may alternatively be located at cartridge 410 and communicate with processor 2050 via wireless or wired communications.

A manual process (as described above) may be used as the primary means for indicating to fluid management unit 100 that a change in the type of procedure is occurring, and the automatic tubing detection feature serving as a secondary redundant safety check. For example, if the user manually indicates, via touch screen 106, that a change to a laparoscopy procedure was going to occur, but mistakenly couples a distal portion of tubing intended for a hysteroscopy procedure, control system 8 is programmed to identify this error, and notify the user of the mistake via the touch screen 106 and preclude operation of fluid management system 10 until the correct distal portion of tubing is attached.

It should be further noted that a configurable tubing set allows for the use of specialized distal portions. For example, a distal portion with an integrated pressure relief valve may be used for patient safety to guard against overpressurization of the cavity during hysteroscopy, and a distal portion without a pressure relief valve may be used for laparoscopy. Inclusion of the pressure relief valve for laparoscopy would involve unnecessary costs and could be problematic due to higher required fluid pressures needed to deliver the required flow rates for laparoscopy.

Apparatus and methods according to the present disclosure may be utilized in a wide variety of settings, such as surgical and/or other procedures performed on humans and/or animals, dental surgeries and/or other procedures, and/or any other medical and/or veterinary procedures, such as those involving irrigation, distention, and/or infusion.

While exemplary embodiments have been set forth above for the purpose of disclosure, modifications of the disclosed embodiments as well as other embodiments thereof may occur to those skilled in the art. Accordingly, it is to be understood that the disclosure is not limited to the above precise embodiments and that changes may be made without departing from the scope. Likewise, it is to be understood that it is not necessary to meet any or all of the stated advantages or objects disclosed herein to fall within the scope of the disclosure, since inherent and/or unforeseen advantages of the may exist even though they may not have been explicitly discussed herein.

Having described the invention, the following is claimed:

1. A fluid management system for supplying fluids of at least two types, said system comprising:
   at least one fluid supply container;
   at least one fluid collection container;
   a pump configured to deliver a fluid from the at least one fluid supply container to a site, said site being a surgical site or a patient;
   a control system for operating the fluid management system in at least one of (1) a pressure control mode, wherein said control system controls the pump to deliver fluid to the site at approximately a target pressure or (2) a flow control mode, wherein said control system controls the pump to deliver fluid to the site at approximately a target flow rate, said control system including:
      a user interface for communication between the control system and a user, including inputting data to the control system and outputting data from the control system;
      a fluid deficit monitoring function for determining a fluid deficit that is a difference between (i) a volume of fluid delivered to the site from the at least one fluid supply container and (ii) a volume of fluid returned from the site to the at least one fluid collection container; and
      a fluid deficit alarm function for activating a fluid deficit alarm when a fluid deficit exceeds a fluid deficit alarm limit indicative of a maximum fluid deficit associated with a type of fluid communicated to the control system.

2. A fluid management system according to claim 1, wherein said control system determines (a) a first fluid deficit associated with a first fluid used during a first medical procedure; (b) a second fluid deficit associated with a second fluid used during a second medical procedure; and (c) a total fluid deficit associated with all fluids used during the first, second and any subsequent medical procedures.

3. A fluid management system according to claim 1, wherein said control system further comprises a data recording device for providing a printed summary at the conclusion of a medical procedure, said printed summary identifying the fluid deficit.

4. A fluid management system according to claim 1, wherein said control system further comprises a data recording device for providing a printed summary at the conclusion of a medical procedure, said printed summary identifying said type of fluid communicated to the control system.

5. A fluid management system according to claim 1, wherein said control system provides a deficit alarm limit selection via said user interface for adjustment of said fluid deficit alarm limit within a predetermined range.

6. A fluid management system according to claim 5, wherein said control system further comprises a data recording device for providing a printed summary at the conclusion of a medical procedure, said printed summary identifying the fluid deficit alarm limit indicative of the maximum fluid deficit associated with said type of fluid communicated to the control system.

7. A fluid management system according to claim 1, wherein said control system determines a change from a first medical procedure to a second medical procedure, by communication via the user interface.

8. A fluid management system according to claim 7, wherein said control system determines a change from a first fluid used in the first medical procedure to a second fluid used in the second medical procedure, by communication via the user interface.

9. A fluid management system according to claim 8, wherein in response to communications via the user interface, said control system initiates a purge function that activates the pump to purge fluid from the tubing set.

10. A fluid management system according to claim 9, wherein said control system incorporates the purged fluid into fluid deficit calculations.

11. A fluid management system according to claim 1, wherein said fluid management system further comprises a tubing set that includes:
   a proximal portion having a fluid heating cartridge, and
   a distal portion having a first end and a second end, the first end connectable to one end of the proximal section.

12. A fluid management system according to claim 11, wherein said distal portion is a first distal portion having a connector at the second end.

13. A fluid management system according to claim 12, wherein said connector is a luer lock connector.

14. A fluid management system according to claim 11, wherein said distal portion is a second distal portion having a surgical instrument at the second end.

15. A fluid management system according to claim 14, wherein said surgical instrument is a trumpet valve.

16. A fluid management system according to claim 11, wherein said control system includes means for detecting characteristics associated with said distal portion to select either the pressure control mode or the flow control mode according to the detected characteristics of the distal portion.

17. A fluid management system according to claim 16, wherein said distal portion includes an electrical communication device for identifying characteristics of the distal portion.

18. A fluid management system according to claim 17, wherein said electrical communication device is a radio frequency identification device (RFID) that includes a memory for storing data identifying characteristics of the distal portion.

19. A method of operating a fluid management system for supplying fluids of at least two types, wherein said system includes at least one fluid supply container, at least one fluid collection container, a pump configured to deliver a fluid from the at least one fluid supply container to a site, said site being a surgical site or a patient; and a control system for controlling operation of the fluid management system, said method comprising:

inputting data to the control system and outputting data from the control system via a user interface;

selecting a medical procedure that requires (1) a pressure control mode, wherein said control system controls the pump to deliver fluid to the site at approximately a target pressure or (2) a flow control mode, wherein said control system controls the pump to deliver fluid to the site at approximately a target flow rate;

determining a fluid deficit that is a difference between (i) a volume of fluid delivered to the site from the at least one fluid supply container and (ii) a volume of fluid returned from the site to the at least one fluid collection container;

associating a fluid deficit alarm limit with a type of fluid being supplied by the at least one fluid supply container; and activating a fluid deficit alarm when the fluid deficit exceeds the fluid deficit alarm limit associated with the type of fluid being supplied by the at least one fluid supply container.

20. A method of operating a fluid management system according to claim 19, wherein said fluid management system further comprises a tubing set including a proximal portion having a fluid heating cartridge, and a distal portion having a first end and a second end, the first end connectable to one end of the proximal section, wherein said method further comprises:

detecting characteristics associated with said distal portion to select either the pressure control mode or the flow control mode according to the detected characteristics of the distal portion.

21. A method of operating a fluid management system according to claim 19, wherein said method further comprises:

determining a change from a first fluid used in a first medical procedure to a second fluid used in the second medical procedure, by communication via the user interface.

* * * * *